US012667087B2

(12) United States Patent
Jin et al.

(10) Patent No.: US 12,667,087 B2
(45) Date of Patent: Jun. 30, 2026

(54) METHODS OF TREATMENT WITH AMINOLEVULINIC ACID SYNTHASE 2 (ALAS2) MODULATORS

(71) Applicant: Agios Pharmaceuticals, Inc., Cambridge, MA (US)

(72) Inventors: Shengfang Jin, Newton, MA (US); Barden Chan, Brookline, MA (US); Gavin Whissell, Belmont, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 756 days.

(21) Appl. No.: 17/616,790

(22) PCT Filed: Jun. 5, 2020

(86) PCT No.: PCT/US2020/036424

§ 371 (c)(1),
(2) Date: Dec. 6, 2021

(87) PCT Pub. No.: WO2020/247819

PCT Pub. Date: Dec. 10, 2020

(65) Prior Publication Data

US 2024/0276957 A1 Aug. 22, 2024

Related U.S. Application Data

(60) Provisional application No. 62/893,942, filed on Aug. 30, 2019, provisional application No. 62/858,699, filed on Jun. 7, 2019.

(51) Int. Cl.

| | |
|---|---|
| ***A01K 67/0275*** | (2024.01) |
| ***C12N 9/10*** | (2006.01) |
| ***C12N 9/22*** | (2006.01) |
| ***C12N 15/11*** | (2006.01) |
| ***C12N 15/85*** | (2006.01) |

(52) U.S. Cl.

CPC ........ *A01K 67/0275* (2013.01); *C12N 9/1029* (2013.01); *C12N 9/22* (2013.01); *C12N 15/11* (2013.01); *C12N 15/8509* (2013.01); *C12Y 203/01037* (2013.01); *A01K 2217/054* (2013.01); *A01K 2217/075* (2013.01); *A01K 2227/105* (2013.01); *A01K 2267/0306* (2013.01); *C12N 2015/8536* (2013.01); *C12N 2310/20* (2017.05); *C12N 2800/80* (2013.01)

(58) Field of Classification Search

CPC .......... A01K 67/0275; A01K 2227/105; A01K 2267/0306; A01K 2217/054; A01K 2217/075; C12N 9/1029; C12N 9/22; C12N 2800/80; C12N 15/11; C12N 15/8509; C12N 2310/20; C12N 2015/8536; C12Y 203/01037

See application file for complete search history.

(56) References Cited

U.S. PATENT DOCUMENTS

| | | | | |
|---|---|---|---|---|
| 4,147,794 A | 4/1979 | Turner | | |
| 5,284,958 A | 2/1994 | Mizukawa | | |
| 11,643,668 B2 * | 5/2023 | Townes | C12N 9/22 | 424/93.21 |
| 2006/0089316 A1 | 4/2006 | Brown et al. | | |

FOREIGN PATENT DOCUMENTS

| | | | | |
|---|---|---|---|---|
| CN | 1646691 A | 7/2005 | | |
| CN | 101595105 A | 12/2009 | | |
| CN | 104540948 A | 4/2015 | | |
| EP | 2836595 A2 * | 2/2015 | A61K 31/713 | |
| WO | 2006/078942 A2 | 7/2006 | | |
| WO | 2008/074835 A1 | 6/2008 | | |
| WO | 2014/018570 A1 | 1/2014 | | |
| WO | 2015/112902 A2 | 7/2015 | | |
| WO | 2016/037931 A1 | 3/2016 | | |
| WO | 2018/204762 A1 | 11/2018 | | |
| WO | 2024/086695 A2 | 4/2024 | | |

OTHER PUBLICATIONS

Whatley SD, et. al. Am J Hum Genet. Sep. 2008;83(3):408-14 (Year: 2008).*
Balwani M, et. al. Mol Med. Apr. 30, 2013;19(1):26-35 (Year: 2013).*
Nakajima O, et. al. EMBO J. Nov. 15, 1999;18(22):6282-9 (Year: 1999).*
Schoenhaut DS, et. al. Gene. 1986;48(1):55-63 (Year: 1986).*
Harms DW, et. al. Curr Protoc Hum Genet. Oct. 1, 2014;83:15.7. 1-27 (Year: 2014).*
Dow LE, et. al. Nat Protoc. Feb. 2, 2012;7(2):374-93 (Year: 2012).*
Buchberg, AM, et. al. Genetics, vol. 122, Issue 1, May 1, 1989, pp. 153-161 (Year: 1989).*
Dow LE, et. al. PLoS One. Apr. 17, 2014;9(4):e95236 (Year: 2014).*
GenBank. Accession: AK165257; Oct. 6, 2010 (Year: 2010).*

(Continued)

*Primary Examiner* — Marcia S Noble
*Assistant Examiner* — Zanna Maria Beharry
(74) *Attorney, Agent, or Firm* — McCarter & English, LLP; Michael J. DeGrazia

(57) ABSTRACT

Described herein is a compound of Formula I or a pharmaceutically acceptable salt thereof: wherein Ring A $R^1$, $R^2$, a, b, and n are as defined herein. Also described is a method of treating a subject having a disorder in need of treatment, comprising inhibiting aminolevulinic acid synthase 2 (ALAS2) in the subject by administering a compound of Formula (I) or a pharmaceutically acceptable salt thereof. Disorders that are of particular interest are blood disorders, such as porphyria and anemia.

(I)

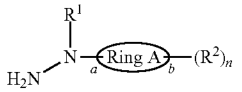

15 Claims, 8 Drawing Sheets

Specification includes a Sequence Listing.

(56) References Cited

OTHER PUBLICATIONS

Fratz, Erica Jean. Exploration of mutations in erythroid 5-aminolevulinate synthase that lead to increased porphyrin synthesis. University of South Florida, 2014 (Year: 2014).*
Bishop, David F., et al. Molecular medicine 17 (2011): 748-756 (Year: 2011).*
To-Figueras, Jordi, et al. Blood, The Journal of the American Society of Hematology 118.6 (2011): 1443-1451 (Year: 2011).*
Fratz, Erica J., et al. Biochemistry 54.36 (2015): 5617-5631 (Year: 2015).*
Ducamp, Sarah, et al. Human molecular genetics 22.7 (2013): 1280-1288 (Year: 2013).*
Fratz, Erica J., et. al. PLoS One 9.4 (2014): e93078 (Year: 2014).*
Adembri et al., Thermal behaviour of 3-phenyl-1,2,4-oxadiazol-5-ylhydrazines. Journal of the Chemical Society, Perkin Transactions 1. 1981;1981;1703-1706.
Coumar et al., Structure-based drug design of novel Aurora kinase A inhibitors: structural basis for potency and specificity. J Med Chem. Feb. 26, 2009;52(4):1050-62.
Ege et al., Reaktionen mit Diazoazolen, VII. 3H-Azolo-1,2,4-triazole durch 1,8-bzw. 1,12-Elektrocyclisierungen von 3H-Pyrazol-3-on-bzw. 3H-Indazol-3-on-(diorganylmethylen)hydrazonen. European Journal of Inorganic Chemistry. 1984;117(5):1726-1747.
Elnagdi et al., The reaction of nitriles with mercaptoacetic acid. A new synthesis of thiazole derivatives. Journal of Heterocyclic Chemistry. Aug. 1981;18(5):877-879.
Gudzera et al., Discovery of potent anti-tuberculosis agents targeting leucyl-tRNA synthetase. Bioorg Med Chem. Mar. 1, 2016;24(5):1023-31.
Matsumura et al., Studies of Nitriles. VIII. Reactions of N-Acyl Derivatives of 2-Amino-3,3-dichloroacrylonitrile (ADAN) with Amines. (1). A New Synthesis of 2-Substituted-5-(substituted amino) oxazole-4-carbonitriles and-4-N-acylcarboxamides. Chemical and Pharmaceutical Bulletin. May 25, 1976;24(5):924-940.
Mokrushin et al., Synthesis and properties of analogs of 5 (or 4)-aminoimidazole-4 (or 5)-carboxamide (AICA) and purines. 13. Synthesis of 5 (or 4)-hydrazinoimidazqles and their derivatives. Chemistry of Heterocyclic Compounds. Nov. 1, 1983;19(11):1235-1238.
Pandey et al., Synthesis, Structures, and Fungitoxicity of Novel Organophosphorus Compounds. Phosphorus, Sulfur, and Silicon and the Related Elements. 2012;187(11):1401-1408.
Prijs et al., Uber Derivate des 5-Amino-thiazols. II. Helvetica Chimica Acta. Dec. 1, 1952;35(24):187-195.
Sayed, Synthesis of novel thiadiazoles and bis-thiadiazoles from carbonothioic dihydrazide. Tetrahedron Letters. Aug. 25, 2010;51(34):4490-4493.
Shafiee et al., 1,2,4-Triazines. VII†. 1,3,4-thiadiazolo[2,3-c]-as-triazines and 2-pyrazolyl-1,3,4-thiadiazoles. Journal of Heterocyclic Chemistry. 1974;13:117-121.
Sujatha et al., Novel one-pot expeditious synthesis of 2,4-disubstituted thiazoles through a three-component reaction under solvent free conditions. Synthetic Communications. 2018;48(3):302-308.
Tobin et al., The mechanism of bromination of heterocyclic hydrazones. syn-anti-Isomerisation of 5-(arymethylenehydrazino)-1- and -2-benzyltetrazoles. Journal of the Chemical Society B: Physical Organic. 1971;2198-2202.
Turner et al., Antihypertensive thiadiazoles. 1. Synthesis of some 2-aryl-5-hydrazino-1,3,4-thiadiazoles with vasodilator activity. J Med Chem. May 1988;31(5):902-6.
Yamazaki et al., Design, synthesis and biological activity of novel non-peptidyl endothelin converting enzyme Inhibitors, 1-phenyl-tetrazole-formazan analogues. Bioorg Med Chem Lett. May 6, 2002;12(9):1275-8.
Invitation to Pay Additional Fees for Application No. PCT/US2020/036424, dated Nov. 6, 2020, 19 pages.
International Search Report and Written Opinion for Application No. PCT/US2020/036424, dated Jan. 27, 2021, 26 pages.
Bishop et al., Molecular expression and characterization of erythroid-specific 5-aminolevulinate synthase gain-of-function mutations causing X-linked protoporphyria. Mol Med. Mar. 5, 2013;19(1):18-25.
Ma et al., CRISPR/Cas9-mediated targeting of the Rosa26 locus produces Cre reporter rat strains for monitoring Cre-loxP-mediated lineage tracing. FEBS J. Oct. 2017;284(19):3262-3277.
Prades et al., A new mutation of the ALAS2 gene in a large family with X-linked sideroblastic anemia. Hum Genet. Apr. 1995;95(4):424-8.
GenBank Accession No. AK002642, Mus musculus adult male kidney cDNA, RIKEN full-length enriched library, clone:0610016020, product: aminolevulinic acid synthase 2, erythroid, full insert sequence. 8 pages, Oct. 6, 2010.
GenBank Accession No. M15268, Mouse 5-aminolevulinic acid synthase mRNA, 3' 3nd. 3 pages, Apr. 27, 1993.
UniProt Accession No. A0A5N9C8E6, Biotin/lipoyl-binding protein. 1 page, Feb. 26, 2020.
UniProt Accession No. A0A7K1LDD8, NADH-quinone oxidoruductase subunit C. 1 page, Apr. 7, 2021.
International Search Report and Written Opinion for Application No. PCT/US2023/077268, dated May 3, 2024, 14 pages.
U.S. Appl. No. 19/121,224, filed Apr. 15, 2025.

* cited by examiner

A
Relative abundance
0 0.01 0.02 0.03 0.04 0.05 0.06
12C PPIX
PPIX 13C1
PPIX 13C2
PPIX 13C3
PPIX 13C4
PPIX 13C5
PPIX 13C6
PPIX 13C7
PPIX 13C8
Time
B
Mass isotopomer distribution analysis demonstrates ALAS2 is the rate-limiting step in PPIX generation
%13C ALA
ALA% Measured
ALA% Predicted via PPIX
Time (min)
-100 0 100 200 300 400
20 40 60 80 100
13C-glycine incorporation into 13C-ALA and 13C-PPIX in Epo-induced TF-1 cells with FECH knocked down

```
10         20         30         40         50
MVTAAMLLQC CPVLARGPTS LLGKVVKTHQ FLFGIGRCPI LATQGPNCSQ
        60         70         80         90        100
IHLKATKAGG DSPSWAKGHC PFMLSELQDG KSKIVQKAAP EVQEDVKAFK
       110        120        130        140        150
TDLPSSLVSV SLRKPFSGPQ EQEQISGKVT HLIQNNMPGN YVFSYDQFFR
       160        170        180        190        200
DKIMEKKQDH TYRVFKTVNR WADAYPFAQH FSEASVASKD VSVWCSNDYL
       210        220        230        240        250
GMSRHPQVLQ ATQETLQRHG AGAGGTRNIS GTSKFHVELE QELAELHQKD
       260        270        280        290        300
SALLFSSCFV ANDSTLFTLA KILPGCEIYS DAGNHASMIQ GIRNSGAAKF
       310        320        330        340        350
VFRHNDPDHL KKLLEKSNPK IPKIVAFETV HSMDGAICPL EELCDVSHQY
       360        370        380        390        400
GALTFVDEVH AVGLYGSRGA GIGERDGIMH KIDIISGTLG KAFGCVGGYI
       410        420        430        440        450
ASTRDLVDMV RSYAAGFIFT TSLPPMVLSG ALESVRLLKG EEGQALRRAH
       460        470        480        490        500
QRNVKHMRQL LMDRGLPVIP CPSHIIPIRV GNAALNSKLC DLLLSKHGIY
       510        520        530        540        550
VQAINYPTVP RGEELLRLAP SPHHSPQMME DFVEKLLLAW TAVGLPLQDV
       560        570        580
SVAACNFCRR PVHFELMSEW ERSYFGNMGP QYVTTYA
```

METHODS OF TREATMENT WITH AMINOLEVULINIC ACID SYNTHASE 2 (ALAS2) MODULATORS

REFERENCE TO RELATED APPLICATIONS

This application is a 35 U.S.C. § 371 national stage filing of International Application No. PCT/US2020/036424, filed on Jun. 5, 2020 which in turn claims the benefit of U.S. Provisional Application No. 62/858,699, filed Jun. 7, 2019 and U.S. Provisional Application No. 62/893,942, filed Aug. 30, 2019 the entire contents of each of which are incorporated herein by reference.

SEQUENCE LISTING

The Sequence Listing associated with this application is filed in electronic format via EFS-Web and is hereby incorporated by reference into the specification. The name of the text file containing the Sequence Listing is 128748_01603_Sequence_Listing. The size of the text file is 11,182 bytes, and the text file was created on Aug. 3, 2022.

BACKGROUND

Heme is an essential molecule to almost all organisms. Heme functions as a prosthetic group on several types of proteins, including cytochromes, catalases, hemoglobin, and myoglobin. Moreover, it has been reported that heme is also involved in numerous regulatory systems in mammals (J. Bio. Chem., 2016, 20516). Production of heme and heme precursors are regulated by 5-aminolevulinatye synthases (e.g. ALAS2). Inhibition of ALAS2 or reduction in ALAS2 protein level may reduce heme pathway flux and suppress the production of toxin metabolites in the heme pathway.

SUMMARY

Inhibition of ALAS2 can reduce levels of metabolites of the heme biosynthesis pathway in animal models (see Example 36). One aspect of the present invention provides compounds of Formula (I) as described herein as inhibitors of ALAS2 (see Example 38). Based on these results, novel ALAS2 inhibitors and methods of treating disorders characterized by accumulation of metabolites of the heme pathway are disclosed.

The present disclosure is directed to a compound of Formula (I) or a pharmaceutically acceptable salt thereof:

(I)

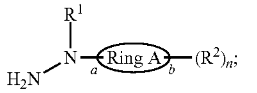

wherein:

Ring A is a 5-membered heteroaryl;

$R^1$ is hydrogen, $C_1$-$C_6$ alkyl, $C_1$-$C_6$ haloalkyl, —$CO_2R^3$, —$C_1$-$C_6$ acyl, or $C_3$-$C_6$ cycloalkyl; wherein each of $C_1$-$C_6$ alkyl, $C_1$-$C_6$ haloalkyl, —$C_1$-$C_6$ acyl, and $C_3$-$C_6$ cycloalkyl is independently substituted with 0-3 instances of halogen or hydroxyl;

$R^2$ is hydrogen, —CN, hydroxyl, $C_1$-$C_6$ alkyl, $C_3$-$C_8$ cycloalkyl, 3-14 membered heterocyclyl, 8-12 membered bicyclic heteroaryl, 5- or 6-membered monocyclic heteroaryl, phenyl, or naphthyl; wherein each of $C_1$-$C_6$ alkyl, $C_3$-$C_8$ cycloalkyl, 3-14 membered heterocyclyl, 8-12 membered bicyclic heteroaryl, 5- or 6-membered monocyclic heteroaryl, phenyl, and naphthyl is independently substituted with 0-4 instances halogen, hydroxyl, $C_1$-$C_6$ alkyl, $C_1$-$C_6$ alkoxy, phenyl, $N(R^a)_2$, or —$CO_2R^b$; each of $R^3$, $R^a$ and $R^b$ is independently $C_1$-$C_6$ alkyl;

n is 0, 1, 2, 3, 4, or 5; and a and b each indicate points of attachment of Ring A.

Another aspect of the invention provides methods of treating a subject in need of treatment of a disorder treatable by inhibiting aminolevulinic acid synthase (ALAS2), the method comprising administering to the subject a compound of Formula (I) or a pharmaceutically acceptable salt thereof.

A further aspect of the invention provides a mouse model of human XLP (X-linked dominant protoporphyria), which may be useful, among others, for testing efficacy of candidate compounds and effective doses thereof for treating XLP.

Figure 1:
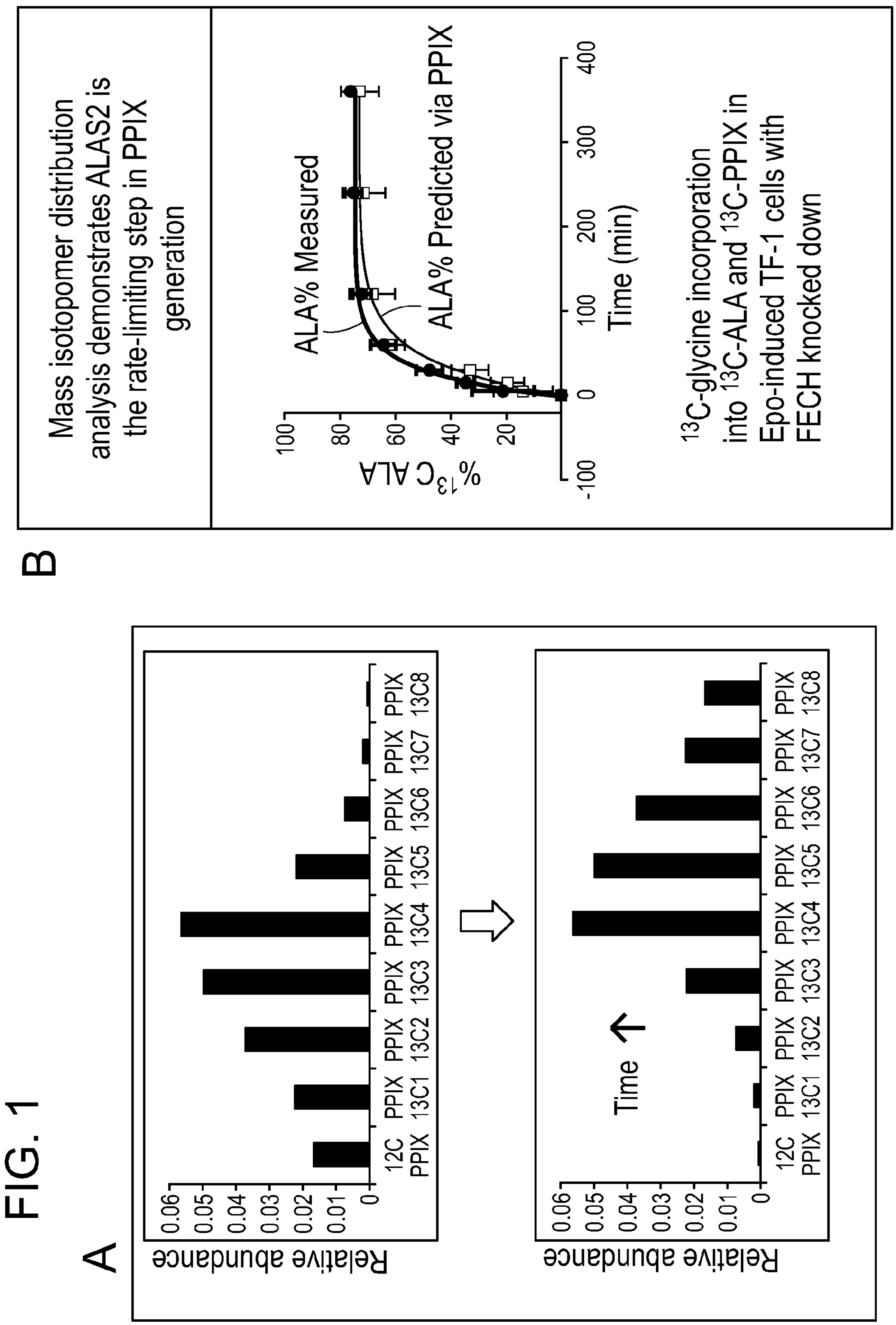
FIGS. 1A and B depict that ALAS2 is the rate limiting step in PPIX accumulation. Mass isotope distribution was used to empirically determine ALAS2 was the rate limiting step in PPIX accumulation in an EPP cell model using $^{13}C_2$-glycine (See Example 36.1). PPIX is a polymer of ALA (product of ALAS2). One PPIX molecule is derived from 8 molecules of ALA. Thus, when $^{13}C_2$-glycine was introduced to the cells, the pool of PPIX generated would be composed of molecules containing different number of $^{13}C$ carbon, ranging from 0 to 8. At earlier time points, since the % of $^{13}C$-ALA was low, the isotopomer distribution trended to have PPIX molecules carrying lower number of labeled carbons. % $^{13}C$-ALA increased as labeling time increased, leading to a shift in the isotopomer distribution to have PPIX molecules with more labeled carbons. Since PPIX isotopomer distribution was mathematically defined by % $^{13}C$-ALA, by directly measuring $^{13}C$-labeled PPIXs and their mass distribution, one could predict what the % ALA should have been at each time point. At the same time, the actual % ALA in cells at each time point was also measured directly by LC-MS. As shown in the diagram on the right, these two curves were statistically identical, indicating there was no slow step between ALA and PPIX and thus demonstrating ALAS2 was the rate limiting step in the production of PPIX in EPP cells.
Figure 2:
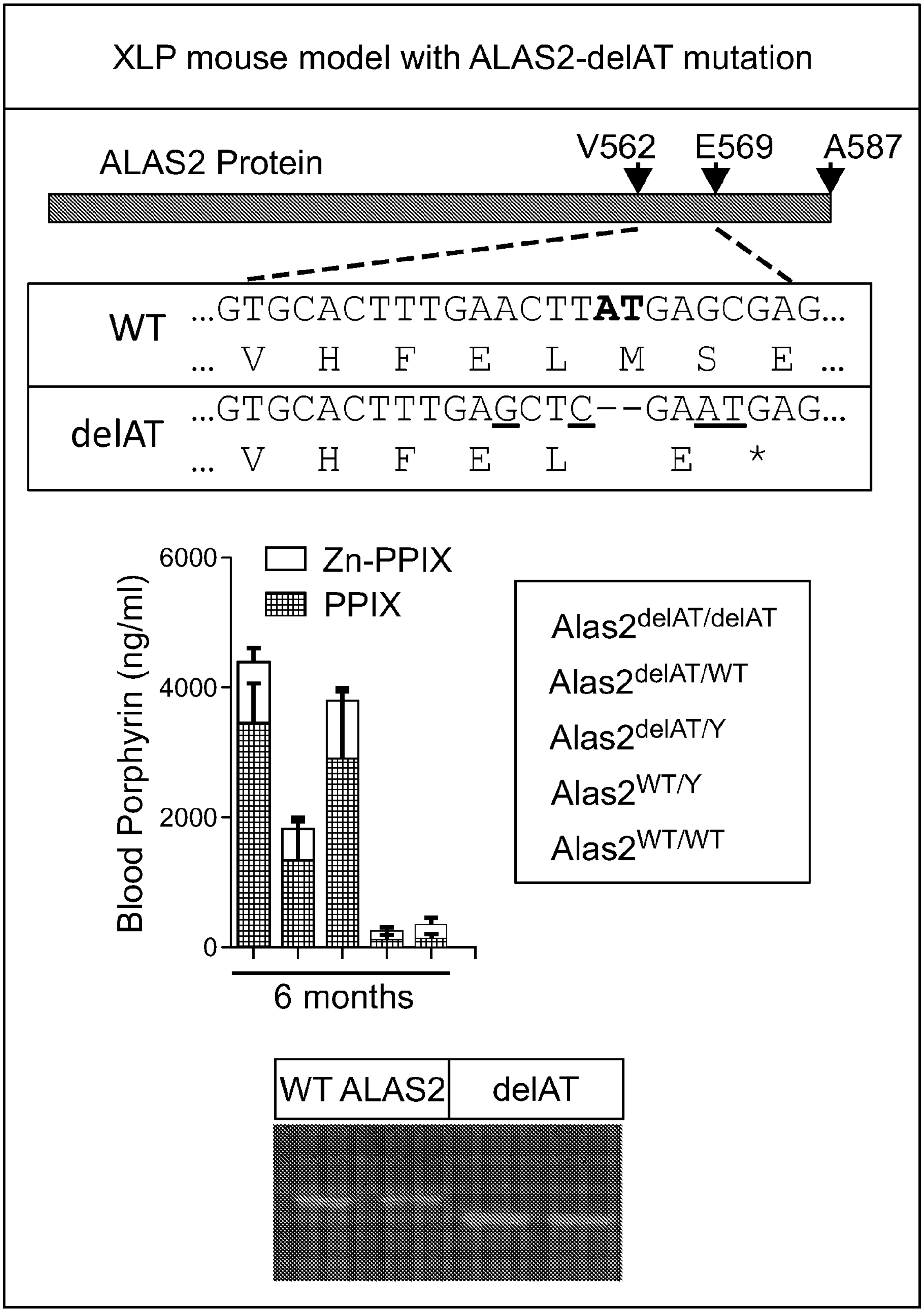
FIG. 2 depicts the mouse models for ALAS2 target validation to treat erythroid porphyria. XLP mouse model with ALAS2-delAT mutation recapitulates human disease markers. To create an XLP mouse model, an ALAS2 C-terminal deletion (SEQ ID NO:1 and SEQ ID NO:2) was provided in mice similar to that in human XLP disease by knocking in nucleotide deletions and mutation via CRISPR/CAS9 (Example 36.2). Indeed, these mutations resulted in a shorter form of the protein compared to full-length ALAS2 as visualized by western blot. Significantly, these mice showed elevated level of blood PPIX and Zn-PPIX, two characteristic disease markers seen in human XLP patients.
Figure 3:
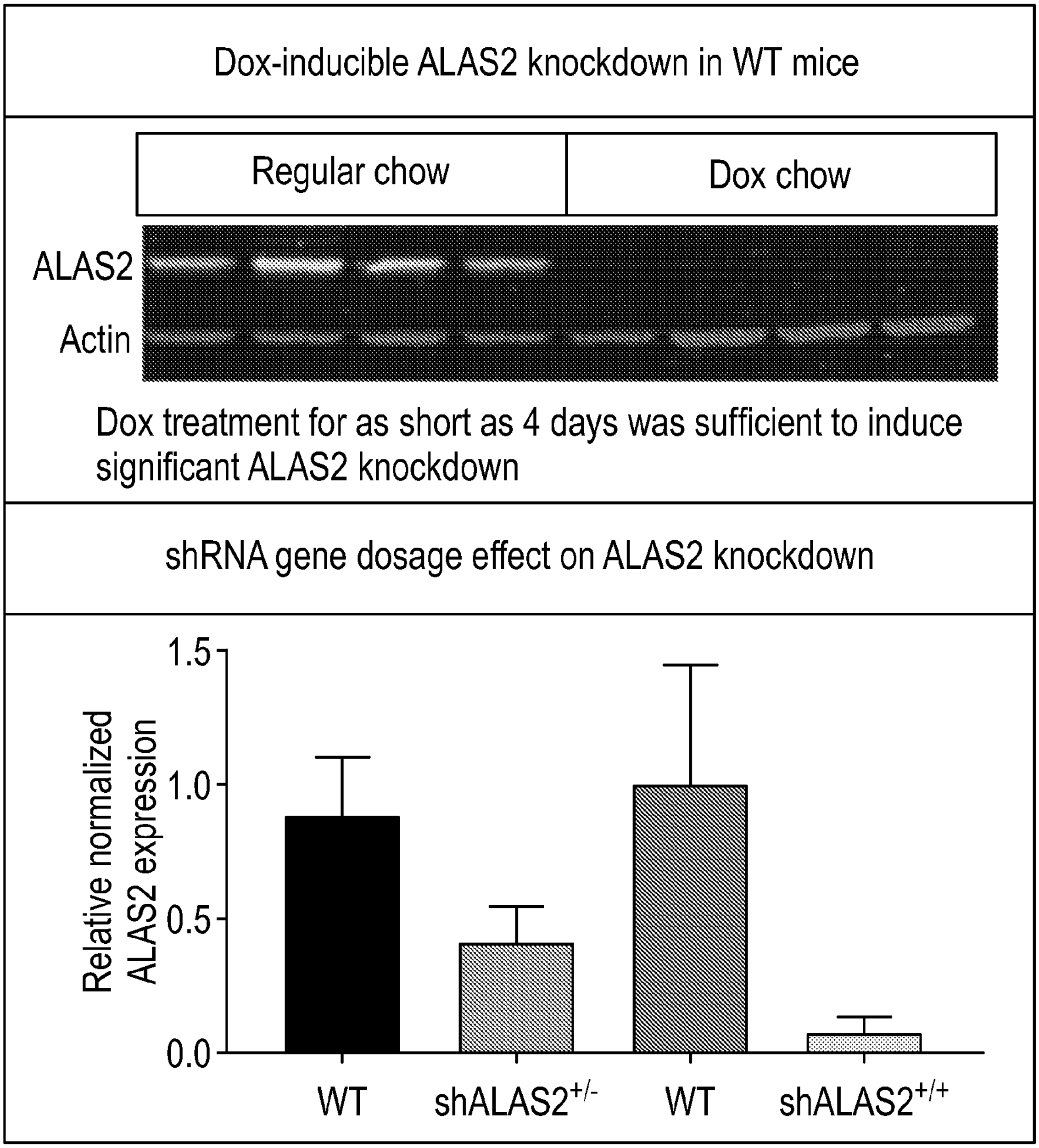
FIG. 3 depicts mouse models for ALAS2 target validation to treat erythroid porphyria. ALAS2 protein level could be knocked down by shRNA in mice. The expression cassettes for rtTA and a shRNA against mouse ALAS2 were introduced into C57B6 (Example 36.3). Homozygous $rtTa^{+/+}$/$ShALAS2^{+/+}$ mice were tested and showed that ALAS2 could be significantly knocked down upon doxycycline treatment for as short as 4 days. Heterozygous $rtTA^{+/+}$/ shALAS2$^{+/-}$ mice were tested to confirm if doxycycline treatment of these mice would have lesser extent of protein knockdown as these mice only carried one copy of the shRNA expression cassette. Indeed, quantification of ALAS2 protein blot showed that about 50% of ALAS2 was knocked down in heterozygous rtTA$^{+/-}$/shALAS2$^{+/-}$ mice fed with doxycycline-containing chow for 16 days.
Figure 4:
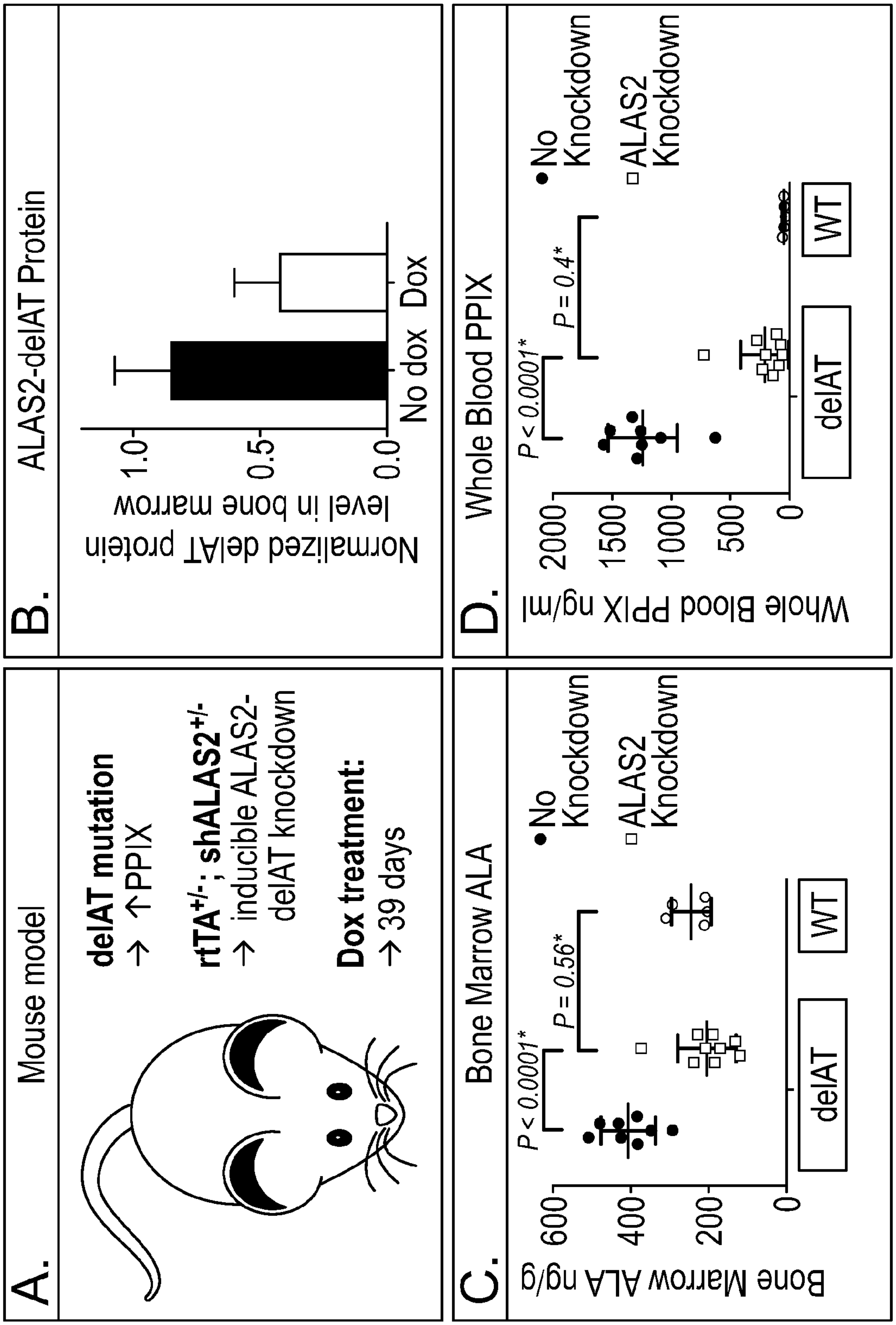

FIG. 4 depicts genetic validation of ALAS2 inhibition strategy. The delAT mice carrying one copy of an ALAS2 shRNA cassette was tested to validate ALAS2 inhibition strategy in treating XLP (Example 36.4). These mice were fed with doxycycline to induce the expression of an shRNA against ALAS2. Consistent with previous results (see FIG. 3), mice with one copy of the shALAS2 gene, upon doxycycline treatment, had ALAS2-delAT protein level reduced by about 50%. This reduction in ALAS2-delAT protein level was sufficient to reduce ALA in the bone marrow to WT level. Significantly, blood PPIX level was normalized to a level statistically indistinguishable from WT mice. Thus, the data indicated that inhibition of ALAS2 is a valid strategy to treat erythroporphyrias.

Figure 5:
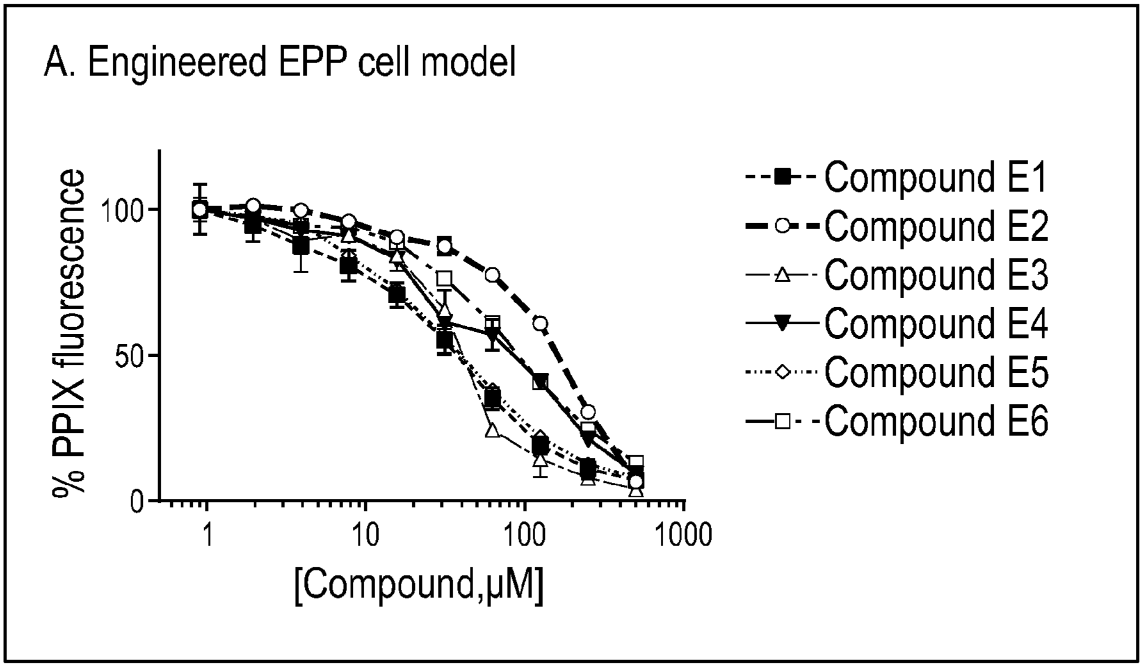
Figure 5:
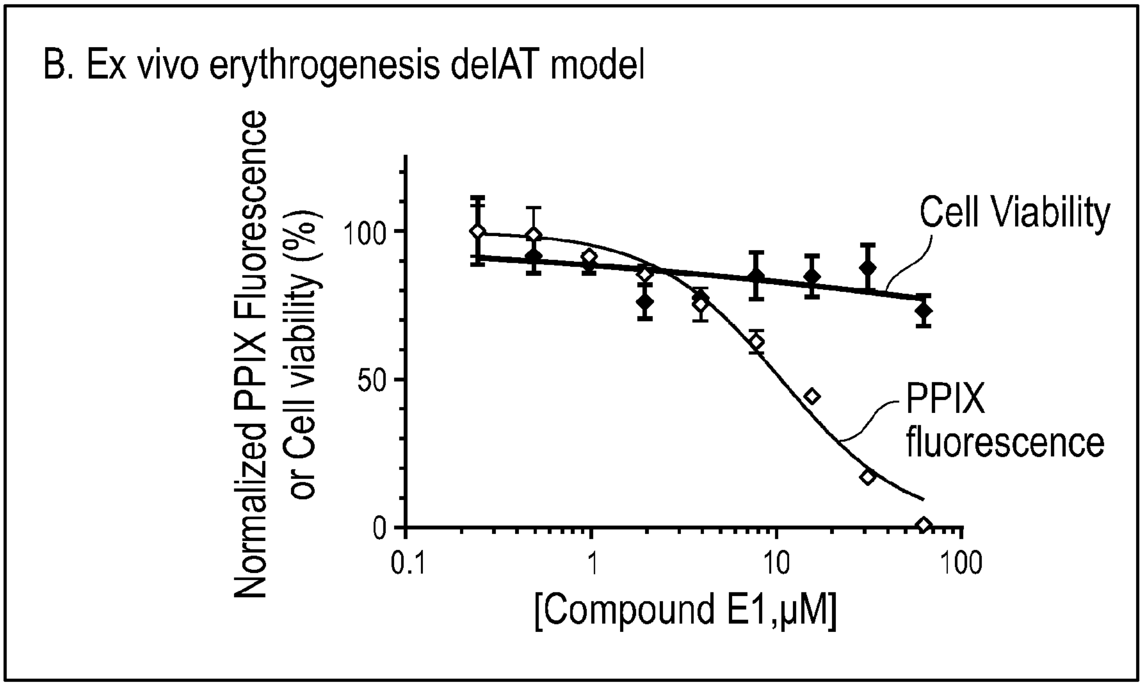

FIG. 5 depicts the exemplified compounds that inhibited ALAS2 in erythroporphyria cell models in vitro. The exemplified compounds blocked PPIX production in an engineered cell model mimicking EPP (Example 36.5). The exemplified compounds dose-dependently reduced PPIX fluorescence without affecting cell viability at concentrations tested. Compound E1 was also tested in an in vitro XLP cell model. Compound E1 blocked PPIX production in ex vivo differentiating erythroprogenitor cells isolated from XLP mice with ALAS2-delAT mutation. Compound E1 dose-dependently reduced PPIX fluorescence without affecting cell viability at the concentrations tested. Thus, the data suggest the compounds as provided herein can be used to treat erythroid porphyrias by normalizing PPIX level.

Figure 6:
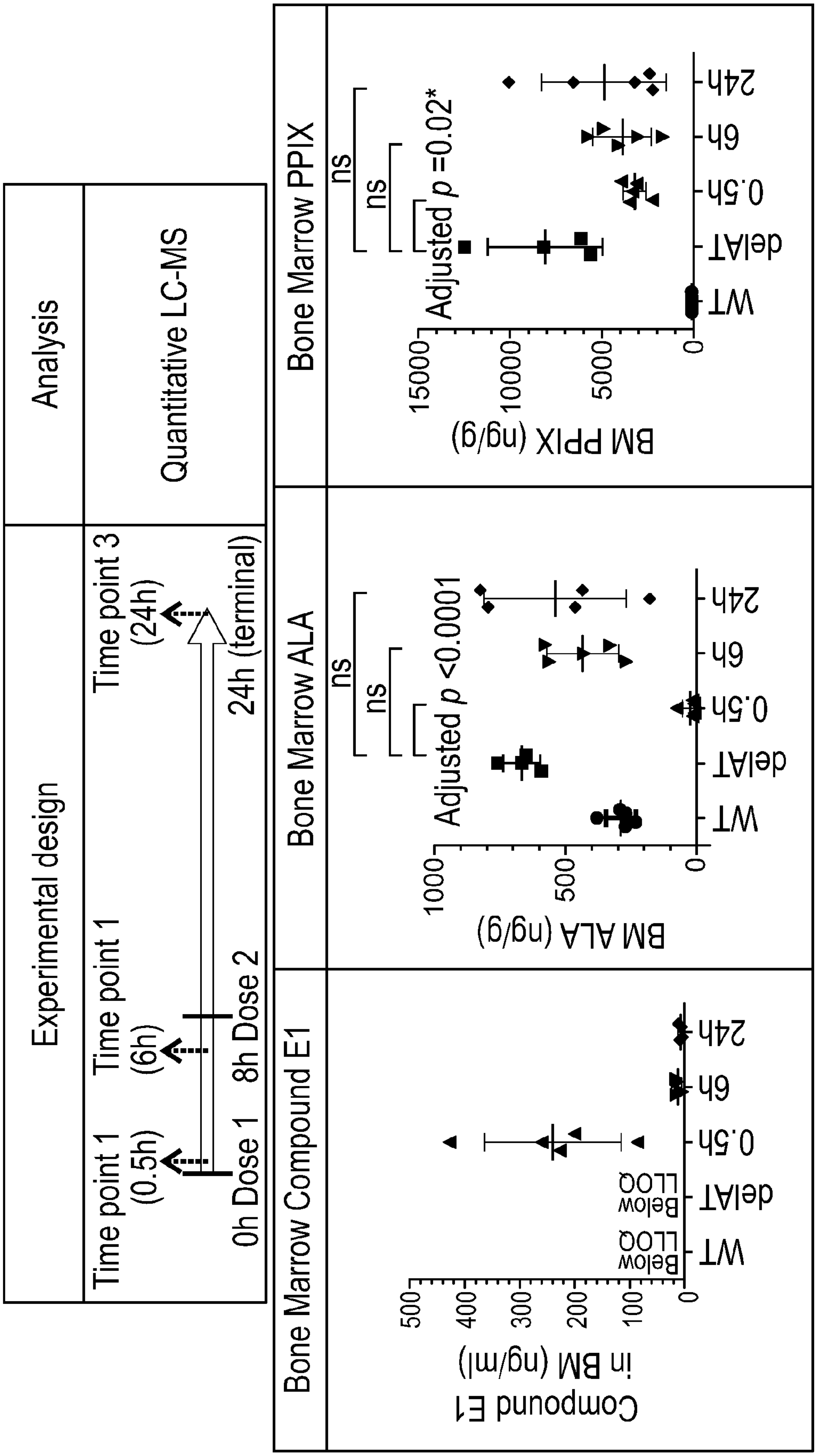

FIG. 6 depicts pharmacological proof of mechanism of ALAS2 inhibition strategy in vivo (Example 36.6). Compound E1 potently inhibited ALAS2 with delAT mutation in the XLP mouse model leading to reduction in ALA and PPIX in the bone marrow. Compound E1 was dosed in the delAT mice by oral gavage and observed compound accumulation in the bone marrow compartment and potent reduction in bone marrow ALA 30 mins after dosing. Consequently, a reduction of total bone marrow PPIX was also observed. Thus, the data provided pharmacological proof of mechanism of ALAS2 inhibition strategy in vivo to treat a erythroid porphyria.

Figure 7:
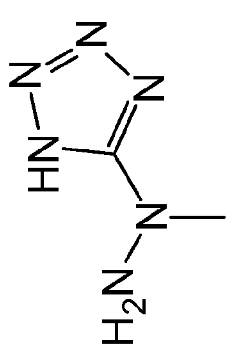
Figure 7:
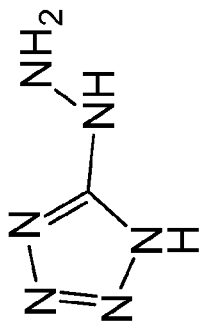
Figure 7:
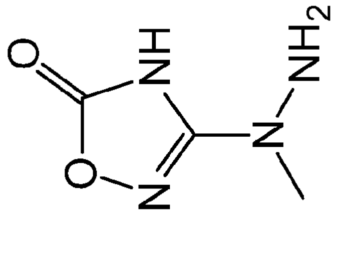
Figure 7:
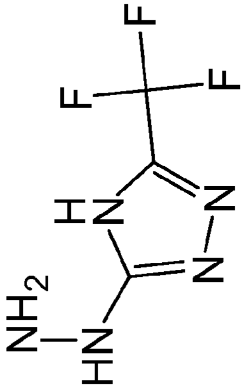
Figure 7:
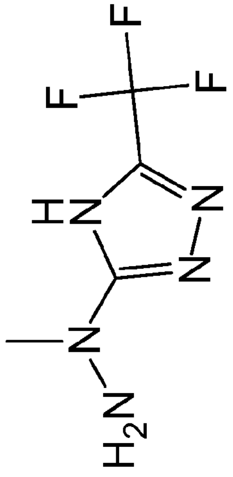
Figure 7:
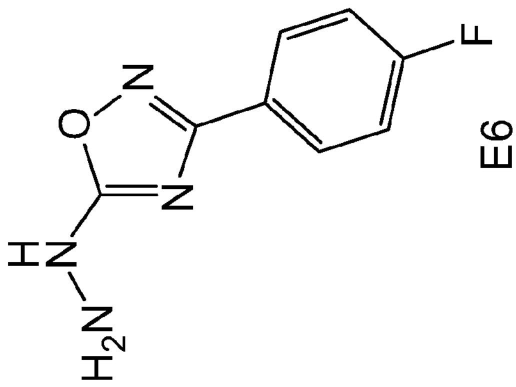

FIG. 7 depicts the structures of the exemplified compounds tested in Example 36, FIGS. 5 and 6.

FIG. 8 depicts the sequence of ALAS2 (SEQ ID NO:3).

DETAILED DESCRIPTION

Compounds

Described herein are compounds that are useful for treating various diseases, disorders and medical conditions, including those characterized by defects in the heme pathway that lead to accumulation of one or more metabolites of the pathway. Inhibition of the enzyme in the pathway, namely ALAS2, as shown in Example 36, may reduce the level of accumulated metabolites, thereby alleviating the symptoms of the disorder. Examples of disorders treatable with the compounds of the invention are but not limited to X-linked protoporphyria, erythropoietic protoporphyria, congenital erythropoietic protoporphyria, myelodysplastic syndrome associated with isolated del(5q) (Del5q MDS), and Diamond-Blackfan anemia (DBA).

In a first embodiment, a compound of the present invention is a compound of Formula (I) or a pharmaceutically acceptable salt thereof as described in the summary.

In a second embodiment, in a compound of Formula (I) or a pharmaceutically acceptable salt thereof, Ring A is a 5-membered heteroaryl containing 1-4 instances of N; wherein the remaining variables are as defined in the first embodiment.

In a third embodiment, in a compound of Formula (I) or a pharmaceutically acceptable salt thereof, Ring A is a 5-membered heteroaryl containing 1-2 instances of N and one instance of S or O; wherein the remaining variables are as defined in the first or second embodiments.

In a fourth embodiment, in a compound of Formula (I) or a pharmaceutically acceptable salt thereof, Ring A is 1,2,4-oxadiazolyl, pyrazolyl, 1,2,4-triazolyl, tetrazolyl, 1,2,3-thiadiazolyl, thiazolyl, 1,3,4-thiadiazolyl, 1,2,4-oxadiazolyl-5 (4H)-one, 1,2,3-triazolyl, 1,2,4-triazolyl-3-one, $^{1}$H-imidazolyl, 1,3,4-oxadiazolyl, or oxazolyl; wherein the remaining variables are as defined in the first, second, or third embodiments.

In a fifth embodiment, in a compound of Formula (I) or a pharmaceutically acceptable salt thereof, Ring A is selected from one of the following:

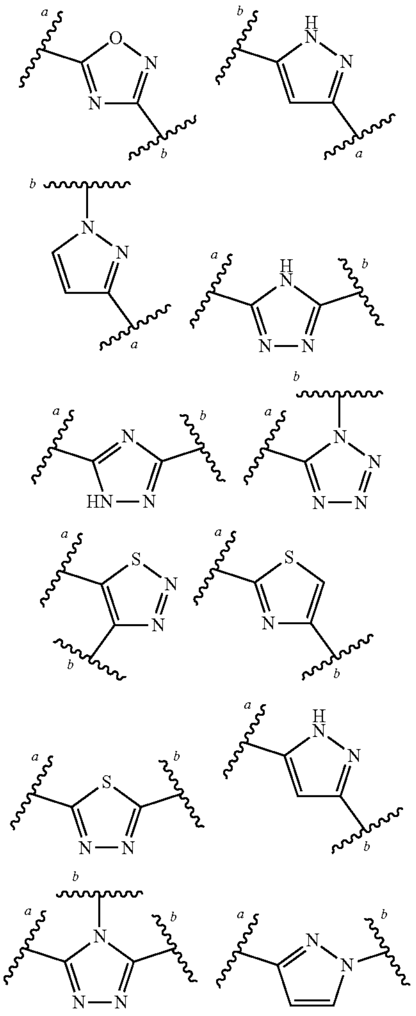

-continued

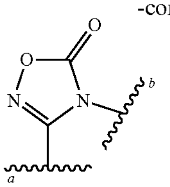

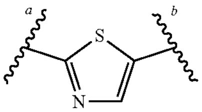

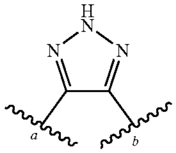

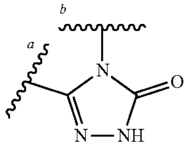

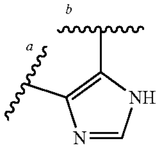

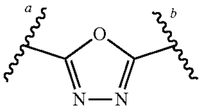

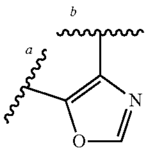

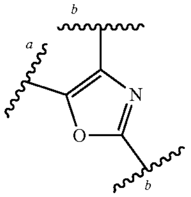

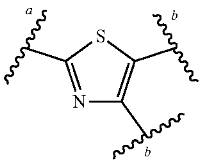

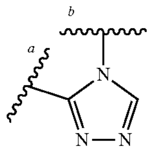 ;

wherein the remaining variables are as defined in the first, second, third, or fourth embodiments.

In a sixth embodiment, in a compound of Formula (I) or a pharmaceutically acceptable salt thereof, $R^1$ is hydrogen or $C_1$-$C_6$ alkyl; wherein the remaining variables are as defined in the first, second, third, fourth, or fifth embodiments.

In a seventh embodiment, in a compound of Formula (I) or a pharmaceutically acceptable salt thereof, $R^1$ is hydrogen, methyl, ethyl, propyl, i-propyl, cyclopropyl, —C(═O)$CF_3$, or —$CH_2CH_2OH$; wherein the remaining variables are as defined in the first, second, third, fourth, or fifth embodiments.

In an eighth embodiment, in a compound of Formula (I) or a pharmaceutically acceptable salt thereof, $R^2$ is hydrogen, —CN, hydroxyl, $C_1$-$C_6$ alkyl, $C_1$-$C_6$ haloalkyl, —$CH_2OCH_3$, —$CH_2$-phenyl, phenyl, o-methylphenyl, p-aminophenyl, p-methoxylphenyl, p-fluorophenyl, naphthalyl, cyclopropyl, —$CO_2H$, or —$CO_2Et$; wherein the remaining variables are as defined in the first, second, third, fourth, fifth, sixth, or seventh embodiments.

In a ninth embodiment, in a compound of Formula (I) or a pharmaceutically acceptable salt thereof, $R^2$ is 5- or 6-membered monocyclic heteroaryl, 8-12 membered bicyclic heteroaryl, or 3-14 membered heterocyclyl; wherein the remaining variables are as defined in the first, second, third, fourth, fifth, sixth, or seventh embodiments.

In a tenth embodiment, in a compound of Formula (I) or a pharmaceutically acceptable salt thereof, $R^2$ is pyridinyl, furanyl, or morpholinyl; wherein the remaining variables are as defined in the first, second, third, fourth, fifth, sixth, seventh, or ninth embodiments.

In an eleventh embodiment, in a compound of Formula (I) or a pharmaceutically acceptable salt thereof, n is 0, 1 or 2; wherein the remaining variables are as defined in the first, second, third, fourth, fifth, sixth, seventh, eighth, ninth, or tenth embodiments.

In a twelfth embodiment, a compound of the present invention or a compound of Formula (I) is compound of Table lor a pharmaceutically acceptable salt thereof:

TABLE 1

Exemplary compounds of Formula (I)

| Cpd Nr | Structure |
|---|---|
| 1 | 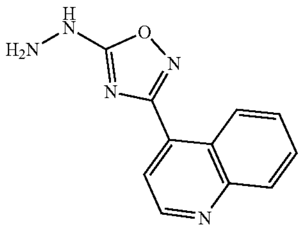 [SMILES: NNc1nc(-c2ccnc3ccccc23)no1] |
| 2 | 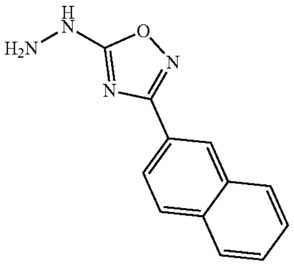 [SMILES: NNc1nc(-c2ccc3ccccc3c2)no1] |
| 3 | 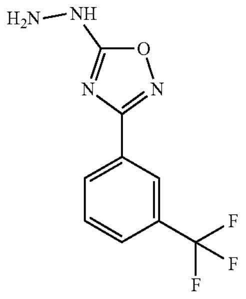 [SMILES: NNc1nc(-c2cccc(C(F)(F)F)c2)no1] |
| 4 | 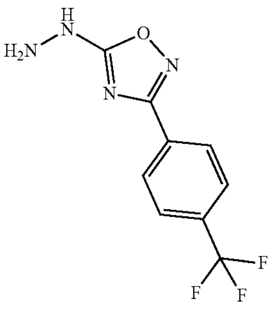 [SMILES: NNc1nc(-c2ccc(C(F)(F)F)cc2)no1] |

TABLE 1-continued
| Exemplary compounds of Formula (I) | |
|---|---|
| Cpd Nr | Structure |
| 5 | 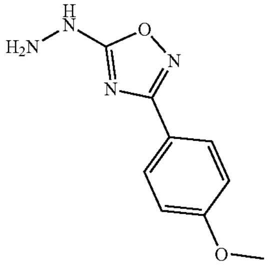 |
| 6 | 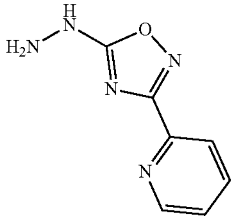 [SMILES: NNc1nc(-c2ccccn2)no1] |
| 7 | 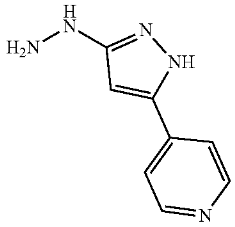 [SMILES: NNc1cc(-c2ccncc2)[nH]n1] |
| 8 | 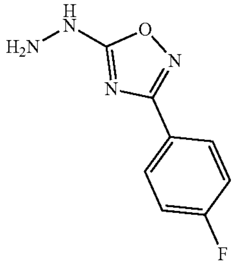 [SMILES: NNc1nc(-c2ccc(F)cc2)no1] |
| 9 | 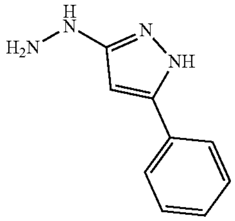 [SMILES: NNc1cc(-c2ccccc2)[nH]n1] |
| 10 | 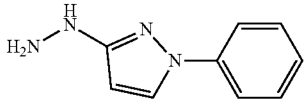 [SMILES: NNc1ccn(-c2ccccc2)n1] |
| 11 | 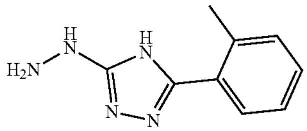 |
TABLE 1-continued
| Exemplary compounds of Formula (I) | |
|---|---|
| Cpd Nr | Structure |
| 12 | 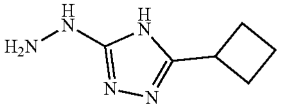 [SMILES: NNc1nnc(C2CCC2)[nH]1] |
| 13 | 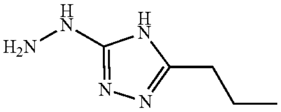 |
| 14 | 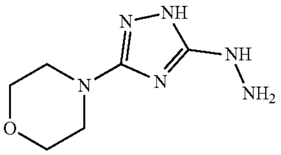 [SMILES: NNc1nc(N2CCOCC2)n[nH]1] |
| 15 | 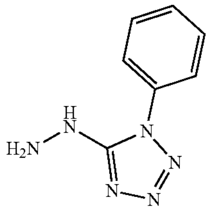 [SMILES: NNc1nnnn1-c1ccccc1] |
| 16 | 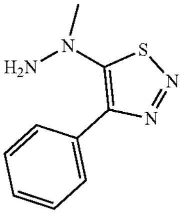 |
| 17 | 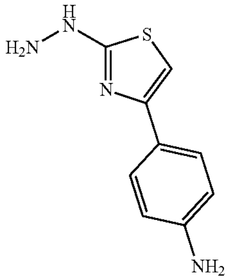 [SMILES: NNc1nc(-c2ccc(N)cc2)cs1] |
| 18 | 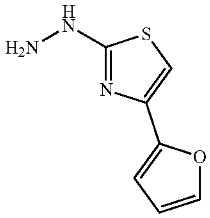 [SMILES: NNc1nc(-c2ccco2)cs1] |

TABLE 1-continued
| Exemplary compounds of Formula (I) | |
|---|---|
| Cpd Nr | Structure |
| 19 | 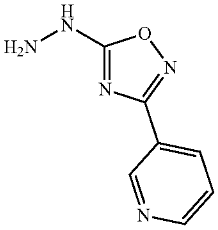 [SMILES: NNc1nc(-c2cccnc2)no1] |
| 20 | 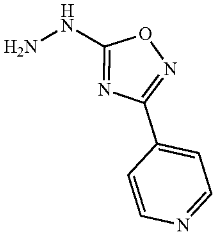 [SMILES: NNc1nc(-c2ccncc2)no1] |
| 21 | 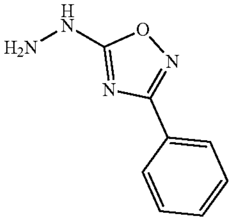 [SMILES: NNc1nc(-c2ccccc2)no1] |
| 22 | 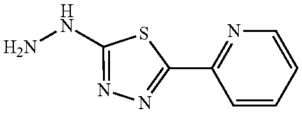 |
| 23 | 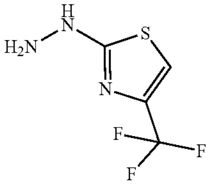 [SMILES: NNc1nc(C(F)(F)F)cs1] |
| 24 | 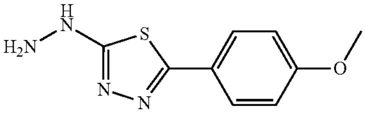 |
| 25 | 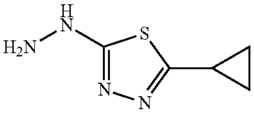 |
| 26 | 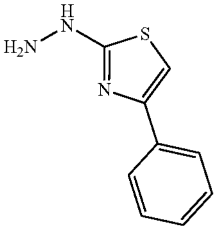 [SMILES: NNc1nc(-c2ccccc2)cs1] |
TABLE 1-continued
| Exemplary compounds of Formula (I) | |
|---|---|
| Cpd Nr | Structure |
| 27 | 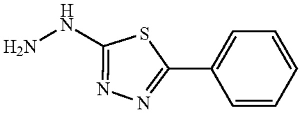 [SMILES: NNc1nnc(-c2ccccc2)s1] |
| 28 | 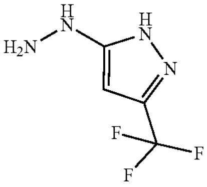 [SMILES: NNc1cc(C(F)(F)F)n[nH]1] |
| 29 | 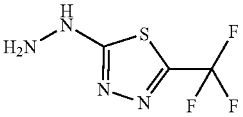 [SMILES: NNc1nnc(C(F)(F)F)s1] |
| 30 | 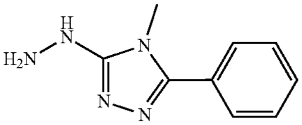 |
| 31 | 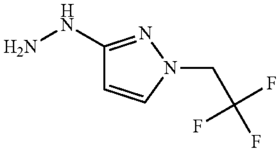 [SMILES: NNc1ccn(CC(F)(F)F)n1] |
| 32 | 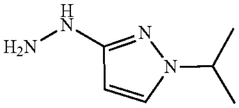 |
| 33 | 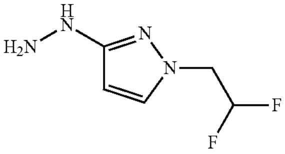 [SMILES: NNc1ccn(CC(F)F)n1] |
| 34 | 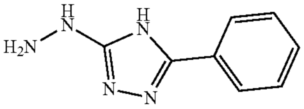 [SMILES: NNc1nnc(-c2ccccc2)[nH]1] |
| 35 | 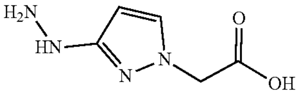 |
| 36 | 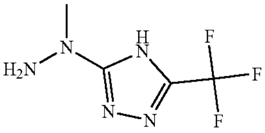 |

TABLE 1-continued
| Exemplary compounds of Formula (I) | |
|---|---|
| Cpd Nr | Structure |
| 37 | 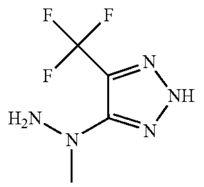 |
| 38 | 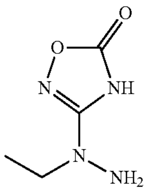 |
| 39 | 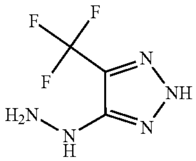 [SMILES: NNc1n[nH]nc1C(F)(F)F] |
| 40 | 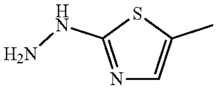 |
| 41 | 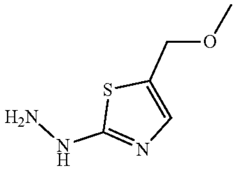 |
| 42 | 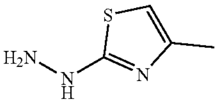 |
| 43 | 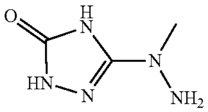 |
| 44 | 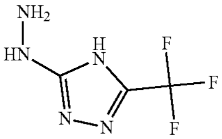 [SMILES: NNc1nnc(C(F)(F)F)[nH]1] |
| 45 | 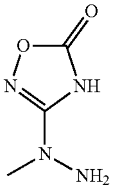 |
TABLE 1-continued
| Exemplary compounds of Formula (I) | |
|---|---|
| Cpd Nr | Structure |
| 46 | 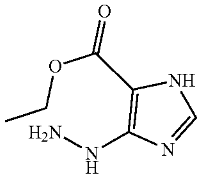 |
| 47 | 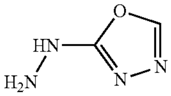 |
| 48 | 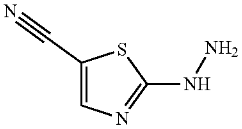 |
| 49 | 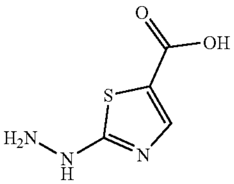 |
| 50 | 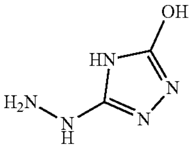 |
| 51 | 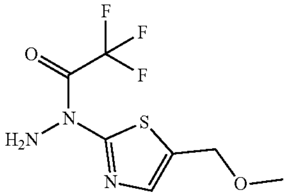 [SMILES: COCc1cnc(N(N)C(=O)C(F)(F)F)s1] |
| 52 | 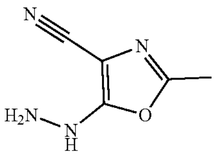 |
| 53 | 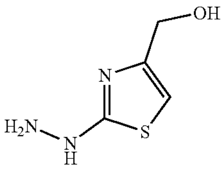 |

TABLE 1-continued

| Exemplary compounds of Formula (I) | |
|---|---|
| Cpd Nr | Structure |
| 54 | 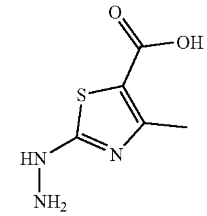 |
| 55 | 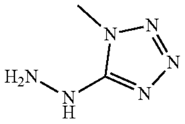 |
| 56 | 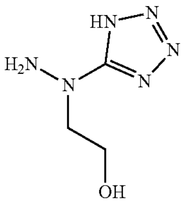 |
| 57 | 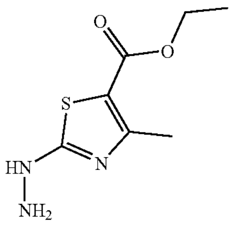 |
| 58 | 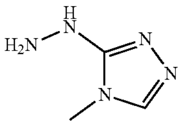 |
| 59 | 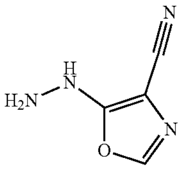 |
| 60 | 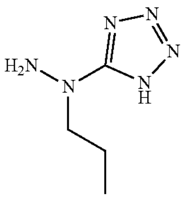 |
| 61 | 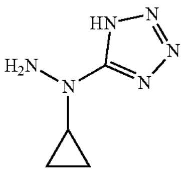 |

TABLE 1-continued

| Exemplary compounds of Formula (I) | |
|---|---|
| Cpd Nr | Structure |
| 62 | 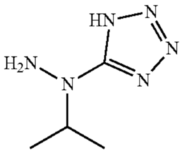 |
| 63 | 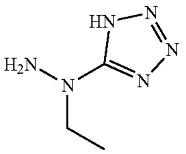 |
| 64 | 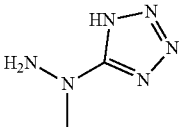 |
| 65 | 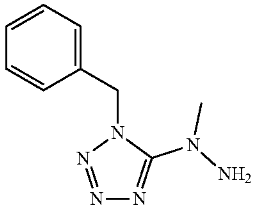 |
| 66 | 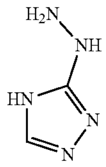 |
| 67 | 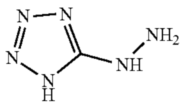 |

The exemplified compounds in Table I were tested in vitro against the wild type ALAS2. As described in Example 38, two concentrations of ALAS2 were used: 5 ug/mL ALAS2 (for the version 1 assay) and 2 ug/mL (for the version 2 assay). "A" refers to an $IC_{50}$ less than 10.0 μM; "B" refers to an $IC_{50}$ from 10.0 μM to 50.0 μM; and "C" refers to an $AC_{50}$ greater than 50.0 μM.

TABLE 2

Biochemical activities of the exemplified compounds in Table 1.

| Compound No. | IC50 (uM) ALAS2 v1; 0 uM PLP | IC50 (uM) ALAS2 v2; 0 uM PLP |
|---|---|---|
| 1. | | A |
| 2. | | A |
| 3. | | C |
| 4. | | B |
| 5. | | B |
| 6. | B | |
| 7. | B | |
| 8. | B | |
| 9. | B | |

TABLE 2-continued

| Biochemical activities of the exemplified compounds in Table 1. | | |
|---|---|---|
| Compound No. | IC50 (uM) ALAS2 v1; 0 uM PLP | IC50 (uM) ALAS2 v2; 0 uM PLP |
| 10. | B | |
| 11. | A | |
| 12. | C | |
| 13. | B | |
| 14. | B | |
| 15. | C | |
| 16. | No Fit | |
| 17. | C | |
| 18. | C | |
| 19. | A | |
| 20. | A | |
| 21. | A | |
| 22. | A | |
| 23. | C | |
| 24. | B | |
| 25. | C | |
| 26. | C | |
| 27. | A | |
| 28. | B | |
| 29. | A | |
| 30. | C | |
| 31. | C | |
| 32. | A | |
| 33. | B | |
| 34. | A | |
| 35. | A | |
| 36. | A | |
| 37. | B | |
| 38. | A | |
| 39. | A | |
| 40. | A | |
| 41. | C | |
| 42. | C | |
| 43. | A | |
| 44. | A | |
| 45. | A | |
| 46. | A | |
| 47. | C | |
| 48. | B | |
| 49. | C | |
| 50. | C | |
| 51. | C | |
| 52. | C | |
| 53. | B | |
| 54. | B | |
| 55. | C | |
| 56. | C | |
| 57. | B | |
| 58. | C | |
| 59. | C | |
| 60. | C | |
| 61. | C | |
| 62. | No Fit | |
| 63. | C | |
| 64. | A | |
| 65. | C | |
| 66. | A | |
| 67. | A | |

The term "alkyl" refers to a radical of a straight-chain or branched saturated hydrocarbon group having from 1 to 12 carbon atoms, e.g., 1 to 6 carbon atoms ("$C_1$-$C_6$ alkyl"). Examples of $C_1$-$C_6$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl).

The term "halo" or "halogen" refers to fluorine, chlorine, bromine, or iodine.

The term "haloalkyl" refers to an alkyl group as defined above, such as a $C_1$-$C_6$ alkyl ("$C_1$-$C_6$ haloalkyl"), wherein one or more of the hydrogen atoms are independently replaced by a halogen, e.g., fluoro, bromo, chloro, or iodo and includes alkyl moieties in which all hydrogens have been replaced by halo (e.g., perfluoroalkyl).

The term "alkoxy" refers to an —O-alkyl radical group, wherein alkyl is as defined above, e.g., with between 1 and 6 carbon atoms ("$C_1$-$C_6$ alkoxy").

The term "acyl" refers to a radical group having the general formula —C(═O)$R^{X1}$, wherein $R^{X1}$ is an alkyl group as defined above.

The term "cycloalkyl" as employed herein includes saturated cyclic, bicyclic, tricyclic, or polycyclic (e.g., a fused, bridged or spiro ring system) hydrocarbon groups having 3 to 14 carbons containing the indicated number of rings and carbon atoms (e.g., a $C_3$-$C_8$ cycloalkyl).

The term "heterocyclyl" or "heterocyclic" refers to a radical of a 3- to 14-membered saturated or unsaturated, and non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl"), and can be saturated or can contain one or more carbon-carbon double bonds. Heterocyclyl polycyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). Exemplary heterocyclyl groups include aziridinyl, oxiranyl, thiiranyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dine, dioxolanyl, oxathiolanyl, dithiolanyl, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, $^1$H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "heteroaryl" refers to a radical of a 5-14 membered monocyclic or polycyclic (e.g., bicyclic, tricyclic, etc.) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continues to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is a monocyclic heteroaryl, such as a 5- or 6-membered monocyclic heteroaryl. Exemplary monocyclic heteroaryl groups include pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, 1,2,4-oxadiazolyl, 1,2,4-triazolyl, tetrazolyl, 1,2,3-thiadiazolyl, 1,3,4-thiadiazolyl, 1,2,4-oxadiazolyl-5(4H)-one, 1,2,3-triazolyl, 1,2,4-triazolyl-3-one, $^1$H-imidazolyl, or 1,3,4-oxadiazolyl etc. In certain embodiments, the heteroaryl is a bicyclic heteroaryl, such as a 8-12 membered bicyclic heteroaryl. Exemplary bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzothiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, etc.

The term "aryl" refers to a radical of a monocyclic or polycyclic (e.g., bicyclic or tricyclic, etc.) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more cycloalkyl or aryl groups. A phenyl substituted with methyl, amine, methoxy, or fluoro is described herein as methylphenyl, aminophenyl, methoxyphenyl, or fluorophenyl, respectively.

The term "fused" referring to a bicyclic, tricyclic or polycyclic ring system as used herein, is a bicyclic, tricyclic or polycyclic ring system wherein at least two rings share two adjacent ring atoms selected from C, N, O and S.

The term "spiro" referring to a bicyclic, tricyclic or polycyclic ring system as used herein, is a bicyclic, tricyclic or polycyclic ring system wherein at least two rings share one ring atom that is selected from C, N, O and S.

The term "bridged" referring to a bicyclic, tricyclic or polycyclic ring system as used herein, is a bicyclic, tricyclic or polycyclic ring system wherein at least two rings are two non-adjacent ring atoms selected from C, N, O and S.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Treatment of Disorders

In another aspect, the present disclosure is directed to a method of treating a subject having a disorder in need of treatment, comprising inhibiting aminolevulinic acid synthase 2 (ALAS2) in the subject by administering a compound of Formula (I) or a pharmaceutically acceptable salt thereof as defined above in the first through twelfth embodiments; use of a compound of Formula (I) or a pharmaceutically acceptable salt thereof as defined above in the first through twelfth embodiments for the manufacture of a medicament for treating a disorder; and a compound of Formula (I) or a pharmaceutically acceptable salt thereof as defined above in the first through twelfth embodiments for use in treating a disorder.

Disorders that can be treated with a compound of Formula (I) or a pharmaceutically acceptable salt thereof are characterized by defects in the heme pathway that lead to accumulation of one or more physiological or non-physiological metabolites of the pathway. Examples of these metabolites of the heme pathway are 5-aminolevulinic acid, δ-aminolevulinic acid (δALA), porphobilinogen (BPG), hydroxymethylbilane (HMB), uroporphyrinogen I, uroporphyrinogen III (UROgen III), coproporphyrinogen I, coproporphyrinogen III (CPgenIII), protoporphyrinogen IX, uroporphyrin I, coproporphyrin I, heme, and protoporphyrin IX (PPIX).

The defects in the heme pathway are attributed to the deregulation of one or more enzymes in the heme pathway. The enzymes in the heme pathway include 8-aminolevulinic acid synthase (ALAS2), ALA dehydratase (ALAD), hydroxymethylbilane synthase (HMBS), uroporphyrinogen III synthase (UROS), uroporphyrinogen decarboxylase (UROD), coproporphyrinogen oxidase (CPOX), protoporphyrinogen oxidase (PPIOX), and ferrochelatase (FECH). Examples of metabolites of the heme pathway are 5-aminolevulinic acid, δ-aminolevulinic acid (δALA), porphobilinogen (BPG), hydroxymethylbilane (HMB), uroporphyrinogen I, uroporphyrinogen III (UROgen III), coproporphyrinogen I, coproporphyrinogen III (CPgenIII), protoporphyrinogen IX, uroporphyrin I, coproporphyrin I, heme, and protoporphyrin IX (PPIX).

In one embodiment, the disorder treated in a method of invention is associated with deregulated wild-type ALAS2. In some embodiments, the deregulated ALAS2 is associated with an increase in the amount of ALAS2, and/or at least one metabolite from the heme pathway as described above, for example at least one of uroporphyrin I, coproporphyrin I, heme, and protoporphyrin IX (PPIX).

Alternatively, the deregulated ALAS2 is a mutated ALAS2 that is associated with increased ALAS2 activity. To determine if a subject's disorder is associated with a wild-type ALAS2 or a mutated ALAS2 with increased activity, a method of the invention further comprises a step of determining the nucleic acid and/or amino acid sequence the subject's ALAS2 and comparing to the wild-type enzyme.

Additional disorders that can be treated with a compound of Formula (I) or a pharmaceutically acceptable salt thereof include disorders that are caused by mutations in one or more enzymes in the heme pathway (see examples of the enzymes given above). In one embodiment, the mutated enzyme is ALAS2. In another embodiment, the mutated enzyme is FECH. In yet another embodiment, the mutated enzyme is UROS. One class of such disorders are blood disorders known as "porphyria", "erythroporphyria" or "erythoid porphyria". Porphyrias are characterized by acute photosensitivity resulting in painful attacks, due to pathologically elevated or accumulated erythrocyte porphyrins. At least three subtypes of porphyria are known: X-linked protoporphyria, erythropoietic protoporphyria, and congenital erythropoietic porphyria.

"X-linked proporphyria" (XPP) is caused by gain-of-function mutations in δ-aminolevulinic acid synthase isoform 2 ALAS2 (first enzyme of the heme pathway). These mutations increase ALAS2 enzymatic activity, leading to an increased pathway flux to such an extend that overwhelms the capacity of the last enzyme in the pathway which is ferrochelatase (FECH). As a result, the penultimate pathway intermediate, protoporphyrin IX (PPIX), cannot be processed and thus accumulates in the body.

"Erythropoietic proporphyria" (EPP) is caused by loss-of-function mutations in FECH. Reduction in FECH activity creates a bottleneck that also results in accumulation of PPIX.

PPIX, uroporphyrin I, and coproporphyrin I can be the molecular culprits of these erythroporphyrias. These molecules are photo-excited when exposed to light in the skin, generating reactive species that cause intense pain and other features characteristics of these diseases. Therefore, reduction of these metabolites may help ameliorate the erythroporphyrias.

Myelodysplastic syndrome associated with isolated del (5q) (Del5q MDS) or Diamond-Blackfan anemia (DBA) are rare disorders caused by defects in ribosomal proteins, which are important in protein translation. Heme production and globin protein synthesis are highly coordinated events during red cell maturation. However, due to the defects in ribosomal protein functions, the translation of globin proteins in Del5q MDS and DBA can be outpaced by the synthesis of heme, resulting in accumulation of toxic level of heme, which in turn inhibits erythropoiesis. Thus, the methods provided herein inhibiting heme production may help treating Del5q MDS or DBA.

"Congenital erythropoietic protoporphyria" (CEP) is caused by loss-of-function mutations in uroporphyrinogen III synthase (UROS). Normally, UROS converts hydroxymethylbilane to uroporphyrinogen III, which is a physiological and direct product that can be further metabolized. Mutations of UROS cause a blockade at this enzymatic step, leading to accumulation of hydroxymethylbilane. Accumulated hydroxymethylbilane can undergo a non-enzymatic reaction to form uroporphyrinogen I and eventually uroporphyrin I or coproporphyrin I, which are both non-physiological and dead-end products that cannot be further metabolized, thereby resulting in their accumulation in the body.

Another class of disorders that can be treated with a compound of Formula (I) or a pharmaceutically acceptable salt thereof is "anemia", which is a disorder associated with a deficiency of red blood cells (RBCs) and/or hemoglobin. In one embodiment, the anemia is further associated with deregulated ALAS2, examples of which include Diamond-Blackfan anemia and X-sideroblastic anemia.

Yet another group of disorders that can be treated with a compound of Formula (I) or a pharmaceutically acceptable salt thereof is are disorders that are caused by defects in ribosomal proteins. Due to defects in ribosomal protein functions, the translation of globin proteins these disorders is outpaced by heme synthesis, thereby resulting in accumulation of a toxic levels of heme, which in erythropoiesis (i.e., production of RBCs). Examples of disorders that are caused by the defects in ribosomal proteins are in myelodysplastic syndrome (MDS) with isolated del(5q) and Diamond-Blackfan anemia.

Combining ALAS2 Inhibitor Treatment with Standard Therapies

In certain embodiments, the subject is concomitantly receiving or has received β-carotene therapy, porphyrin absorbent therapy, afamelanotide treatment, or blood transfusion.

Oral beta-carotene therapy includes Lumitene and Tishcon to improve an affected individual's tolerance of sunlight. Porphyrin absorbent therapy includes cholestyramine and activated charcoal.

The disclosed methods can also be used in combination with Scenesse (afamelanotide), which has been approved for the treatment of erythropoietic protoporphyria in Europe and works by increasing skin pigmentation to provide protection and improves sun tolerance.

To treat iron deficiency, the disclosed methods can be combined with iron supplements. In addition, the disclosed methods can be combined with cholestyramine or activated charcoal to interrupt the circulation of protoporphyrin through the liver and intestines in patients with liver disease.

Individuals with high levels of protoporphyrin in the plasma and red blood cells are at risk of liver malfunction that could eventually lead to liver failure. Liver transplantation has been performed as a life-saving measure in patients with EPP and XLP related liver failure. Bone marrow transplant can also be performed after liver transplant to prevent further damage to the liver. The disclosed methods can be used with subjects who have undergone liver and/or bone marrow transplants.

Animal (Mouse) Model of XLP

X-linked protoporphyria (XLP) (see NCBI MIM 300752, incorporated herein by reference) is an erythropoietic porphyria due to gain-of-function mutations in the erythroid-specific aminolevulinate synthase gene (ALAS2). Two previously identified exon 11 small deletions, namely c. 1699_1670ΔAT (ΔAT) and c.1706_1709ΔAGTG (ΔAGTG), have been identified to prematurely truncate or elongate the wild-type ALAS2 polypeptide, leading to increased ALAS2 enzymatic activity of about 20- to 40-fold, thus causing the erythroid accumulation of protoporphyrins, cutaneous photosensitivity, and liver disease. Three additional mutations, a frameshift mutation cause by 26 bp deletion (c. 1651-1677del26bp), c. 1734ΔG (ΔG), and c. 1642C>T (p.Q548X, a nonsense mutation), as well as an engineered deletion mutation, c. 1670-1671TC>GA p.F557X, were also expressed and characterized (Ducamp et al., *Human Molecular Genetics* 22(7): 1280-1288, 2013; Bishop et al., *Mol. Med.* 19(1): 18-25, 2013). According to Bishop, compared to the purified wild-type enzyme, ΔAT, ΔAGTG and Q548X enzymes had increased specific activities that were 1.8-, 3.1- and 1.6-fold, respectively. Meanwhile, the elongated ΔG enzyme had wild-type specific activity, kinetics and thermostability; but twice the wild-type purification yield (56 versus 25%); suggesting greater stability in vivo. On the basis of studies of mutant enzymes, the maximal gain-of function region spanned 57 amino acids between 533 and 580. Overall, these ALAS2 gain-of-function mutations increased the specific activity (ΔAT, ΔAGTG and p.Q548X) or stability (ΔG) of the enzyme, thereby leading to the increased erythroid protoporphyrin accumulation causing XLP.

Thus, another aspect of the invention provides a mouse (*Mus musculus*) as an animal model for X-linked protoporphyria (XLP), wherein the mouse comprises a genomic ALAS2 (5-AminoLevulinic Acid Synthase 2)-gain-of-function (gof) mutation at the mouse ALAS2 locus, wherein the genomic ALAS2-gof mutation encodes a mutant ALAS2 protein with increased activity and/or stability over a wild-type ALAS2 protein, and corresponds to or recapitulates a human ALAS2-gof mutation in an XLP human patient.

In certain embodiments, the genomic ALAS2-gof mutation corresponds to or recapitulates a human ALAS2-gof mutation selected from the group consisting of: c. 1651-1677del26bp, c. 1699_1670ΔAT (ΔAT); c.1706_1709ΔAGTG (ΔAGTG); c. 1734AG (AG); c. 1642C>T (p.Q548X); and c. 1670-1671TC>GA p.F557X.

In certain embodiments, the genomic ALAS2-gof mutation corresponds to or recapitulates a human ALAS2-gof nonsense mutation selected from the group consisting of: p.G544X and p.G576X.

According to this aspect of the invention, the endogenous mouse ALAS2 gene is modified to mimic the genetic gof mutation found in a human XLP patient, such as the human ALAS2-delAT (c.1699_1670ΔAT) mutation in an XLP human patient, in which the dinucleotides AT at nt. 1699 and 1670 are deleted. The mutation can be introduced into a mouse zygote using any art-recognized means, such as CRISPR/Cas-mediated gene editing, or introduced into a mouse ES (embryonic stem) cell via traditional homologous recombination.

Specifically, in one embodiment, the mouse (*Mus musculus*) is an animal model for X-linked protoporphyria (XLP), wherein the mouse comprises a genomic ALAS2 (5-AminoLevulinic Acid Synthase 2)-delAT mutation at the mouse ALAS2 locus, wherein the genomic ALAS2-delAT mutation encodes a mutant ALAS2 protein with a C-terminal deletion, and corresponds to or recapitulates the human ALAS2-delAT (c.1699_1670ΔAT) mutation in an XLP human patient (e.g., the mouse has the identical C-terminal protein deletion seen in human XLP patients with the delAT mutation).

In certain embodiments, the mouse has elevated level of blood protoporphyrin IX (PPIX) and Zn-PPIX compared to a syngeneic wild-type mouse.

In certain embodiments, the mouse is an inbred strain of mouse, such as C57BL/6 mouse.

In certain embodiments, the mouse is a male, which is hemizygous for the mutation on the X chromosome ($ALAS2^{delAT/Y}$).

In certain embodiments, the mouse is a female, which can be heterozygous or homozygous for the mutation. In particular, in certain embodiments, the mouse is homozygous for the genomic ALAS2-delAT mutation ($ALAS2^{delAT/delAT}$). In certain other embodiments, the mouse is heterozygous for the genomic ALAS2-delAT mutation (i.e., the female mouse comprises one wild-type allele of ALAS2) ($ALAS2^{delAT/WT}$).

In certain embodiments, the mouse comprises the genomic DNA sequence of SEQ ID NO: 5, which comprises silent point mutations in addition to the mutations responsible for the gof mutant phenotype.

In certain embodiments, the mouse is generated by CRISPR/Cas9-mediated homology-directed repair (HDR) that deletes the AT dinucleotide in the genomic ALAS2-delAT mutation.

In certain embodiments, the CRISPR/Cas9-mediated HDR is carried out by microinjecting into the pronucleus of a mouse zygote an mRNA encoding Cas9, an sgRNA, and a single-stranded DNA (ssDNA) (e.g., all 10 ng/μL).

In particular, a CRISPR/Cas9 coding sequence (e.g., Cas9 mRNA), its single guide RNA (sgRNA) targeting an ALAS2 sequence for generating a double-stranded break (DSB) to facilitate homology-directed repair (HDR) using a donor DNA (e.g., a single-stranded donor DNA) harboring the desired sequence change to introduce the mutation (e.g., the AT dinucleotide deletion), and the donor DNA, can be introduced together into the nucleus of a mouse zygote by, for example, microinjection or eletroporation. Upon synthesis of the Cas9 enzyme in the zygote, the sgRNA is loaded onto the Cas9 effector enzyme to generate a DSB, which can be repaired by HDR using the sequence in the donor DNA.

The zygote (e.g., a zygote for a male mouse) having such mutation on the X chromosome is then allowed to develop to term in a surrogate female to generate the founder male mouse and the female mouse (which can be homozygous or heterozygous for the mutation). Subsequent crossing of the male and/or female founders to the background strain produces female progenies that are homozygous or heterozygous and male progenies that are hemizygous for the mutation. The presence of mutations can be verified through genotyping using standard technology, such as PCR using genomic DNA isolated from tails and toes.

In certain embodiments, the single guide RNA (sgRNA) for CRISPR/Cas9 comprises the nucleotide sequence of SEQ ID NO: 4.

In certain embodiments, the CRISPR/Cas9-mediated HDR utilizes a donor DNA having the polynucleotide sequence of SEQ ID NO: 5.

In certain embodiments, the CRISPR/Cas9-mediated HDR utilizes a donor DNA from an XLP patient (e.g., a mouse or a human patient).

Other Definitions

The terms "effective amount" and "therapeutically effective amount" are used interchangeably throughout the present disclosure, when referring to a compound of Formula (I) or a pharmaceutically acceptable salt thereof.

An "effective amount" of a compound of Formula (I) or a pharmaceutically acceptable salt thereof is an amount sufficient to provide a therapeutic benefit in the treatment of a disorder, such a disorder associated with deregulated ALAS2. Additionally or alternatively, an "effective amount" of a compound of Formula (I) or a pharmaceutically acceptable salt thereof is an amount sufficient to delay or reduce one or more effects or symptoms associated with these disorders. In one aspect, an "effective amount" of a compound of Formula (I) or a pharmaceutically acceptable salt thereof, alone or in combination with other therapies, which provides a therapeutic benefit in the treatment of the disorder. The term "effective amount" can encompass an amount that improves overall therapy, reduces or avoids effects, symptoms, signs, or causes of the condition, and/or enhances the therapeutic efficacy of another therapeutic agent. In certain embodiments, an "effective amount" of a compound of Formula (I) or a pharmaceutically acceptable salt thereof is an amount sufficient for eliciting measurable inhibition of ALAS2. In certain embodiments, an "effective amount" of a compound of Formula (I) or a pharmaceutically acceptable salt thereof is an amount sufficient for degrading or inhibiting ALAS2 in a subject in need thereof. In certain embodiments, an "effective amount" of a compound of Formula (I) or a pharmaceutically acceptable salt thereof is an amount sufficient for reducing the amount of at least one metabolite selected from the group consisting of 5-aminolevulinic acid, 8-aminolevulinic acid (8ALA), porphobilinogen (BPG), hydroxymethylbilane (HMB), uroporphyrinogen I, uroporphyrinogen III (UROgen III), coproporphyrinogen I, coproporphyrinogen III (CPgenIII), protoporphyrinogen IX, uroporphyrin I, coproporphyrin I, heme, and protoporphyrin IX (PPIX). In one aspect, the effective amount of a compound of Formula (I) or a pharmaceutically acceptable salt thereof is between about 0.01-100 mg/kg body weight/day of the compound.

The terms "treatment," "treat," and "treating" refer to reversing, alleviating, reducing the likelihood of developing, or inhibiting the progress of a disease or disorder, or one or more effects or symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to reduce the likelihood of or delay their recurrence.

As used herein the terms "subject" and "patient" may be used interchangeably, and means a mammal or a human in need of treatment with a compound of Formula (I) or a pharmaceutically acceptable salt thereof.

The terms "composition" and "formulation" are used interchangeably.

The compositions delineated herein include the compounds delineated herein (e.g., a compound of Formula (I) or a pharmaceutically acceptable salt thereof described herein), as well as additional therapeutic agents if present, in amounts effective for achieving a modulation of disease or disease symptoms, including those described herein.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

EXEMPLIFICATIONS

Abbreviations List

| Abbrv. | Full Name | Abbrv. | Full Name |
|---|---|---|---|
| anhy. | anhydrous | aq. | aqueous |
| min | minute(s) | satd. | saturated |
| mL | milliliter | h or hrs | hours |
| mmol | millimole(s) | mol | mole(s) |
| MS | mass spectrometry | NMR | nuclear magnetic resonance |
| TLC | thin layer chromatography | HPLC | high-performance liquid chromatography |
| LCMS | Liquid chromatography-mass spectrometry | nBuLi | n-butyllithium |
| DCE | 1,2-dichloroethane | $CHCl_3$ | chloroform |
| DCM | dichloromethane | DMF | dimethylformamide |
| Et2O | diethyl ether | EtOH | ethyl alcohol |
| EtOAc | ethyl acetate | MeOH | methyl alcohol |
| MeCN | acetonitrile | PE | petroleum ether |
| THF | tetrahydrofuran | DMSO | dimethyl sulfoxide |
| AcOH | acetic acid | HCl | hydrochloric acid |
| $H_2SO_4$ | sulfuric acid | $NH_4Cl$ | ammonium chloride |
| KOH | potassium hydroxide | NaOH | sodium hydroxide |
| $K_2CO_3$ | potassium carbonate | $Na_2CO_3$ | sodium carbonate |
| TFA | trifluoroacetic acid | $Na_2SO_4$ | sodium sulfate |
| $NaBH_4$ | sodium borohydride | $NaHCO_3$ | sodium bicarbonate |
| LiHMDS | lithium hexamethyldisilylamide | $NaBH_4$ | sodium borohydride |
| $Et_3N$ or TEA | Triethylamine | Py or Pyr | pyridine |
| DMAP | 4-(dimethyl-amino)pyridine | DIPEA | N,N-diisopropylethylamine |
| CDI | 1,1'-Carbonyldiimidazole | $NaNO_2$ | Sodium nitrite |
| $SnCl_2$ | Stannous chloride | | |

General Experimental

In the following examples, the chemical reagents were purchased from commercial sources (such as Alfa, Acros, Sigma Aldrich, TCI and Shanghai Chemical Reagent Company), and used without further purification. Flash chromatography was performed on an Ez Purifier III via column with silica gel particles of 200-300 esh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland) at around 20-30° C. unless otherwise specified. The following abbreviations are used: s, singlet; d, doublet; t, triplet; q, quartet; m, multiplet; dd, doublet of doublets; ddd, doublet of doublet of doublet; dt, doublet of triplets; bs, broad signal. Chemical shifts were reported in parts per million (ppm, δ) downfield from tetramethylsilane. Mass spectra were run with electrospray ionization (ESI) from a Waters LCT TOF Mass Spectrometer (Waters, USA). Compound purification was carried out as needed using a variety of traditional methods including, but not limited to, preparative chromatography under acidic, neutral, or basic conditions using either normal phase or reverse phase HPLC or flash columns or Prep-TLC plates.

Preparative HPLC (Prep-HPLC): Unless otherwise described, the compounds were purified using a WATERS Fractionlynx system equipped with a YMC Pack Pro $d_8$ Column (5 μm, 120A, 50×20 mm) and the following solvent system: $H_2O$, MeCN, and 2% TFA in $H_2O$. Specific elution gradients were based on the retention times obtained with an analytical LC-MS, however, in general all elution gradients of $H_2O$ and MeCN were run over a 7 minute run time with a flow rate of 35 mL/min. An autoblend method was used to ensure a concentration of 0.1% TFA throughout each run. Specific elution gradients were based on the retention times obtained with an analytical LC-MS, however, in general, all elution gradients of $H_2O$ and MeCN were run over an 8 minute run time with a flow rate of 50 mL/min.

Analytical LC-MS: Analytical LC-MS was performed on a WATERS Acquity UPLC-MS instrument equipped with a ACQUITY UPLC BEH $Ci_8$ Column (2.1×50 mm, 1.7 μm), a column temperature of 45° C. and using the following solvent system: Solvent A: 0.1% HCOOH in $H_2O$; and Solvent B: 0.1% HCOOH in AcCN. All compounds were run using the same elution gradient, i.e., 5% to 95% Solvent B over a 1.5 min run time with a flow rate of 0.6 mL/min.

Examples 1-35 show the exemplified synthesis of the compounds as described herein.

Example 1

Synthesis of 5-hydrazinyl-3-(2-(pyridin-4-yl)propan-2-yl)-1,2,4-oxadiazole

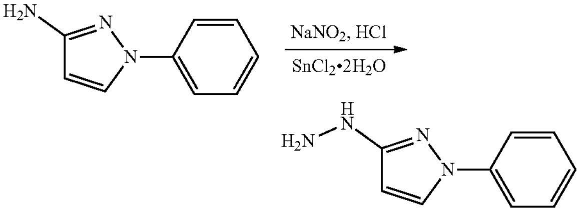

To a solution of 1-phenyl-1H-pyrazol-3-amine (200 mg, 1.26 mmol) in HCl (2 M, 3 mL) was added $NaNO_2$ (174 mg, 2.52 mmol) dropwise over 5 min at 0° C. The mixture was stirred at 0° C. for 40 min and $SnCl_2 \cdot 2H_2O$ (853 mg, 3.78 mmol) was added dropwise. The reaction was stirred at 0° C. for 3 h. The mixture was concentrated under reduced pressure and the residue was purified by Pre-HPLC to afford 3-hydrazinyl-1-phenyl-1H-pyrazole (22 mg, 10% yield) as a white solid. $^1H$ NMR (400 MHZ, Methanol-d4) δ 8.03 (d, J=2.8 Hz, 1H), 7.67 (d, J=8.0 Hz, 2H), 7.44-7.40 (m, 2H), 7.23-7.19 (m, 1H), 6.01 (s, 1H); LCMS $(M+H)^+$: 175.

Example 2

Synthesis of 3-hydrazinyl-5-(o-tolyl)-4H-1,2,4-triazole

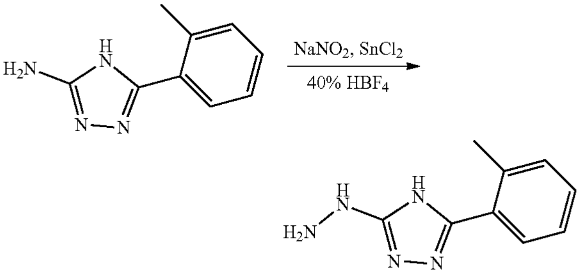

To a stirred solution of 5-(o-tolyl)-4H-1,2,4-triazol-3-amine (348 mg, 2.0 mmol) in $HBF_4$ (5 ml, wt: 30% in water) was added a solution of $NaNO_2$ (276 mg, 4.0 mmol) in water (0.5 mL) dropwise at 0° C. The resulting mixture was stirred for 30 min before dropwise added a solution of $SnCl_2·2H_2O$ (1.8 g, 8.0 mmol) in water (0.5 mL). The reaction mixture was allowed to warm up to at room temperature and stirred for 3 h. The mixture was concentrated under reduced pressure. The residue was purified by Prep-HPLC to give 3-hydrazinyl-5-(o-tolyl)-4H-1,2,4-triazole (30 mg, 4.0% yield). $^1H$ NMR (400 MHZ, CD3OD) δ: 7.55-7.52 (m, 1H), 7.34-7.21 (m, 3H), 2.45 (s, 3H); LCMS $(M+1)^+$: 190.

Example 3

Synthesis of 3-cyclobutyl-5-hydrazinyl-4H-1,2,4-triazole

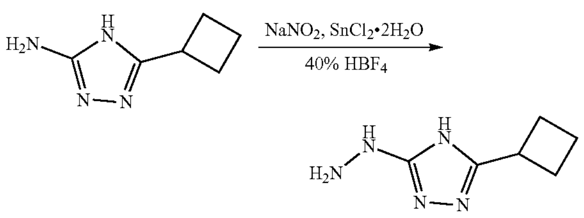

To a solution of 5-cyclobutyl-4H-1,2,4-triazol-3-amine (200 mg, 1.45 mmol) in 40% $HBF_4$ (3 ml) was added $NaNO_2$ (188 mg, 2.72 mmol) dropwise over 5 min. at 0° C. The mixture was stirred at 0° C. for 40 min and $SnCl_2·2H_2O$ (922 mg, 4.08 mmol) was added dropwise. The reaction was stirred at 0° C. for 3 h. The mixture was concentrated under reduced pressure and the residue was purified by Prep-HPLC to afford 3-cyclobutyl-5-hydrazinyl-4H-1,2,4-triazole (4.2 mg, 2% yield) as white solid. $^1H$ NMR (400 MHZ, $CD_3OD$) δ 8.10 (s, 1H), 3.55-3.48 (m, 1H), 2.36-2.30 (m, 4H), 2.11-2.04 (m, 1H), 1.97-1.93 (m, 1H); LCMS $(M+1)^+$: 154

Example 4

Synthesis of 3-hydrazinyl-5-propyl-4H-1,2,4-triazole

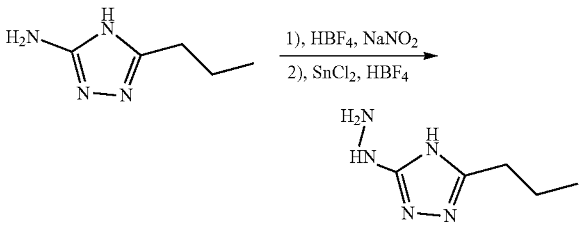

To a solution of 5-propyl-4H-1,2,4-triazol-3-amine (100 mg, 0.79 mmol) in $HBF_4$ (1 mL) at −10° C. was added $NaNO_2$ (55 mg, 0.79 mmol, in water (0.5 mL)) dropwise. Then the reaction mixture was added to a solution of $SnCl_2$ (451 mg, 2.38 mmol) in $HBF_4$ (2 mL) at −10° C. slowly and the reaction mixture was stirred and allowed to warm to room temperature over 60 minutes. The reaction mixture was concentrated and the residue was purified by Prep-HPLC to give 3-hydrazinyl-5-propyl-4H-1,2,4-triazole (12.1 mg, 10.8% yield) as a pale oil. $^1H$ NMR (400 MHZ, $CD_3OD$) δ 2.73 (t, J=7.6 Hz, 1H), 2.68 (t, J=7.6 Hz, 1H), 1.80-1.722 (m, 2H), 1.02-0.96 (m, 3H); LC-MS $(M+1)^+$: 142.

Example 5

Synthesis of 4-(5-hydrazinyl-1H-1,2,4-triazol-3-yl)morpholine

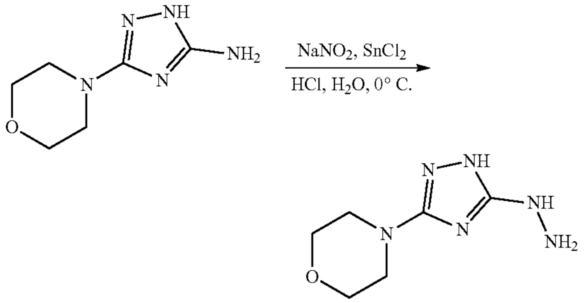

To a solution of 3-morpholino-1H-1,2,4-triazol-5-amine (200 mg, 1.18 mmol) in HCl (2 M, 3 mL) was added $NaNO_2$ (163 mg, 2.36 mmol) dropwise over 5 min at 0° C. The mixture was stirred at 0° C. for 40 min and $SnCl_2·2H_2O$ (673 mg, 3.54 mmol) was added dropwise. The reaction was stirred at 0° C. for 3 h. The mixture was concentrated under reduced pressure and the residue was purified by Pre-HPLC to afford 4-(5-hydrazinyl-1H-1,2,4-triazol-3-yl)morpholine (18 mg, 8% yield) as a white solid. $^1H$ NMR (400 MHZ, $CD_3OD$) δ 3.70 (t, J=4.8 Hz, 4H), 3.39-3.33 (t, J=4.8 Hz, 4H); LC-MS $(M+1)^+$: 185.

Example 6

Synthesis of 3-hydrazinyl-1-(2,2,2-trifluoroethyl)-1H-pyrazole

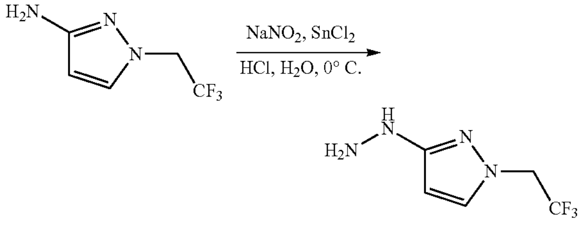

To a solution of 1-(2,2,2-trifluoroethyl)-1H-pyrazol-3-amine (100 mg, 0.61 mmol) in HCl (2 M, 3 mL) was added $NaNO_2$ (84.2 mg, 1.22 mmol) dropwise over 5 min at 0° C. The mixture was stirred at 0° C. for 40 min and $SnCl_2·2H_2O$ (346 mg, 1.83 mmol) was added dropwise. The reaction was stirred at 0° C. for 3 h. The mixture was concentrated under reduced pressure and the residue was purified by Pre-HPLC to afford 3-hydrazinyl-1-(2,2,2-trifluoroethyl)-1H-pyrazole (20 mg, 18% yield) as a white solid. $^1H$ NMR (400 MHZ, $CD_3OD$) δ 8.21 (s, 1H), 7.57 (d, J=2.8 Hz, 1H), 5.89 (d, J=2.4 Hz, 1H), 4.76 (q, J=8.8 Hz, 2H); LC-MS $(M+1)^+$: 181.

Example 7

Synthesis of 3-hydrazinyl-1-isopropyl-1H-pyrazole

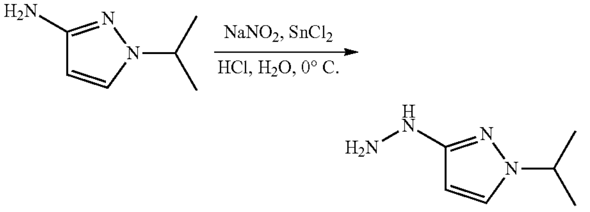

To a solution of 1-isopropyl-1H-pyrazol-3-amine (100 mg, 0.80 mmol) in HCl (2 M, 3 mL) was added $NaNO_2$ (110.4 mg, 1.60 mmol) dropwise over 5 min at 0° C. The mixture was stirred at 0° C. for 40 min and $SnCl_2 \cdot 2H_2O$ (456 mg, 2.40 mmol) was added dropwise. The reaction was stirred at 0° C. for 3 h. The mixture was concentrated under reduced pressure and the residue was purified by Pre-HPLC to afford 3-hydrazinyl-1-isopropyl-1H-pyrazole (33 mg, 28% yield) as a white solid. $^1H$ NMR (400 MHZ, $CD_3OD$) δ 7.50 (d, J=1.6 Hz, 1H), 5.80 (d, J=2.0 Hz, 1H), 4.42-4.33 (m, 1H), 1.44 (d, J=6.8 Hz, 6H); LC-MS $(M+1)^+$: 141.

Example 8

Synthesis of 1-(2,2-difluoroethyl)-3-hydrazinyl-1H-pyrazole

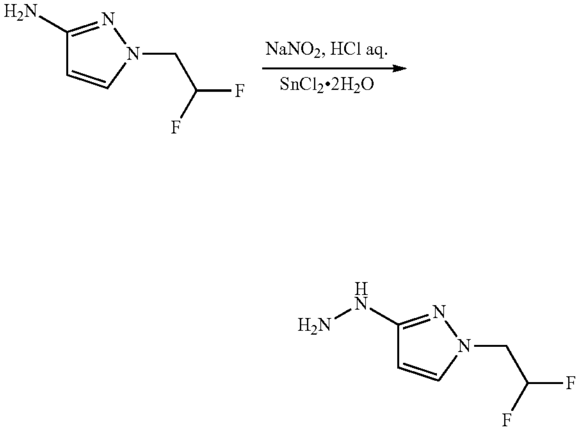

To a solution of 1-(2,2-difluoroethyl)-1H-pyrazol-3-amine (200 mg, 1.36 mmol) in HCl (2 M, 3 mL) was added $NaNO_2$ (187.7 mg, 2.72 mmol) dropwise over 5 min at 0° C. The mixture was stirred at 0° C. for 40 min and $SnCl_2 \cdot 2H_2O$ (775 mg, 4.08 mmol) was added dropwise. The reaction was stirred at 0° C. for 3 h. The mixture was concentrated under reduced pressure and the residue was purified by Pre-HPLC to afford 1-(2,2-difluoroethyl)-3-hydrazinyl-1H-pyrazole (35 mg, 16% yield) as a white solid. $^1H$ NMR (400 MHZ, $D_2O$) δ 7.56 (d, J=2.8 Hz, 1H), 6.31-5.93 (m, 2H), 4.42 (td, J=15.2, 3.6 Hz, 2H); LC-MS $(M+1)^+$: 163.

Example 9

Synthesis of 3-hydrazinyl-5-phenyl-4H-1,2,4-triazole

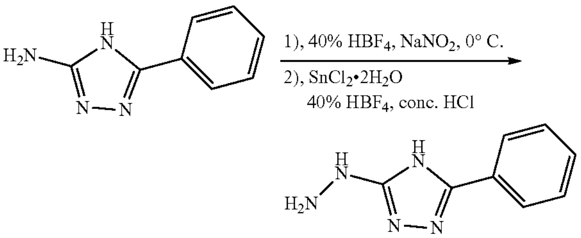

To a stirred suspension of 5-phenyl-4H-1,2,4-triazol-3-amine (160 mg, 1 mmol) and water (0.3 mL) was added aq. tetrafluoroboric acid (3 mL, 48%) in small portions. After the final suspension had been cooled to 0° C., a concentrated aqueous sodium nitrite (69 mg, 1 mmol) was added dropwise, and the mixture was stirred for 10 min at 0° C. The white solid was collected by filtration which was used immediately in the next step. The solid was added in small portions to a stirred solution of stannous chloride (563 mg, 2.5 mmol) in concentrated hydrochloric acid (2 mL) and 48% tetrafluoroboric acid (2 mL) at 0° C. After the mixture had been stirred for 5 min, the solid was collected by filtration and further purified by prep-HPLC to give pure 3-hydrazinyl-5-phenyl-4H-1,2,4-triazole (50 mg, 28.6%) as a white solid. $^1H$ NMR (400 MHZ, $CD_3OD$) δ 8.03-7.81 (m, 2H), 7.57-7.51 (m, 3H); LC-MS $(M+1)^+$: 176.1.

Example 10

Synthesis of 2-(3-hydrazinyl-1H-pyrazol-1-yl)acetic Acid

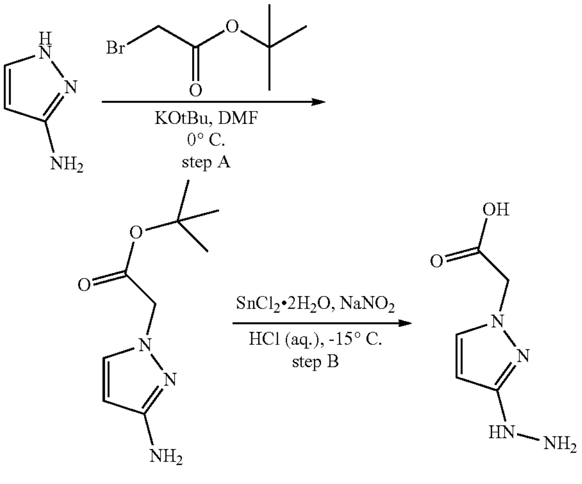

Step A. Synthesis of tert-butyl 2-(3-amino-1H-pyrazol-1-yl) acetate

At 0° C., tBuOK (1.9 g, 16.6 mmol) was added to a solution of 1H-pyrazol-3-amine (1.2 g, 14.5 mmol) in DMF (15 mL). The mixture was stirred for 40 min before tert-butyl 2-bromoacetate (3.2 g, 16.6 mmol) in DMF (2 mL)

was added. The reaction was stirred at 0° C. for 10 min and then warmed up to RT and stirred for 1 h. $H_2O$ (50 mL) was added and extracted with EtOAc (50 mL×3). The organic phase was concentrated, the residue was puried by FC to give tert-butyl 2-(3-amino-1H-pyrazol-1-yl) acetate (1.1 g, 38.6% yield) as a white solid. LC-MS $(M+1)^+$: 198.1.

Step B. Synthesis of 2-(3-hydrazinyl-1H-pyrazol-1-yl)acetic acid

To a solution of tert-butyl 2-(3-amino-1H-pyrazol-1-yl) acetate (1.1 g, 5.6 mmol) in conc·HCl (10 mL) and MeOH (10 mL) was added $NaNO_2$ (390 mg, 5.6 mmol) in $H_2O$ (1 mL) at −5° C. The mixture was stirred at −5° C. for 1 h before $SnCl·2H_2O$ (3.8 g, 16.8 mmol) in conc·HCl (20 mL) was dropwise added. The reaction was stirred for another 1 h at −5° C. The solvent was removed under reduced pressure. The residue was puried by Prep-HPLC to give 2-(3-hydrazinyl-1H-pyrazol-1-yl)acetic acid as a white solid (380 mg, 43.5% yield). $^1H$ NMR (400 MHZ, $D_2O$) δ 7.52 (d, J=2.5 Hz, 1H), 5.97 (d, J=2.5 Hz, 1H), 4.88 (s, 2H); LCMS $(M+1)^+$: 157.

Example 1

Synthesis of 3-(1-methylhydrazinyl)-5-(trifluoromethyl)-4H-1,2,4-triazole

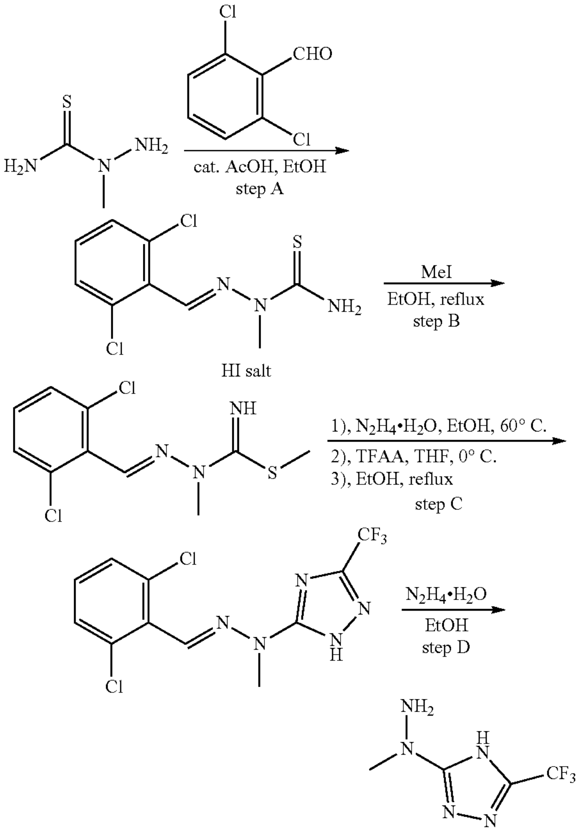

Step A. Synthesis of (E)-2-(2,6-dichlorobenzylidene)-1-methylhydrazine-1-carbothioamide To a stirred solution of 2,6-dichlorobenzaldehyde (1.74 g, 9.98 mmol) in EtOH (20 mL) was added 1-methylhydrazine-1-carbothioamide (1.0 g, 9.51 mmol) and a drop of AcOH. The resulting mixture was heated to reflux and stirred for 6 hrs. After cooling to 0° C., the resulting precipitates were collected by filtration, washed with PE and dried in vacuo to give (E)-2-(2,6-dichlorobenzylidene)-1-methylhydrazine-1-carbothioamide (2.3 g, 93% yield) as a white solid. LCMS $(M+1)^+$: 262.

Step B. Synthesis of methyl (E)-2-(2,6-dichlorobenzylidene)-1-methylhydrazine-1-carbimidothioate HI salt To a mixture of (E)-2-(2,6-dichlorobenzylidene)-1-methylhydrazine-1-carbothioamide (1.2 g, 4.57 mmol) in EtOH (30 mL) was added MeI (714 mg, 5.03 mmol). The resulting mixture was stirred at 65° C. under $N_2$ for 3 hr. After cooling to r.t, the reaction solution was concentrated in vacuo to dryness to give the desired product methyl (E)-2-(2,6-dichlorobenzylidene)-1-methylhydrazine-1-carbimidothioate HI salt as a white solid (1.8 g, 100% yield). LC-MS $(M+1)^+$: 276.0.

Step C. Synthesis of (E)-5-(2-(2,6-dichlorobenzylidene)-1-methylhydrazinyl)-3-(trifluoromethyl)-1H-1,2,4-triazole To a mixture of methyl (E)-2-(2,6-dichlorobenzylidene)-1-methylhydrazine-1-carbimidothioate HI salt (900 mg, 2.22 mmol) in EtOH (50 mL) was added $N_2H_4·H_2O$ (334 mg, 6.68 mmol). The resulting mixture was stirred at 60° C. under $N_2$ for 3 hr till LCMS showed most of starting material was converted into hydrazine substituted intermediate. After cooling to r.t, the reaction solution was concentrated in vacuo to dryness and then dissolved in THF (50 mL). TFAA (1.2 g, 5.77 mmol) was added dropwise at 0° C. After the addition, the resulting mixture was stirred at r.t for 0.5 hr till LCMS showed the acylation was almost complete. Then, the mixture was concentrated in vacuo and the residue was diluted with EtOH (50 mL), followed by the addition of conc. $H_2SO_4$ (4 drops). The resulting solution was heated to reflux and stirred for 24 hr. After cooling to 0° C., the mixture was poured into ice water and extracted with EtOAc twice, the combined extracts were washed with brine, concentrated in vacuo and the residue was purified by column chromatography (Silica gel 60-120, 1:5, ethyl acetate/hexane) to give (E)-5-(2-(2,6-dichlorobenzylidene)-1-methylhydrazinyl)-3-(trifluoromethyl)-1H-1,2,4-triazole as a white solid (200 mg, 18.1% yield). LC-MS $(M+1)^+$: 338.0.

Step D. Synthesis of 3-(1-methylhydrazinyl)-5-(trifluoromethyl)-4H-1,2,4-triazole To a mixture of (E)-5-(2-(2,6-dichlorobenzylidene)-1-methylhydrazinyl)-3-(trifluoromethyl)-1H-1,2,4-triazole (100 mg, 0.295 mmol) in EtOH (3 mL) was added $N_2H_4·H_2O$ (0.1 mL). The resulting mixture was stirred at 100° C. in a sealed tube for 14 hr till LCMS showed the completion of the reaction. After concentration in vacuo, the residue was purified by prep-HPLC to give 3-(1-methylhydrazinyl)-5-(trifluoromethyl)-4H-1,2,4-triazole as a white solid (12 mg, 27% yield). $^1H$ NMR (400 MHZ, DMSO-$d_6$) δ 13.04 (s, 1H), 4.84 (s, 2H), 3.11 (s, 3H); LCMS $(M+1)^+$: 182.1

Example 12

Synthesis of 4-(1-methylhydrazinyl)-5-(trifluoromethyl)-2H-1,2,3-triazole

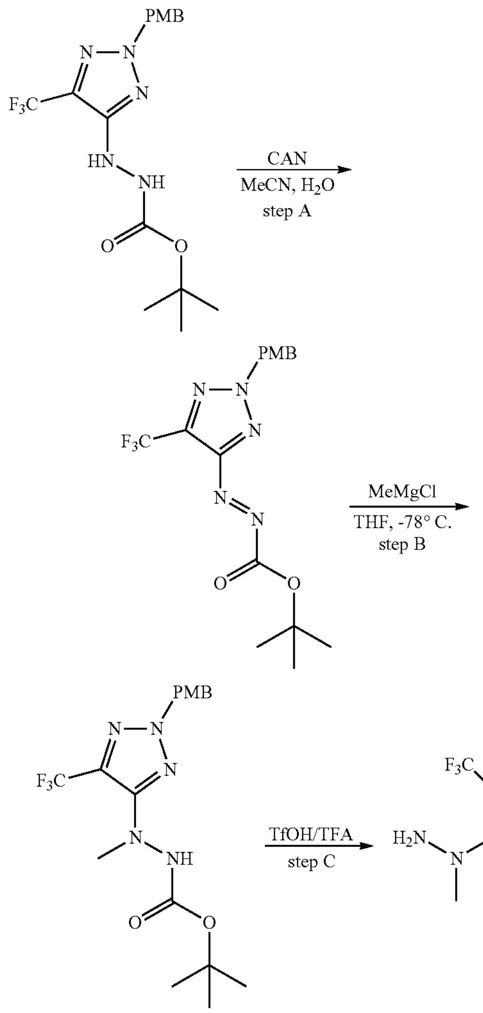

Step A. Synthesis of (E)-tert-butyl 2-(2-(4-methoxybenzyl)-5-(trifluoromethyl)-2H-1,2,3-triazol-4-yl)diazenecarboxylate To a solution of tert-butyl 2-(2-(4-methoxybenzyl)-5-(trifluoromethyl)-2H-1,2,3-triazol-4-yl)hydrazinecarboxylate (116 mg, 0.3 mmol) in MeCN (9 mL) was added dropwise a solution of CAN (550 mg, 1 mmol) at 0° C. After the addition, the solution was stirred at 0° C. for 0.5 h till TLC indicated the completion of the reaction. Then, the reaction solution was diluted with water and extracted with EtOAc twice. The combined extracts were washed with brine, dried over $Na_2SO_4$, concentrated in vacuo and purified by prep-TLC to give (E)-tert-butyl 2-(2-(4-methoxybenzyl)-5-(trifluoromethyl)-2H-1,2,3-triazol-4-yl)diazenecarboxylate (80 mg, 69.3%) as a yellow oil. LCMS $(M+1)^+$: 386.1.

Step B. Synthesis of tert-butyl 2-(2-(4-methoxybenzyl)-5-(trifluoromethyl)-2H-1,2,3-triazol-4-yl)-2-methylhydrazinecarboxylate To a solution of (E)-tert-butyl 2-(2-(4-methoxybenzyl)-5-(trifluoromethyl)-2H-1,2,3-triazol-4-yl)diazenecarboxylate (77 mg, 0.2 mmol) in dry THF (10 mL) was added dropwise MeMgCl (1.0 mL, 1 mmol, 1.0 N in THF) at −78° C. over 3 minutes. After the addition, the mixture was stirred at −78° C. for 10 minutes before it was quenched by the addition of sat. $NH_4Cl$. The final mixture was partitioned between water and EtOAc. The organic layer was separated, washed with brine, concentrated in vacuo and purified by prep-TLC to give tert-butyl 2-(2-(4-methoxybenzyl)-5-(trifluoromethyl)-2H-1,2,3-triazol-4-yl)-2-methylhydrazinecarboxylate (50 mg, 62.5%) as a white solid. $^1$H NMR (400 MHZ, DMSO-$d_6$) δ 9.38 (s, 1H), 7.34 (d, J=8.4 Hz, 2H), 6.99 (d, J=8.4 Hz, 2H), 5.50 (s, 2H), 3.79 (d, J=4.3 Hz, 3H), 3.08 (s, 3H), 1.43 (s, 9H); LCMS $(M+1)^+$:402.2.

Step C. Synthesis of 4-(1-methylhydrazinyl)-5-(trifluoromethyl)-2H-1,2,3-triazole To a solution of tert-butyl 2-(2-(4-methoxybenzyl)-5-(trifluoromethyl)-2H-1,2,3-triazol-4-yl)-2-methylhydrazinecarboxylate (40 mg, 0.1 mmol) in TFA (0.8 mL) was added TfOH (0.2 mL), The resulting solution was stirred at 25° C. overnight. LCMS showed the reaction was complete. The solvents were removed by evaporation and the residue was directly purified by prep-HPLC to give 4-(1-methylhydrazinyl)-5-(trifluoromethyl)-2H-1,2,3-triazole (7 mg, 41.9%) as a white solid. $^1$H NMR (600 MHZ, DMSO-$d_6$) δ 14.68 (s, 1H), 4.65 (s, 2H), 3.02 (s, 3H); LC-MS $(M+1)^+$: 182.1.

Example 13

Synthesis of 4-hydrazinyl-5-(trifluoromethyl)-2H-1.2.3-triazole

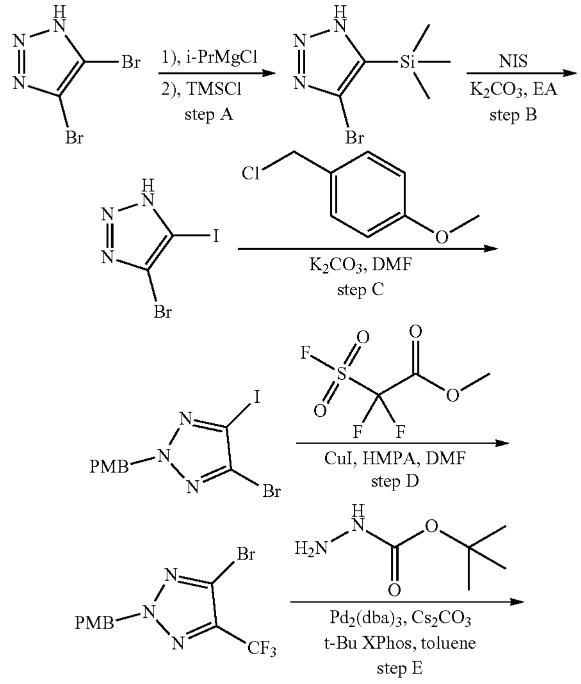

-continued

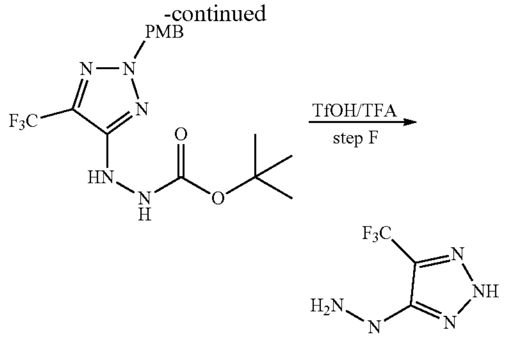

Step A. Synthesis of 4-bromo-5-(trimethylsilyl)-1H-1,2,3-triazole

To a mixture of 4,5-dibromo-1H-1,2,3-triazole (2.27 g, 10 mmol) in dry THF (50 mL) was added i-PrMgCl (11 mL, 22 mmol, 2.0 N in THF) dropwise at −10° C. After the addition, the mixture was stirred at −5° C. for 1 h before TMSCl (2.16 g, 20 mmol) was added dropwise at −10° C. over 5 minutes. Then the reaction mixture was warmed to r.t. and stirred for 2 hours. After the reaction completed, the mixture was treated with sat. $NH_4Cl$, extracted with EA, dried over $Na_2SO_4$ and concentrated in vacuo. The residue was purified by flash chromatography (silica gel, 2%-10% EtOAc in PE) to give 4-bromo-5-(trimethylsilyl)-1H-1,2,3-triazole (1.3 g, 59.4%) as a yellow oil. LCMS $(M+1)^+$: 220.

StepB. Synthesis of 4-bromo-5-iodo-1H-1,2,3-triazole

To a slurry of 4-bromo-5-trimethylsilyl-1,2,3-triazole 2 (1.3 g, 5.9 mmol) and $K_2CO_3$ (138 mg, 1 mmol) in EtOAc (20 mL) was added NIS (1.46 g, 6.5 mmol) at r.t. The mixture was allowed to react for 2 h at r.t. and quenched with 1% $Na_2SO_3$ (20 mL) and EtOAc (30 mL). The organic layer was washed with $H_2O$ (30 mL) and dried over $MgSO_4$. The solvent in organic layer was evaporated under vacuum. The crude product was purified by flash chromatography (silica gel, 5%-20% EtOAc in PE) to give 4-bromo-5-iodo-1H-1,2,3-triazole (0.7 g, 43.7%) as a pale yellow solid. LCMS $(M+1)^+$: 274.

Step C. Synthesis of 4-bromo-5-iodo-2-(4-methoxybenzyl)-2H-1,2,3-triazole

To a solution of 4-bromo-5-iodo-1H-1,2,3-triazole (0.7 g, 2.55 mmol) in dry DMF (15 mL) was added $K_2CO_3$ (1.06 g, 7.66 mmol), follow by the addition of PMBCl (0.48 g, 3.06 mmol) at 0° C. After the addition, the mixture was stirred at 25° C. for 12 h until LCMS showed the reaction was complete. Then the reaction mixture was treated with ice-water and extracted with EA twice. The combined extracts were washed with brine, dried over $Na_2SO_4$ and concentrated in vacuo. The residue was purified by flash chromatography (silica gel, 5%-10% EtOAc in PE) to give 4-bromo-5-iodo-2-(4-methoxybenzyl)-2H-1,2,3-triazole (650 mg, 65%) as a pale yellow solid. $^1H$ NMR (400 MHZ, $CDCl_3$) δ 7.24 (d, J=8.7 Hz, 2H), 6.81 (d, J=8.7 Hz, 2H), 5.40 (s, 2H), 3.73 (s, 3H); LCMS $(M+1)^+$: 394.

Step D. Synthesis of 4-bromo-2-(4-methoxybenzyl)-5-(trifluoromethyl)-2H-1,2,3-triazole A mixture consisting of 4-bromo-5-iodo-2-(4-methoxybenzyl)-2H-1,2,3-triazole (197 mg, 0.5 mmol), methyl 2,2-difluoro-2-(fluorosulfonyl)acetate (288 mg, 1.5 mmol), CuI (95 mg, 0.5 mmol), HMPA (270 mg, 1.5 mmol) and DMF (6 mL) was stirred in a sealed tube under $N_2$ at 100° C. for 6 h. TLC showed ~40% of desired product, ~30% of starting material and ~30% of byproduct with much more polarity. After cooling to r.t, the reaction mixture was treated with water and extracted with EA twice. The combined extracts were washed with brine, dried over $Na_2SO_4$ and concentrated in vacuo. The residue was purified by flash chromatography (silica gel, 2%-10% EA in PE) to give 4-bromo-2-(4-methoxybenzyl)-5-(trifluoromethyl)-2H-1,2,3-triazole (50 mg, 30%) as a white solid. $^1H$ NMR (400 MHZ, CDCl3) δ 7.24 (d, J=8.7 Hz, 2H), 6.81 (d, J=8.7 Hz, 2H), 5.41 (s, 2H), 3.73 (s, 3H); LCMS $(M+1)^+$: 336.

Step E. Synthesis of tert-butyl 2-(2-(4-methoxybenzyl)-5-(trifluoromethyl)-2H-1,2,3-triazol-4-yl)hydrazinecarboxylate A mixture consisting of 4-bromo-2-(4-methoxybenzyl)-5-(trifluoromethyl)-2H-1,2,3-triazole (34 mg, 0.1 mmol), tert-butyl hydrazinecarboxylate (16 mg, 0.12 mmol), Pd2 (dba)3 (8 mg, 0.009 mmol), Di-tert-butyl(2',4',6'-triisopropylbiphenyl-2-yl)phosphine (6 mg, 0.014 mmol), Cs2CO3 (65 mg, 0.2 mmol) and dry toluene (3 mL) was stirred in a sealed tube under N2 at 100° C. for 4 h. LCMS showed the reaction was complete. After cooling to r.t, the reaction mixture was diluted with EA and filtered through celite. The filtrate was concentrated in vacuo and the residue was purified by preparative TLC to give tert-butyl 2-(2-(4-methoxybenzyl)-5-(trifluoromethyl)-2H-1,2,3-triazol-4-yl) hydrazinecarboxylate (26 mg, 67%) as a white solid. LCMS $(M+1)^+$: 388.

Step F. Synthesis of 4-hydrazinyl-5-(trifluoromethyl)-2H-1,2,3-triazole

To a solution of tert-butyl 2-(2-(4-methoxybenzyl)-5-(trifluoromethyl)-2H-1,2,3-triazol-4-yl)hydrazinecarboxylate (25 mg, 0.064 mmol) in TFA (1.2 mL) was added TfOH (0.2 mL) at 0° C. After the addition, the mixture was stirred at 25° C. for 16 h and LCMS showed the reaction was complete. Then the reaction mixture was concentrated in vacuo to remove TFA and TfOH, the residue was co-evaporated with EtOH several times to remove residual TfOH as fully as possible. The final residue was purified by preparative HPLC to give 4-hydrazinyl-5-(trifluoromethyl)-2H-1,2,3-triazole (TfOH salt) (4 mg, 37.2%) as colorless oil. $^1H$ NMR (400 MHZ, DMSO-$d_6$) δ 7.20 (s, 1H), 7.07 (s, 1H), 6.95 (s, 1H); LCMS $(M+1)^+$: 168.

Example 14

Synthesis of 2-hydrazinyl-5-methylthiazole

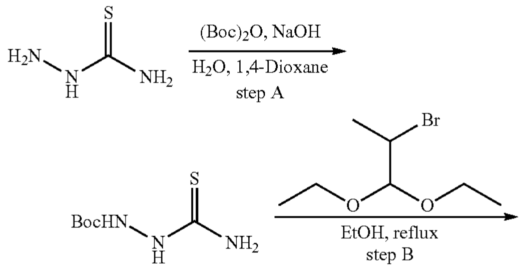

-continued

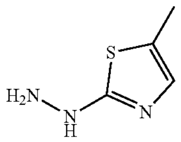

Step A. Synthesis of tert-butyl 2-carbamothioylhydrazine-1-carboxylate

To a solution of hydrazinecarbothioamide (2.0 g, 21.96 mmol) in 1,4-dioxane (20 mL) and $H_2O$ (20 mL) at 0° C. was added NaOH (877 mg, 21.94 mmol) and $(Boc)_2O$ (5.75 g, 26.33 mmol). The reaction mixture was stirred at R.T for 2 hours. The reaction mixture was concentrated under reduced pressure, and purified by column chromatography (Silica gel 10-120, 1:1, ethyl acetate/hexane) to give tert-butyl 2-carbamothioylhydrazine-1-carboxylate as a white solid (1.2 g, 28% yield). LC-MS $(M+1)^+$: 192.1.

Step B. Synthesis of 2-hydrazinyl-5-methylthiazole

To a solution of tert-butyl 2-carbamothioylhydrazine-1-carboxylate (300 mg, 1.56 mmol) in EtOH (10 mL) and $H_2O$ (10 mL), was added 2-bromo-1,1-diethoxypropane (500 mg, 2.34 mmol) and $CH_3COOH$(1drop). The reaction mixture was stirred at 100° C. overnight. The reaction mixture was concentrated under reduced pressure, and purified by column chromatography (dichloromethane/methanol=15:1) followed by Prep-HPLC to give 2-hydrazinyl-5-methylthiazole (4 mg, 2% yield) as a white solid. $^1H$ NMR (400 MHZ, DMSO-$d_6$) δ 6.97 (d, J=1.2 Hz, 1H), 2.25 (d, J=1.2 Hz, 3H); LCMS $(M+1)^+$: 130.0.

Example 15

Synthesis of 2-hydrazinyl-5-(methoxymethyl)thiazole

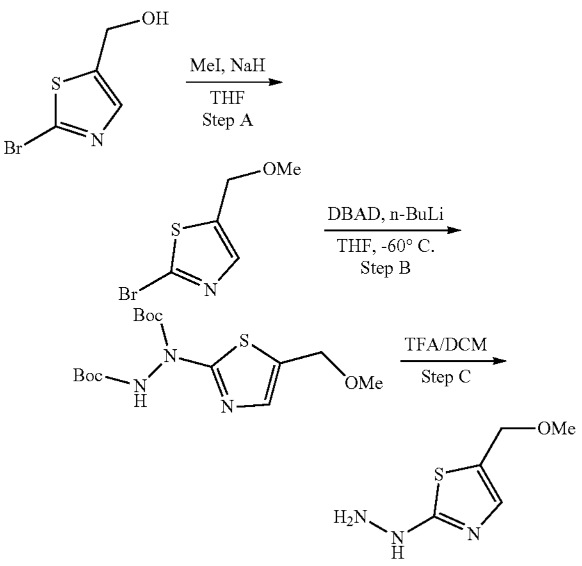

Step A. Synthesis of 2-bromo-5-(methoxymethyl)thiazole

To a suspension of NaH (412 mg, 10.3 mmol, 60% in oil) in anhydrous THF (10 mL) was added a solution of (2-bromothiazol-5-yl)methanol (1.0 g, 5.15 mmol) in THF dropwise at 0° C. and stirred at room temperature for 30 min. Then MeI (1 g, 7.73 mmol) was added to the reaction mixture at 0° C. The resulting mixture was stirred for 30 min at room temperature. After completion of the reaction, the mixture was poured into ice water and extracted with EtOAc (2×50 mL). The combined organic layers were washed with brine (1×50 mL), dried over $Na_2SO_4$, concentrated under reduced pressure and purified by column chromatography (Silica gel 100-200, 1:10, ethyl acetate/hexane) to give 2-bromo-5-(methoxymethyl)thiazole as a colorless oil (500 mg, 50% yield). LC-MS $(M+1)^+$: 208.

Step B. Synthesis of di-tert-butyl 1-(5-(methoxymethyl)thiazol-2-yl)hydrazine-1,2-dicarboxylate To a solution of 2-bromo-5-(methoxymethyl)thiazole (500 mg, 2.4 mmol) in anhydrous THF (20 mL) was added n-BuLi (1.5 mL, 2.5 M in THF) dropwise at −60° C. under $N_2$ and stirred at this temperature for 20 min. Then a solution of DBAD (111 mg, 4.8 mmol) in THF was added dropwise at −60° C. The resulting mixture was stirred for 30 min at room temperature. After completion of the reaction, the mixture was quenched with aqueous $NH_4Cl$ and extracted with EtOAc (2×60 mL). The combined organic layers were washed with brine (1×50 mL), dried over $Na_2SO_4$, concentrated under reduced pressure and purified by column chromatography (Silica gel 100-200, 1:5, ethyl acetate/hexane) to give the desired product di-tert-butyl 1-(5-(methoxymethyl)thiazol-2-yl)hydrazine-1,2-dicarboxylate as a colorless oil (500 mg, 34.7% yield). LC-MS $(M+1)^+$: 360.

Step C. Synthesis of 2-hydrazinyl-5-(methoxymethyl)thiazole

To a solution of di-tert-butyl 1-(5-(methoxymethyl)thiazol-2-yl)hydrazine-1,2-dicarboxylate (100 mg, 0.28 mmol) in DCM (2 mL) was added TFA (1 mL). The reaction mixture was stirred at room temperature for 2 h. After completion of the reaction, the mixture was concentrated under reduced pressure to furnish the desired compound 2-hydrazinyl-5-(methoxymethyl)thiazole as a yellow solid (30 mg, 72.8% yield). $^1H$ NMR (400 MHZ, $CD_3OD$) δ: 6.97 (s, 1H), 4.45 (s, 2H), 3.34 (s, 3H); LC-MS $(M+1)^+$: 160.

Example 16

Synthesis of 3-hydrazinyl-5-(trifluoromethyl)-4H-1,2,4-triazole

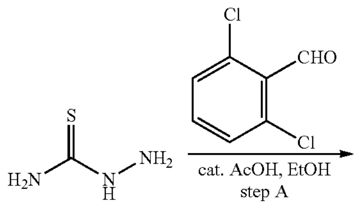

-continued

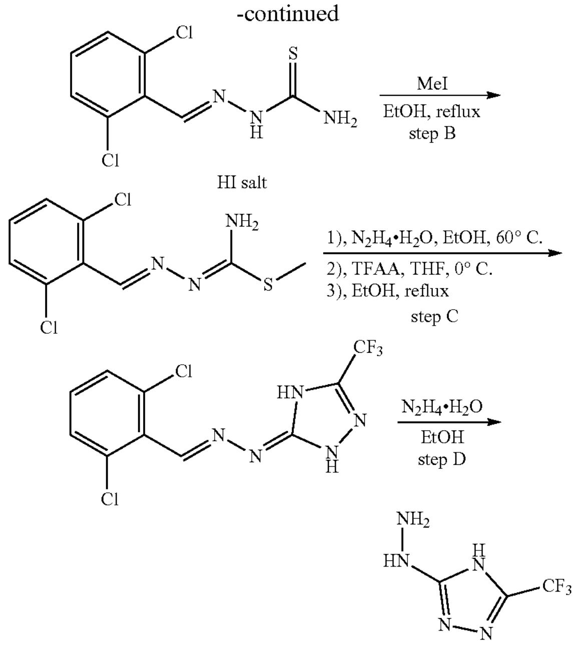

Step A. Synthesis of (E)-2-(2,6-dichlorobenzylidene)hydrazinecarbothioamide

To a stirred solution of 2,6-dichlorobenzaldehyde (1.74 g, 10 mmol) in EtOH (20 mL) was added hydrazinecarbothioamide (0.91 g, 10 mmol) and a drop of AcOH. The resulting mixture was heated to reflux and stirred for 6 hr. After cooling to 0° C., the resulting precipitates were collected by filtration, washed with PE and dried in vacuo to give the desired compound, (E)-2-(2,6-dichlorobenzylidene) hydrazinecarbothioamide, as a gray solid (2.3 g, 93% yield). LCMS $(M+1)^+$: 248.

Step B. Synthesis of (1E,N'E)-methyl N'-2,6-dichlorobenzylidenecarbamohydrazonothioate HI salt To a mixture of (E)-2-(2,6-dichlorobenzylidene)hydrazinecarbothioamide (1.8 g, 7.3 mmol) in EtOH (30 mL) was added MeI (1.14 g, 8 mmol). The resulting mixture was stirred at 65° C. under $N_2$ for 3 hr. The progress of the reaction was monitored by LCMS. After cooling to r.t, the reaction solution was concentrated in vacuo to dryness to give (1E,N'E)-methyl N'-2,6-dichlorobenzylidenecarbamohydrazonothioate HI salt as a yellow solid (2.85 g, 100% yield). LC-MS $(M+1)^+$: 262.0.

Step C. Synthesis of (E)-5-((E)-(2,6-dichlorobenzylidene)hydrazono)-3-(trifluoromethyl)-4,5-dihydro-1H-1,2,4-triazole To a mixture of (1E,N'E)-methyl N'-2,6-dichlorobenzylidenecarbamohydrazonothioate HI salt (390 mg, 1.0 mmol) in EtOH (10 mL) was added $N_2H_4{\cdot}H_2O$ (150 mg, 3 mmol). The resulting mixture was stirred at 60° C. under $N_2$ for 3 hr till LCMS showed most of starting material was converted into hydrazine substituted intermediate. After cooling to r.t, the reaction solution was concentrated in vacuo to dryness and then dissolved in THF (10 mL). TFAA (630 mg, 3 mmol) was added dropwise at 0° C. After the addition, the resulting mixture was stirred at r.t for 0.5 hr till LCMS showed the acylation was almost complete. Then, the mixture was concentrated in vacuo and the residue was diluted with EtOH (10 mL), followed by the addition of conc. $H_2SO_4$ (0.5 mL). The resulting solution was heated to reflux and stirred for 24 hr. After cooling to 0° C., the mixture was poured into ice water and extracted with EtOAc twice, the combined extracts were washed with brine, concentrated in vacuo and the residue was purified by column chromatography (Silica gel 60-120, 1:5, ethyl acetate/hexane) to give (E)-5-((E)-(2,6-dichlorobenzylidene)hydrazono)-3-(trifluoromethyl)-4,5-dihydro-1H-1,2,4-triazole as a white solid (60 mg, 18.6% yield). LC-MS $(M+1)^+$: 324.0.

Step D. Synthesis of 3-hydrazinyl-5-(trifluoromethyl)-4H-1,2,4-triazole

To a mixture of (E)-5-((E)-(2,6-dichlorobenzylidene)hydrazono)-3-(trifluoromethyl)-4,5-dihydro-1H-1,2,4-triazole (50 mg, 0.15 mmol) in EtOH (3 mL) was added $N_2H_4{\cdot}H_2O$ (46 mg, 0.9 mmol). The resulting mixture was stirred at 100° C. in a sealed tube for 14 hr till LCMS showed the completion of the reaction. After concentration in vacuo, the residue was purified by prep-HPLC to give the desired product 3-hydrazinyl-5-(trifluoromethyl)-4H-1,2,4-triazole as a pale yellow solid (6 mg, 24.1% yield). $^1H$ NMR (400 MHz, DMSO-$d_6$) δ: 8.11 (d, J=4.6 Hz, 2H), 4.52 (br, 2H); LC-MS $(M+1)^+$: 168.0.

Example 17

Synthesis of 3-(1-methylhydrazinyl)-1,2,4-oxadiazol-5(4H)-one

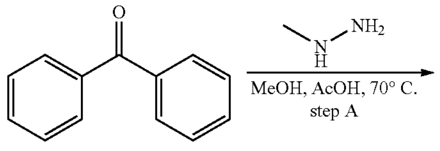

1

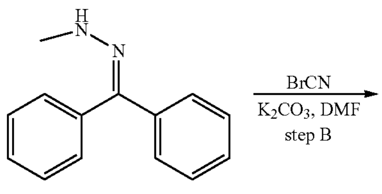

2

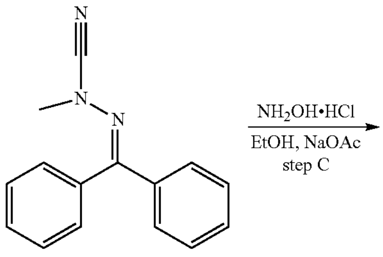

3

-continued

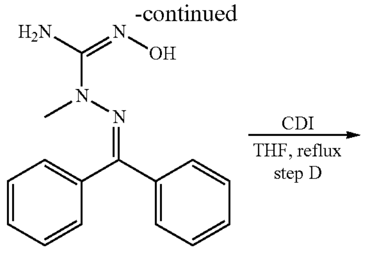

4

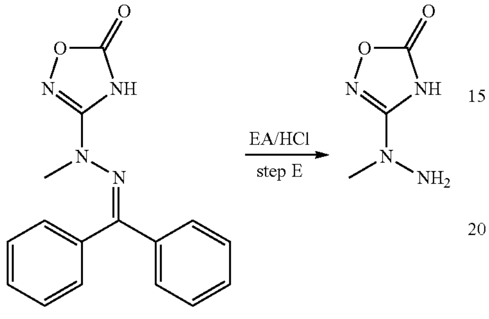

5

Step A. Synthesis of 1-(diphenylmethylene)-2-methylhydrazine

Methylhydrazine (17.4 mL, 0.33 mol) and glacial acetic acid (30 mL) were added to a solution of benzophenone (54.6 g, 0.30 mol) in methanol (100 mL). The mixture was heated at reflux for 2 h under a nitrogen atmosphere and then allowed to warm to room temperature. Half of the solvent was removed in vacuo. A saturated solution of $NaHCO_3$ was added and the mixture was extracted twice with EtOAc. The organic layer was dried with magnesium sulfate and concentrated in vacuo. Addition of a minimum amount of methanol and storage in the freezer gave, after a few days, light yellow crystals which were collected by filtration, washed with methanol and dried in vacuo to give 1-(diphenylmethylene)-2-methylhydrazine as a white solid (20.1 g, 32% yield). LCMS $(M+1)^+$: 211.

Step B. Synthesis of 2-(diphenylmethylene)-1-methylhydrazine-1-carbonitrile

To a mixture of 1-(diphenylmethylene)-2-methylhydrazine (0.9 g, 4.29 mmol) and $K_2CO_3$ (888 mg, 6.44 mmol) in DMF (10 mL) was added BrCN (683 mg, 6.44 mmol) in DCM at 0° C. Then the mixture was stirred at room temperature for 30 mins. The reaction mixture was diluted with water (50 mL) and extracted with DCM (2×50 mL). The combined organic layers were washed with brine (2×50 mL), dried over $Na_2SO_4$, concentrated under reduced pressure and purified by column chromatography (Silica gel 100-200, 1:4, ethyl acetate/hexane) to give 2-(diphenylmethylene)-1-methylhydrazine-1-carbonitrile as a colorless oil (750 mg, 74% yield). LCMS $(M+1)^+$: 236.

Step C. Synthesis of (Z)-2-(diphenylmethylene)-N'-hydroxy-1-methylhydrazine-1-carboximidamide To a mixture of 2-(diphenylmethylene)-1-methylhydrazine-1-carbonitrile (150 mg, 0.64 mmol) and hydroxylamine hydrochloride (66 mg, 0.96 mmol) in EtOH (3 ml) was added AcONa (78.7 mg, 0.96 mmol) at RT. Then the mixture was stirred at rt overnight. After completion of the reaction, the reaction mixture was extracted with EtOAc (2×50 mL). The combined organic layers were washed with brine (30 mL), died over anhydrous $Na_2SO_4$, filtered and concentrated under reduced pressure to give (Z)-2-(diphenylmethylene)-N'-hydroxy-1-methylhydrazine-1-carboximidamide (130 mg, 71% yield) as a white solid which was used in the next step without further purification. LCMS $(M+1)^+$: 269.

Step D. Synthesis of 3-(2-(diphenylmethylene)-1-methylhydrazinyl)-1,2,4-oxadiazol-5(4H)-one To a solution of (Z)-2-(diphenylmethylene)-N'-hydroxy-1-methylhydrazine-1-carboximidamide (130 mg, 0.49 mmol) in THF (3 ml) was added CDI (118 mg, 0.73 mmol). Then the mixture was stirred at 70° C. for 5 h. The reaction was concentrated under reduced pressure and purified by FCC to give 3-(2-(diphenylmethylene)-1-methylhydrazinyl)-1,2,4-oxadiazol-5(4H)-one (45 mg, 28% yield) as a white solid. LCMS $(M+1)^+$: 295.

Step E. Synthesis of 3-(1-methylhydrazinyl)-1,2,4-oxadiazol-5(4H)-one

A solution of 3-(2-(diphenylmethylene)-1-methylhydrazinyl)-1,2,4-oxadiazol-5(4H)-one (45 mg, 0.15 mmol) in 2 M HCl in EtOAc (10 ml) was stirred at rt overnight. The reaction was concentrated under reduced pressure and purified by Prep-HPLC to give 3-(1-methylhydrazinyl)-1,2,4-oxadiazol-5(4H)-one (10 mg, 50% yield) as a white solid. $^1H$ NMR (400 MHZ, DMSO-$d_6$) § 2.95 (s, 3H); LC-MS $(M+1)^+$: 131.1.

Example 18

Synthesis of 2-hydrazinyl-1,3,4-oxadiazole

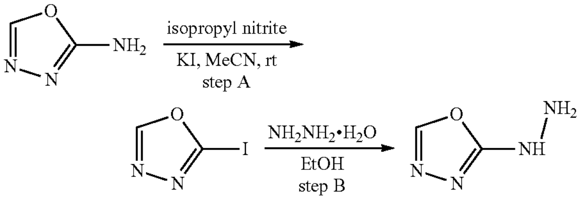

Step A. Synthesis of 2-iodo-1,3,4-oxadiazole

To a solution of 1,3,4-oxadiazol-2-amine (200 mg, 2.35 mmol) in MeCN (5 mL) was added isopropyl nitrite (419 mg, 4.70 mmol) and KI (781 mg, 4.70 mmol) at 0° C. The reaction solution was stirred at room temperature for 2 hrs. Then the reaction solution was concentrated and the residue was purified by column chromatography to afford 2-iodo-1,3,4-oxadiazole (150 mg, 33% yield) as a yellow oil. LC-MS $(M+1)^+$: 196.1

Step B. Synthesis of 2-hydrazinyl-1,3,4-oxadiazole

To a solution of 2-iodo-1,3,4-oxadiazole (30 mg, 0.16 mmol) in EtOH (3 mL) was added hydrazine hydrate (0.2 mL, 98%). The reaction solution was stirred at room temperature for 2 hrs. Then the reaction solution was concentrated to dryness and the residue was purified by Prep-HPLC to afford 2-hydrazinyl-1,3,4-oxadiazole (10 mg, 27% yield) as a white solid. $^1$H NMR (400 MHZ, DMSO-$d_6$) δ 8.54 (s, 1H), 8.47 (s, 1H), 4.42 (s, 2H); LCMS (M+1): 101.

Example 19

Synthesis of 2-hydrazinylthiazole-5-carbonitrile

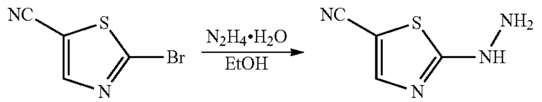

To a stirred solution of 2-bromothiazole-5-carbonitrile (50 mg, 0.27 mmol) in EtOH (5 mL) was added hydrazine hydrate (27 mg, 0.53 mmol) and stirred at 50° C. for 2 hrs. After completion of the reaction, the resulting mixture was concentrated and purified by Preparative HPLC to afford the desired compound, 2-hydrazinylthiazole-5-carbonitrile, as a solid (10 mg, 27% yield). $^1$H NMR (400 MHZ, DMSO-$d_6$) δ 9.78 (s, 1H), 7.88 (s, 1H), 5.34 (s, 2H); LCMS (M+1): 141.

Example 20

Synthesis of 2-hydrazinylthiazole-5-carboxylic Acid

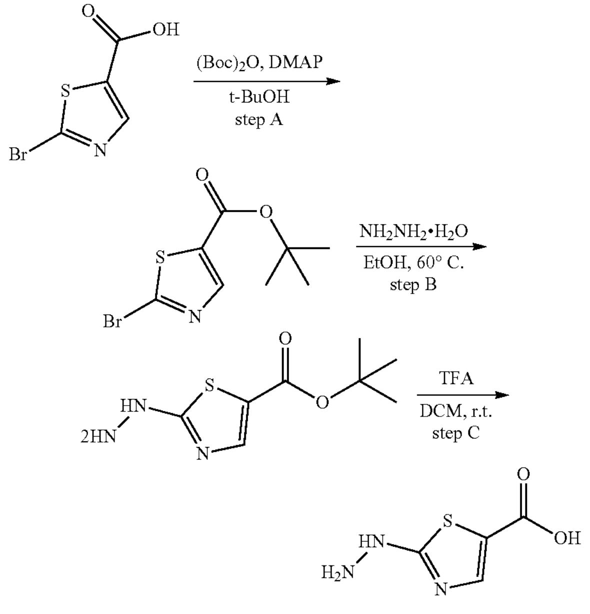

Step A. Synthesis of tert-butyl 2-bromothiazole-5-carboxylate

To a stirred solution of 2-bromothiazole-5-carboxylic acid (200 mg, 1.0 mmol) in t-BuOH (5 mL) was added $(Boc)_2O$ (220 mg, 1.0 mmol), followed by DMAP (47 mg, 0.39 mmol) at room temperature. The reaction mixture was stirred at 50° C. overnight. The reaction mixture was partitioned between EtOAc (30 mL) and water (30 mL). The organic phase was washed with brine (20 mL), dried over $Na_2SO_4$, concentrated under reduced pressure and purified by column chromatography (Silica gel 100-200, 1:100, ethyl acetate/hexane) to give the desired product tert-butyl 2-bromothiazole-5-carboxylate as a yellow oil (100 mg, 38.1% yield). LC-MS $(M+1)^+$: 264.

Step B. Synthesis of tert-butyl 2-hydrazinylthiazole-5-carboxylate

To a stirred solution of tert-butyl 2-bromothiazole-5-carboxylate (50 mg, 0.17 mmol) in EtOH (3 mL) was added Hydrazinium hydroxide (34.1 mg, 0.68 mmol). The reaction mixture was stirred at 60° C. overnight. The reaction mixture was partitioned between EtOAc (10 mL) and water (10 mL). The organic phase was washed with brine (10 mL), dried over $Na_2SO_4$, concentrated under reduced pressure and purified by column chromatography (Silica gel 100-200, 1:1, ethyl acetate/hexane) to give the desired product tert-butyl 2-hydrazinylthiazole-5-carboxylate as a white solid (15 mg, 40.8% yield). LC-MS $(M+1)^+$: 216.

Step C. Synthesis of 2-hydrazinylthiazole-5-carboxylic Acid

To a stirred solution of tert-butyl 2-hydrazinylthiazole-5-carboxylate (15 mg, 0.07 mmol) in DCM (3 mL) was added TFA (1 mL). The reaction mixture was stirred at room temperature overnight and concentrated under reduced pressure to give the desired compound 2-hydrazinylthiazole-5-carboxylic acid (9 mg, 82.0% yield) as yellow solid. $^1$H NMR (400 MHz, DMSO-$d_6$) δ: 9.31 (brs, 1H), 7.67 (s, 1H), 5.17 (brs, 1H); LC-MS $(M+1)^+$: 160.

Example 21

Synthesis of 5-hydrazinyl-4H-1,2,4-triazol-3-ol

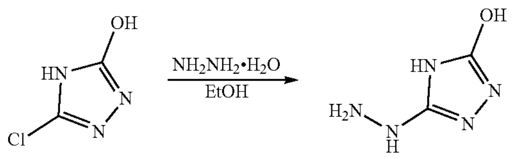

To a stirred solution of 5-chloro-4H-1,2,4-triazol-3-ol (20 mg, 0.17 mmol) in EtOH (1 mL) was added Hydrazine hydrate (1 mL). The reaction mixture was stirred at 80° C. for 3 h and concentrated under reduced pressure to give the desired compound 5-hydrazinyl-4H-1,2,4-triazol-3-ol (8.7 mg, 45.0% yield) as yellow solid. $^1$H NMR (400 MHZ, DMSO-$d_6$) δ 10.27 (s, 1H), 6.87 (m, 1H), 4.03 (brs, 2H); LC-MS $(M+1)^+$: 116.

Example 22

Synthesis of 5-hydrazinyl-2-methyloxazole-4-carbonitrile

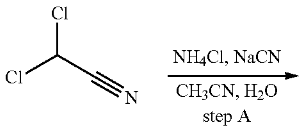

-continued

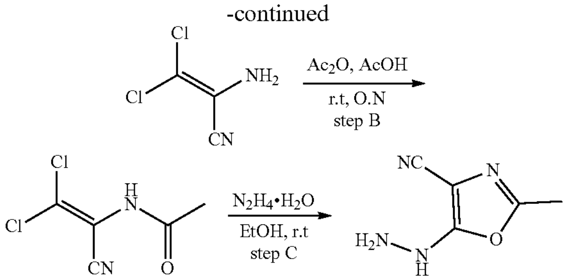

Step A. Synthesis of 2-amino-3,3-dichloroacrylonitrile

To a stirred solution of 2,2-dichloroacetonitrile (500 mg, 4.59 mmol) in $CH_3CN$ (10 mL), water (2 mL) was added $NH_4Cl$ (486 mg, 9.17 mmol) and NaCN (450 mg, 9.17 mmol) and stirred at room temperature for 16 h. After completion of the reaction, the mixture was concentrated and washed with water to afford 2-amino-3,3-dichloroacrylonitrile (560 mg, 80% yield) as a white solid. LCMS (M+1): 137.

Step B. Synthesis of N-(2,2-dichloro-1-cyanovinyl)acetamide

To a stirred solution of 2-amino-3,3-dichloroacrylonitrile (560 mg, 4.12 mmol) in HOAc (5 mL) was added Acetic anhydride (504 mg, 4.94 mmol) at room temperature and stirred for 16 h. After completion of the reaction, the mixture was quenched with $NaHCO_3$ solution and extracted with EtOAc (2×50 mL). The combined organic layers were concentrated under reduced pressure and purified by chromatography column to afford N-(2,2-dichloro-1-cyanovinyl) acetamide (500 mg, 68.2% yield) as a white solid. LCMS (M+1): 179.

Step C. Synthesis of 5-hydrazinyl-2-methyloxazole-4-carbonitrile

To a stirred solution of N-(2,2-dichloro-1-cyanovinyl) acetamide (500 mg, 2.81 mmol) in EtOH (5 mL) was added hydrazine hydrate (281 mg, 5.62 mmol) at room temperature and stirred for 4 h. After completion of the reaction, the mixture was concentrated and purified by preparative HPLC to furnish the desired compound, 5-hydrazinyl-2-methyloxazole-4-carbonitrile (100 mg, 26% yield) as a white solid. $^1H$ NMR (400 MHZ, DMSO-$d_6$) δ 8.88 (brs, 1H), 4.72 (brs, 2H), 2.22 (s, 3H). LCMS (M+1): 138.

Example 23

Synthesis of (2-hydrazinylthiazol-4-yl)methanol

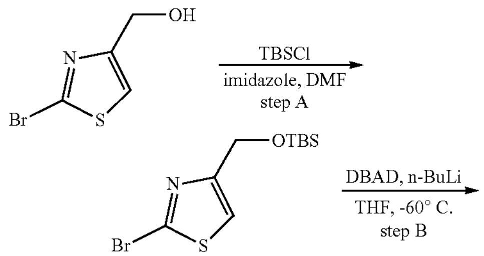

-continued

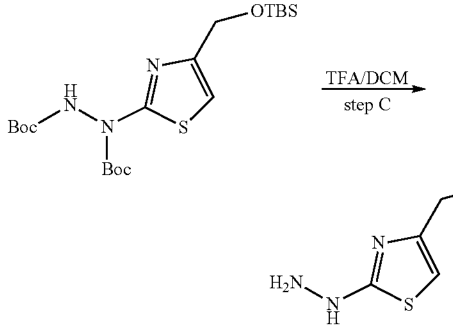

Step A. Synthesis of 2-bromo-4-(((tert-butyldimethylsilyl)oxy)methyl)thiazole

To a stirred solution of (2-bromothiazol-4-yl)methanol (500 mg, 2.59 mmol) in DMF (10 mL) was added imidazole (530 mg, 7.77 mmol), followed by TBSCl (590 mg, 3.89 mmol) at room temperature. Then the reaction mixture was stirred at room temperature for 30 min. The reaction mixture was diluted with water (30 mL) and extracted with ethyl acetate (2×40 mL). The combined organic layers were washed with brine (2×40 mL), dried over $Na_2SO_4$, concentrated under reduced pressure and purified by column chromatography (Silica gel 100-200, 100:1, ethyl acetate/hexane) to give the desired product 2-bromo-4-(((tert-butyldimethylsilyl)oxy)methyl)thiazole as a colorless oil (400 mg, 50% yield). LCMS (M+1): 308.

Step B. Synthesis of di-tert-butyl 1-(4-(((tert-butyldimethylsilyl)oxy)methyl)thiazol-2-yl)hydrazine-1,2-dicarboxylate To a solution of 2-bromo-4-(((tert-butyldimethylsilyl)oxy)methyl)thiazole (200 mg, 0.65 mmol) in anhydrous THF (10 mL) was added n-BuLi (0.3 mL, 0.71 mmol, 2.5 M in THF) dropwise under $N_2$ atmosphere at −60° C. Then the mixture was stirred at this temperature for 30 mins. A solution of DBAD (230 mg, 0.98 mmol) in THF was added dropwise at −60° C. The resulting mixture was stirred at −60° C. for 30 mins. The mixture was quenched with aqueous $NH_4Cl$ and extracted with ethyl acetate (2×50 mL). The combined organic layers were washed with brine (1×40 mL), dried over $Na_2SO_4$, concentrated under reduced pressure and purified by column chromatography (Silica gel 100-200, 3:1, ethyl acetate/hexane) to give the desired product di-tert-butyl 1-(4-(((tert-butyldimethylsilyl)oxy)methyl)thiazol-2-yl)hydrazine-1,2-dicarboxylate as a yellow oil (150 mg, 50% yield). LCMS (M+1): 460.

Step B. Synthesis of (2-hydrazinylthiazol-4-yl)methanol

To a solution of di-tert-butyl 1-(4-(((tert-butyldimethylsilyl)oxy)methyl)thiazol-2-yl)hydrazine-1,2-dicarboxylate (70 mg, 0.15 mmol) in DCM (2 mL) was added TFA (0.5 mL). The mixture was stirred at room temperature for 16 hrs and concentrated under reduced pressure. The residue was purified by prep-HPLC to give desired product (2-hydrazinylthiazol-4-yl)methanol as a yellow oil (4 mg, 19.1% yield). $^1H$ NMR (400 MHz, $CD_3OD$) δ: 6.52 (s, 1H), 4.46 (s, 2H); LCMS (M+1): 146.

Example 24

Synthesis of 2-hydrazinyl-4-methylthiazole-5-carboxylic Acid

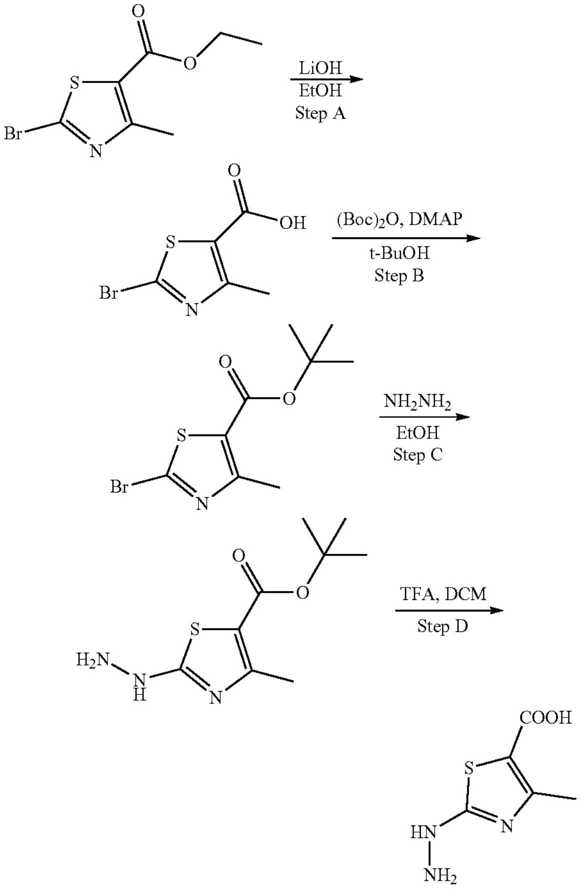

Step A. Synthesis of 2-bromo-4-methylthiazole-5-carboxylic acid

To a solution of ethyl 2-bromo-4-methylthiazole-5-carboxylate (500 mg, 2 mmol) in EtOH (10 mL) and water (1 mL) was added LiOH (479 mg, 20 mmol), The resulting mixture was stirred at room temperature for 3 hrs. The mixture was neutralized with 1 N HCl, extracted with EtOAc (60 mL). The organic phase was washed with brine (20 mL×2), dried over $Na_2SO_4$, filtered, concentrated to afford 2-bromo-4-methylthiazole-5-carboxylic acid (320 mg, 69% yield) as a white solid. LCMS (M+1): 223.

Step B. Synthesis of tert-butyl 2-bromo-4-methylthiazole-5-carboxylate

To a solution of 2-bromo-4-methylthiazole-5-carboxylic acid (80 mg 0.36 mmol) in t-BuOH (10 mL) was added $(Boc)_2O$ (157 mg 0.72 mmol) and DMAP (13 mg, 0.108 mmol). The reaction mixture was stirred at 30° C. for 3 hrs. The reaction mixture was partitioned between EtOAc (50 mL) and water (15 mL). The organic layer was washed with brine (20 mL), dried over $Na_2SO_4$, filtered, concentrated to dryness and the residue was purified by by flash column chromatography on silica gel (PE/EA=12:1) to afford tert-butyl 2-bromo-4-methylthiazole-5-carboxylate (40 mg, 39.7% yield) as a white solid. LCMS (M+1): 279.

Step C. Synthesis of tert-butyl 2-hydrazinyl-4-methylthiazole-5-carboxylate

To a solution of Tert-butyl 2-bromo-4-methylthiazole-5-carboxylate (40 mg, 0.143 mmol) in EtOH (3 mL) was added $NH_2NH_2H_2O$ (0.1 mL). The resulting mixture and stirred at 70° C. for 16 hrs. The reaction mixture was evaporated to dryness and the residue was purified by flash column chromatography on silica gel (PE/EA=3:1) to afford tert-butyl 2-hydrazinyl-4-methylthiazole-5-carboxylate (20 mg, 61% yield) as a white solid. LCMS (M+1): 230.

Step D. Synthesis of 4-((1-(aminooxy)cyclobutane-1-carbonyl)oxy)butanoicacid To a solution of tert-butyl 2-hydrazinyl-4-methylthiazole-5-carboxylate (20 mg, 0.087 mmol) in DCM (2 mL) was added TFA (2 mL). The resulting mixture was stirred at room temperature for 2 h. The reaction solution was then evaporated to afford to 4-((1-(aminooxy)cyclobutane-1-carbonyl)oxy)butanoicacid (15 mg, 99% yield) as a white solid. $^1H$ NMR (400 MHZ, DMSO-$d_6$) δ 10.16-9.61 (m, 1H), 2.41 (s, 3H); LCMS (M+1): 174.

Example 25

Synthesis of 5-hydrazinyl-1-methyl-1H-tetrazole

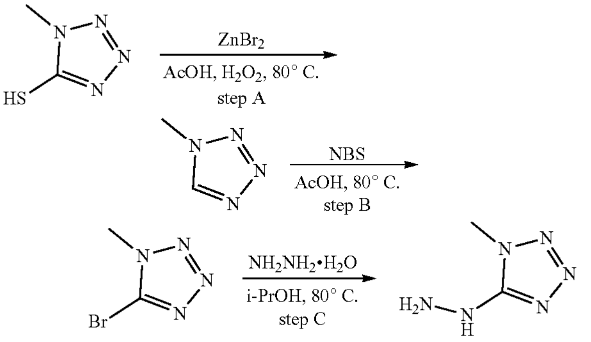

Step A. Synthesis of 1-methyl-1H-tetrazole

To a stirred solution of 1-methyl-1H-tetrazole-5-thiol (500 mg, 4.3 mmol) in AcOH (10 mL) was added $ZnBr_2$ (1.9 g, 8.6 mmol) at 40° C. Then $H_2O_2$ (975 mg, 8.6 mmol, wt=30%) was added to the mixture dropwise. The reaction mixture was stirred at 80° C. overnight. Then the reaction mixture was quenched with water (30 mL) and extracted with ethyl acetate (2×40 mL). The combined organic layers were washed with brine (1×40 mL), dried over $Na_2SO_4$, concentrated under reduced pressure to give the desired compound 1-methyl-1H-tetrazole (50 mg, 13.8% yield) as a white solid which was used in the next step without further purification. $^1H$ NMR (400 MHZ, DMSO-$d_6$) δ: 9.48 (s, 1H), 4.21 (s, 3H); LC-MS $(M+1)^+$: 85.

Step B. Synthesis of 5-bromo-1-methyl-1H-tetrazole

To a stirred solution of 1-methyl-1H-tetrazole (50 mg, 0.60 mmol) in AcOH (5 mL) was added NBS (127 mg, 0.71 mmol). The reaction mixture was stirred at 80° C. overnight and concentrated under reduced pressure. The residue was purified by column chromatography (Silica gel 100-200, 1:3, ethyl acetate/hexane) to give the desired product 5-bromo-1-methyl-1H-tetrazole as a white solid (30 mg, 31.1% yield). $^1$H NMR (400 MHZ, DMSO-$d_6$) δ: 4.05 (s, 3H); LC-MS $(M+1)^+$: 163.

Step C. Synthesis of 5-hydrazinyl-1-methyl-1H-tetrazole

To a stirred solution of 5-bromo-1-methyl-1H-tetrazole (30 mg, 0.186 mmol) in iPrOH (1 mL) was added Hydrazine hydrate (1 ml). The reaction mixture was stirred at 80° C. overnight. The reaction mixture was partitioned between EtOAc (10 mL) and water (10 mL). The liquid phase was concentrated to give the desired compound 5-hydrazinyl-1-methyl-1H-tetrazole (7.3 mg, 34.4% yield) as yellow solid. $^1$H NMR (400 MHZ, DMSO-$d_6$) δ: 8.96 (brs, $^1$H), 4.12 (d, J=4.0 Hz, 1H), 2.24 (s, 3H); LC-MS $(M+1)^+$: 115.

Example 26

Synthesis of 2-(1-(1H-tetrazol-5-yl)hydrazinyl)ethan-1-ol

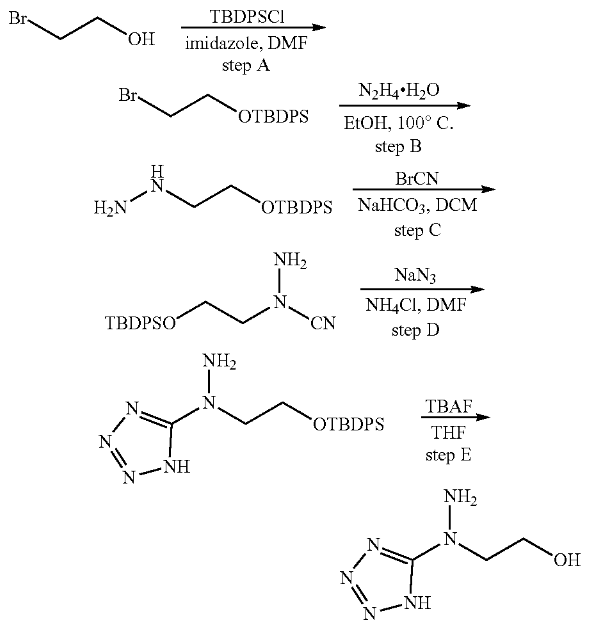

Step A. Synthesis of (2-bromoethoxy)(tert-butyl)diphenylsilane

A solution of 2-bromoethan-1-ol (1.0 g, 8.0 mmol), imidazole (1.1 g, 16.0 mmol) and TBDPSCl (2.42 g, 8.8 mmol) in DMF (20 mL) was stirred at room temperature for 8 h. The reaction mixture was diluted with water (80 mL) and extracted with ethyl acetate (2×80 mL). The combined organic layers were washed with brine (2×80 mL), dried over $Na_2SO_4$, concentrated under reduced pressure and purified by column chromatography (Silica gel 100-200, 100:1, ethyl acetate/hexane) to give the desired product (2-bromoethoxy)(tert-butyl)diphenylsilane as a colorless oil (3.0 g, 95% yield). LCMS $(M+1)^+$: 363.

Step B. Synthesis of (2-((tert-butyldiphenylsilyl)oxy)ethyl)hydrazine

A solution of (2-bromoethoxy)(tert-butyl)diphenylsilane (3.0 g, 8.3 mmol) and $N_2H_4 \cdot H_2O$ (5.3 g, 82.8 mmol, wt: 80% in $H_2O$) in EtOH (10 mL) was stirred at 100° C. for 16 h. The reaction mixture was diluted with aqueous $NaHCO_3$ (80 mL) and extracted with DCM (2×80 mL). The combined organic layers were washed with brine (2×80 mL), dried over $Na_2SO_4$, concentrated under reduced pressure and purified by column chromatography (Silica gel 100-200, 1:1, ethyl acetate/hexane) to give the desired product (2-((tert-butyldiphenylsilyl)oxy)ethyl)hydrazine as a yellow oil (1.4 g, 42% yield). LCMS $(M+1)^+$: 315.

Step C. Synthesis of (2-((tert-butyldiphenylsilyl)oxy)ethyl)hydrazine

To a mixture of (2-((tert-butyldiphenylsilyl)oxy)ethyl)hydrazine (1.4 g, 4.5 mmol) and aqueous $NaHCO_3$ (750 mg, 8.9 mmol, 2 mmol/mL) in DCM (10 mL) was added BrCN (470 mg, 4.5 mmol) in DCM at 0° C. Then the mixture was stirred at room temperature for 30 mins. The reaction mixture was diluted with water (50 mL) and extracted with DCM (2×50 mL). The combined organic layers were washed with brine (2×50 mL), dried over $Na_2SO_4$, concentrated under reduced pressure and purified by column chromatography (Silica gel 100-200, 1:2, ethyl acetate/hexane) to give the desired product 1-(2-((tert-butyldiphenylsilyl)oxy)ethyl)hydrazine-1-carbonitrile as a colorless oil (900 mg, 60% yield). LCMS $(M+1)^+$: 340.

Step D. Synthesis of 5-(1-(2-((tert-butyldiphenylsilyl)oxy)ethyl)hydrazinyl)-1H-tetrazole A mixture of 1-(2-((tert-butyldiphenylsilyl)oxy)ethyl)hydrazine-1-carbonitrile (950 mg, 2.8 mmol), $NH_4Cl$ (450 mg, 8.4 mmol) and $NaN_3$ (365 mg, 5.6 mmol) in DMF (10 mL) was stirred at 90° C. for 16 h. After completion of the reaction, aqueous critic acid solution was added and extracted with ethyl acetate (2×30 mL). The combined organic layers were washed with brine (1×30 mL), dried over $Na_2SO_4$, concentrated under reduced pressure and purified by prep-HPLC to give the desired compound 5-(1-(2-((tert-butyldiphenylsilyl)oxy)ethyl)hydrazinyl)-1H-tetrazole as a white solid (350 mg, 35% yield). LCMS $(M+1)^+$: 383.

Step D. Synthesis of 2-(1-(1H-tetrazol-5-yl)hydrazinyl)ethan-1-ol

To a solution of 5-(1-(2-((tert-butyldiphenylsilyl)oxy)ethyl)hydrazinyl)-1H-tetrazole (350 mg, 0.92 mmol) in THF was added TBAF (1 mL, 1.0 mmol, 1.0 M in THF). Then the mixture was stirred at room temperature for 2 h. Then the mixture was concentrated under reduced pressure and purified by prep-HPLC to give the desired product 2-(1-(1H-tetrazol-5-yl)hydrazinyl)ethan-1-ol as a white solid (50 mg, 35% yield). $^1$H NMR (400 MHZ, DMSO-$d_6$) δ: 8.37 (s, 1H), 3.66 (t, J=6.0 Hz, 1H), 3.49 (t, J=6.0 Hz, 1H); LCMS $(M+1)^+$: 145.

Example 27

Synthesis of tert-butyl ethyl 2-hydrazinyl-4-methylthiazole-5-carboxylate

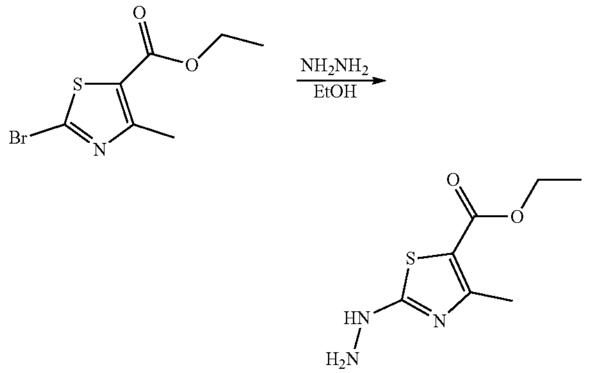

To a solution of ethyl 2-bromo-4-methylthiazole-5-carboxylate (500 mg, 2 mmol) in EtOH (20 mL) was added Hydrazine hydrate (0.5 mL). The resulting mixture and stirred at 70° C. for 16 hrs. The reaction mixture was evaporated to dryness and the residue was purified by flash column chromatography on silica gel (PE/EA=3:1) to afford tert-butyl ethyl 2-hydrazinyl-4-methylthiazole-5-carboxylate (200 mg, 50% yield) as a white solid. $^1$H NMR (400 MHZ, DMSO-$d_6$) δ 9.27 (s, 1H), 5.05 (s, 2H), 4.14 (d, J=7.1 Hz, 2H), 2.37 (s, 3H), 1.23 (t, J=7.1 Hz, 3H); LCMS $(M+1)^+$: 202.

Example 28

Synthesis of 5-(1-propylhydrazinyl)-1H-tetrazole

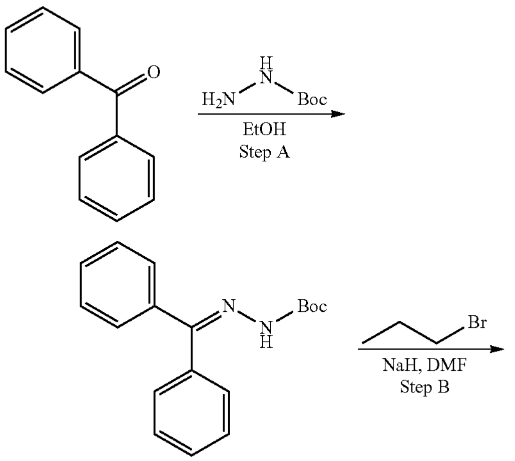

-continued

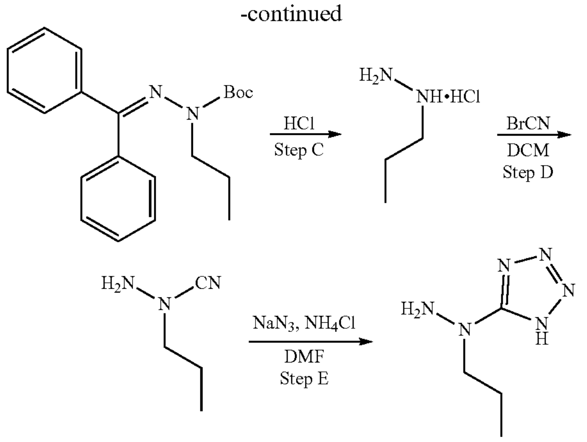

Step A. Synthesis of tert-butyl 2-(diphenylmethylene)hydrazinecarboxylate

The mixture of benzophenon (2.0 g, 10.9 mmol), tert-butyl hydrazinecarboxylate (1.45 g, 10.9 mmol) and AcOH (1 ml) in EtOH (10 ml) was heated at 50° C. for 2 h. The mixture was concentrated to remove solvent, then the residue was purified by column chromatography to give tert-butyl 2-(diphenylmethylene)hydrazinecarboxylate as a white solid (3.0 g, 93.0% yield). LCMS $(M+1)^+$: 297.

Step B. Synthesis of tert-butyl 2-(diphenylmethylene)-1-propylhydrazine carboxylate To a solution of tert-butyl 2-(diphenylmethylene)hydrazinecarboxylate (500 mg, 1.68 mmol) in DMF (3 mL) was added NaH (101 mg, 2.53 mmol) at 0° C. for 5 min, then 1-bromopropane (311 mg, 2.53 mmol) was added to the solution. The solution was stirred at 50° C. for 2 h. The solution was poured into ice water and extracted with EtOAc twice. The combined organic phase was washed with brine, dried over $NaSO_4$, concentrated and purified by column chromatography to give tert-butyl 2-(diphenylmethylene)-1-propylhydrazinecarboxylate (550 mg, 96.8% yield). LCMS $(M+1)^+$: 339.

Step C. Synthesis of Propylhydrazine Hydrochloride

A solution of tert-butyl 2-(diphenylmethylene)-1-propylhydrazinecarboxylate (3 g, 8.87 mmol) in MeOH (30 mL) was added con. HCl (10 ml) was stirred at r.t for 1 h. The mixture was concentrated to remove solvent and EtOAc was added to the mixture. The mixture was stirred for 10 min, then filtrated to give propylhydrazine hydrochloride as a white solid (810 mg, 83.0% yield). LCMS $(M+1)^+$: 75.

Step D. Synthesis of 1-propylhydrazinecarbonitrile

To a solution of propylhydrazine hydrochloride (500 mg, 4.54 mmol) in DCM was added a solution of $Na_2CO_3$ (1.25 g, 9.08 mmol) and BrCN (481 mg, 4.54 mmol) in $H_2O$ (5 ml) slowly at 0° C., then the mixture was stirred at 0° C. for 1 h. The mixture was added $H_2O$ and extracted with DCM twice, then the combined organic phase was concentrated to afford 1-propylhydrazinecarbonitrile (300 mg, 67% yield) as a yellow oil. LCMS $(M+1)^+$: 100.

Step D. Synthesis of 5-(1-propylhydrazinyl)-1H-tetrazole

To a solution of 1-propylhydrazinecarbonitrile (300 mg, 3.03 mmol) in DMF (3 mL) was added $NaN_3$ (196 mg, 3.03 mmol) and $NH_4Cl$ (160 mg, 3.03 mmol). Then the mixture was heated at 90° C. for 2 h. The mixture was filtrated and the filtrate was concentrated to removed solvent, then purified by $Al_2O_3$ column chromatography (DCM/MeOH/$NH_3 \cdot H_2O$=4/1/0.2) to give 5-(1-propylhydrazinyl)-1H-tetrazole (150 mg, 34.8% yield) as a white solid. $^1H$ NMR (400 MHZ, DMSO-$d_6$) δ 3.41 (t, J=7.2 Hz, 2H), 2.50 (dt, J=7.2 Hz, 7.6 Hz, 1H), 0.87 (t, J=7.2 Hz, 3H); LCMS $(M+1)^+$: 143.

Example 29

Synthesis of 5-(1-cyclopropylhydrazinyl)-1H-tetrazole

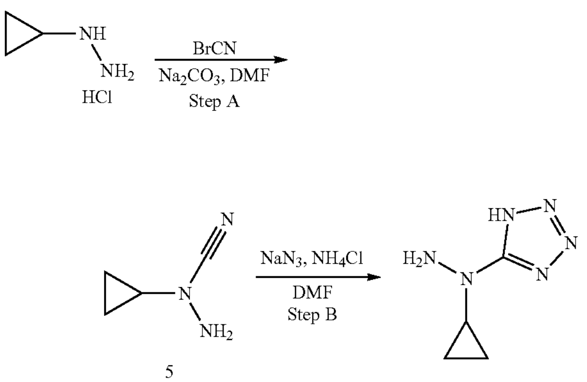

5

Step A. Synthesis of 1-cyclopropylhydrazine-1-carbonitrile

To a solution of cyclopropylhydrazine hydrochloride (300 mg, 2.76 mmol) in DMF (3 mL) was added a $Na_2CO_3$ (439 mg, 4.14 mmol) and BrCN (439 mg, 4.14 mmol) slowly at 0° C., then the mixture was stirred at rt for 1 h. The mixture was added $H_2O$ and extracted with DCM twice, then the combined organic phase was concentrated to afford 1-cyclopropylhydrazine-1-carbonitrile (150 mg, 56% yield) as a yellow oil. LCMS $(M+1)^+$: 98.

Step B. Synthesis of 5-(1-cyclopropylhydrazinyl)-1H-tetrazole

To a solution of 1-cyclopropylhydrazine-1-carbonitrile (150 mg, 1.55 mmol) in DMF (3 mL) was added $NaN_3$ (202 mg, 3.10 mmol) and $NH_4Cl$ (166 mg, 3.10 mmol). Then the mixture was heated at 90° C. for 2 h. The mixture was filtrated and the filtrate was concentrated to removed solvent, then purified by Prep-HPLC to give 5-(1-cyclopropylhydrazinyl)-1H-tetrazole (10 mg, 5% yield) as a white solid. $^1H$ NMR (400 MHZ, DMSO-$d_6$) δ 4.99 (s, 2H), 2.83-2.80 (m, 1H), 0.80-0.71 (m, 4H); LCMS $(M+1)^+$: 141.1.

Example 30

Synthesis of 5-(1-isopropylhydrazinyl)-1H-tetrazole

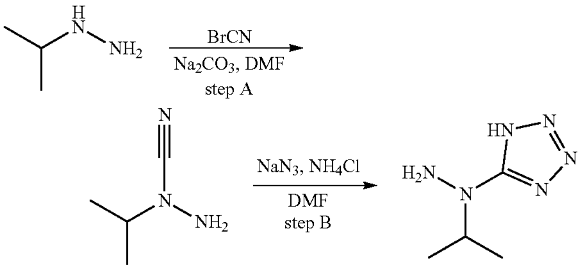

Step A. Synthesis of 1-isopropylhydrazine-1-carbonitrile

To a solution of isopropylhydrazine (3.0 g, 40.47 mmol) in DMF (4 mL) was added a $Na_2CO_3$ (6.4 g, 60.70 mmol) and BrCN (6.4 g, 60.70 mmol) slowly at 0° C., then the mixture was stirred at rt for 3 h. The mixture was added $H_2O$ and extracted with DCM twice, then the combined organic phase was concentrated to afford 1-isopropylhydrazine-1-carbonitrile (1.4 g, 35% yield) as a yellow oil. LCMS $(M+1)^+$: 101.1.

Step B. Synthesis of 5-(1-isopropylhydrazinyl)-1H-tetrazole

To a solution of 1-isopropylhydrazine-1-carbonitrile (300 mg, 3.03 mmol) in DMF (3 mL) was added $NaN_3$ (394 mg, 6.06 mmol) and $NH_4Cl$ (324 mg, 6.06 mmol). Then the mixture was heated at 90° C. for 2 h. The mixture was filtrated and the filtrate was concentrated to removed solvent, then purified by Prep-HPLC to afford 5-(1-isopropylhydrazinyl)-1H-tetrazole (50 mg, 12% yield) as a white solid. $^1H$ NMR (400 MHZ, DMSO-$d_6$) δ 14.53 (s, 1H), 4.60 (s, 2H), 4.22-4.15 (m, 1H), 1.11 (d, J=6.4 Hz, 6H); LCMS $(M+1)^+$: 143.1.

Example 31

Synthesis of 5-(1-ethylhydrazinyl)-1H-tetrazole

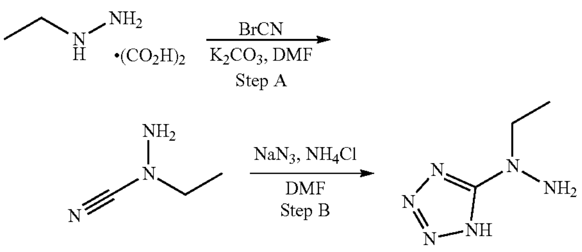

Step A. Synthesis of 1-ethylhydrazine-1-carbonitrile

To a solution of cyanogen bromide (500 mg, 4.72 mmol) in DMF (10 mL) was added ethylhydrazine Oxalate (709 mg, 4.72 mmol) and sodium carbonate (1.50 g, 14.16 mmol)

at 0° C. The reaction mixture was stirred at this temperature for 3 h. Then diluted with EtOAc (60 mL). The organic phase was washed with water (15 mL) and brine (15 mL), dried over $Na_2SO_4$, filtered, concentrated to dryness and the residue was purified by flash column chromatography on silica gel (EtOAc/PE=1:1) to afford 1-ethylhydrazine-1-carbonitrile (300 mg, 75% yield) as a colorless oil. LCMS $(M+1)^+$: 86.

Step B. Synthesis of 5-(1-ethylhydrazinyl)-1H-tetrazole

A mixture of 1-ethylhydrazine-1-carbonitrile (300 mg, 3.52 mmol), sodium azide (458 mg, 7.05 mmol) and ammonium chloride (566 mg, 10.57 mmol) in DMF (6 mL) was stirred at 90° C. for 1 h. The resulting mixture was filtered and evaporated. The residue was purified by Prep-TLC ($DCM:MeOH:NH_3OH$=4:1:0.2) to afford 5-(1-ethylhydrazinyl)-1H-tetrazole (25 mg, 5.54% yield) as a white solid. $^1H$ NMR (400 MHZ, DMSO-$d_6$) δ 3.48 (q, J=8.0 Hz, 2H), 1.14 (t, J=8.0 Hz, 3H). LCMS $(M+1)^+$: 129.

Example 32

Synthesis of 3-(1-(1H-tetrazol-5-yl)hydrazinyl)propan-1-ol

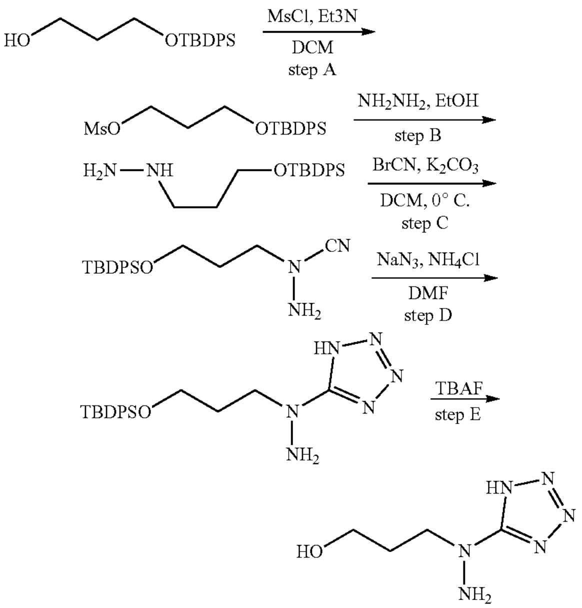

Step A. Synthesis of 3-((tert-butyldiphenylsilyl)oxy)propyl methanesulfonate To a solution of 3-((tert-butyldiphenylsilyl)oxy)propan-1-ol (7.0 g, 22.26 mmol) in DCM (50 mL) was added $Et_3N$ (3.37 g, 33.39 mmol) and MsCl (2.8 g, 24.48 mmol) at 0° C. The reaction mixture was stirred at rt for 3 h. The mixture was washed with $H_2O$ and extracted with EtOAc. Evaporated and purified by flash chromatography (Silica gel 60-120, ethyl acetate/hexane=1:4) to afford 3-((tert-butyldiphenylsilyl)oxy)propyl methanesulfonate as a yellow oil (8.0 g, 92% yield). LCMS $(M+1)^+$: 393.

Step B. Synthesis of (3-((tert-butyldiphenylsilyl)oxy)propyl)hydrazine

To a solution of 3-((tert-butyldiphenylsilyl)oxy)propyl methanesulfonate (8.0 g, 25 mmol) in ethanol (15 mL) was added hydrazine monohydrate (15 mL) and the mixture was heated to 60° C. for 2 h then concentrated to afford (3-((tert-butyldiphenylsilyl)oxy)propyl)hydrazine (5.0 g, 75% yield). LCMS $(M+1)^+$: 329.

Step C. Synthesis of 1-(3-((tert-butyldiphenylsilyl)oxy)propyl)hydrazine-1-carbonitrile The solution of BrCN (2.42 g, 22.83 mmol) in DCM (20 ml) was cooled to 0° C., A mixture of (3-((tert-butyldiphenylsilyl)oxy)propyl)hydrazine (5.0 g, 15.22 mmol), $Na_2CO_3$ (2.42 g, 22.83 mmol) and 10 ml $H_2O$ was added dropwise under vigorous stirring for 1 h. The solution was extracted with DCM, concentrated and purified by column chromatography to give 1-(3-((tert-butyldiphenylsilyl)oxy)propyl) hydrazinecarbonitrile as a yellow oil (3.5 g, 65% yield). LCMS $(M+1)^+$: 354.

Step D. Synthesis of 5-(1-(3-((tert-butyldiphenylsilyl)oxy)propyl)hydrazinyl)-1H-tetrazole To a solution of 1-(3-((tert-butyldiphenylsilyl)oxy)propyl)hydrazinecarbonitrile (0.5 g, 1.41 mmol) in DMF (5 mL) was added $NaN_3$ (92 mg, 1.41 mmol) and $NH_4Cl$ (75 mg, 1.41 mmol). Then the reaction mixture was heated at 90° C. for 1.5 h. The mixture was filtrated, the filtrate was concentrated. The residue was purified by column chromatography to give 5-(1-(3-((tert-butyldiphenylsilyl)oxy)propyl)hydrazinyl)-1H-tetrazole as a white solid (180 mg, 32% yield). LC-MS $(M+1)^+$: 397.

Step E. Synthesis of 3-(1-(1H-tetrazol-5-yl)hydrazinyl)propan-1-ol

To a solution of 5-(1-(3-((tert-butyldiphenylsilyl)oxy)propyl)hydrazinyl)-1H-tetrazole (100 mg, 0.25 mmol) in THF (3 mL) was added TBAF (0.5 mL, 1 M) and then stirred overnight at rt. The mixture was evaporated and purified by Prep-HPLC to afford 3-(1-(1H-tetrazol-5-yl)hydrazinyl)propan-1-ol (10 mg, 25% yield). $^1H$ NMR (400 MHZ, $D_2O$) 8: 3.61 (t, J=6.4 Hz, 2H), 3.22 (t, J=7.2 Hz, 2H), 1.77-1.73 (m, 2H); LC-MS $(M+1)^+$: 159.

Example 33

Synthesis of 4-(1-(1H-tetrazol-5-yl)hydrazinyl)butan-1-ol

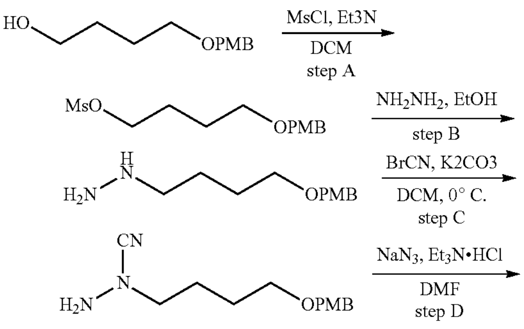

-continued

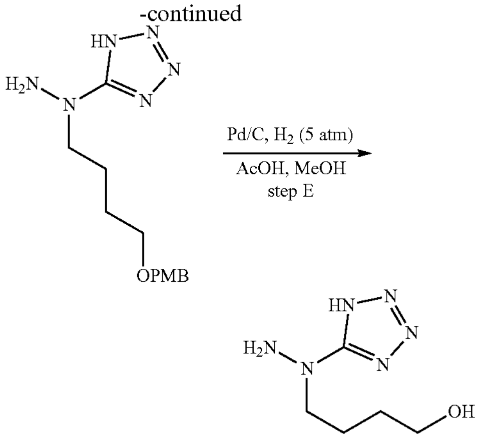

Step A. Synthesis of 4-((4-methoxybenzyl)oxy)butyl methanesulfonate

To a solution of 4-((4-methoxybenzyl)oxy)butan-1-ol (4.0 g, 19.0 mmol) in DCM (50 mL) was added $Et_3N$ (2.88 g, 28.5 mmol) and MsCl (2.4 g, 20.9 mmol) at 0° C. The reaction mixture was stirred at rt for 3 h. The mixture was washed with $H_2O$ and extracted with EtOAc. Evaporated and purified by flash chromatography (Silica gel 60-120, ethyl acetate/hexane=1:4) to afford 4-((4-methoxybenzyl)oxy)butyl methanesulfonate as a yellow oil (4.0 g, 73% yield). LC-MS $(M+1)^+$: 289.

Step B. Synthesis of (4-((4-methoxybenzyl)oxy)butyl)hydrazine

To a solution of afford 4-((4-methoxybenzyl)oxy)butyl methanesulfonate (4.0 g, 13.9 mmol) in ethanol (15 mL) was added hydrazine monohydrate (15 mL) and the mixture was heated to 60° C. for 2 h then concentrated to afford (4-((4-methoxybenzyl)oxy)butyl)hydrazine (1.6 g, 52% yield) as a yellow oil. LCMS $(M+1)^+$: 225.

Step C. Synthesis of 1-(4-((4-methoxybenzyl)oxy)butyl)hydrazinecarbonitrile

The solution of BrCN (1.13 g, 10.7 mmol) in DCM (20 ml) was cooled to 0° C., A mixture of (4-((4-methoxybenzyl)oxy)butyl)hydrazine (1.6 g, 7.1 mmol), $Na_2CO_3$ (1.13 g, 10.7 mmol) and 10 ml $H_2O$ was added dropwise under vigorous stirring for 1 h. The solution was extracted with DCM, concentrated and purified by column chromatography to give 1-(4-((4-methoxybenzyl)oxy)butyl)hydrazinecarbonitrile as a yellow oil (1.0 g, 56% yield). LC-MS $(M+1)^+$: 250.

Step D. Synthesis of 5-(1-(4-((4-methoxybenzyl)oxy)butyl)hydrazinyl)-1H-tetrazole To a solution of 1-(4-((4-methoxybenzyl)oxy)butyl)hydrazinecarbonitrile (1.0 g, 4.01 mmol) in DMF (10 mL) was added $NaN_3$ (391 mg, 6.02 mmol) and $NH_4Cl$ (322 mg, 6.02 mmol). Then the reaction mixture was heated at 90° C. for 1.5 h. The mixture was filtrated, the filtrate was concentrated. The residue was purified by column chromatography to give 5-(1-(4-((4-methoxybenzyl)oxy)butyl)hydrazinyl)-1H-tetrazole as a white solid (250 mg, 21% yield). LC-MS $(M+1)^+$: 293.1.

Step E. Synthesis of 4-(1-(1H-tetrazol-5-yl)hydrazinyl)butan-1-ol

To a solution of 5-(1-(4-((4-methoxybenzyl)oxy)butyl)hydrazinyl)-1H-tetrazole (60 mg, 0.21 mmol) in MeOH (3 mL) and AcOH (1 mL) was added Pd/C (10 mg). The resulting mixture was stirred overnight at rt under $H_2$ (6 atm) atmosphere. The mixture was filtered, the filtrate was concentrated and purified by Prep-HPLC to afford 4-(1-(1H-tetrazol-5-yl)hydrazinyl)butan-1-ol (5 mg, 14% yield). $^1H$ NMR (400 MHZ, $D_2O$) δ: 3.56-3.49 (m, 4H), 1.66-1.63 (m, 2H), 1.51-1.47 (m, 2H); LC-MS $(M+1)^+$: 173.

Example 34

Synthesis of 5-(1-methylhydrazinyl)-1H-tetrazole

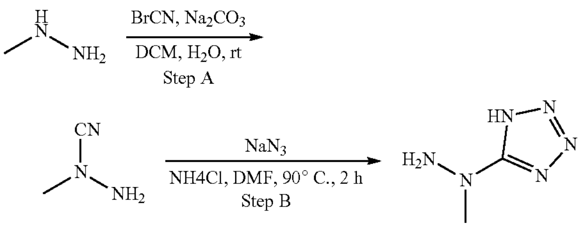

Step A. Synthesis of 1-(methyl-d3)hydrazine-1-carbonitrile

The solution of BrCN (13.8 g, 130 mmol) in DCM (300 ml) was cooled to 0° C., A mixture of methyl hydrazine (6 g, 40% in $H_2O$), $Na_2CO_3$ (2.07 g, 195 mmol) and 60 ml $H_2O$ was added dropwise under vigorous stirring. The solution was extracted with DCM, concentrated and purified by column chromatography to give 1-(methyl-d3)hydrazine-1-carbonitrile as a yellow oil (2.7 g, 29.2% yield). LCMS $(M+1)^+$: 72.

Step B. Synthesis of 5-(1-methylhydrazinyl)-1H-tetrazole

To a solution of 1-(methyl-d3)hydrazine-1-carbonitrile (4.55 g, 64.1 mmol) in DMF (15 mL) was added $NaN_3$ (4.16 g, 64.1 mmol) and $NH_4Cl$ (3.43 g, 64.1 mmol). Then the reaction mixture was heated at 90° C. for 1.5 h. The mixture was filtrated, the filtrate was concentrated. The residue was recrystallize from $EtOH/H_2O=1/1$ to give desired product as a white solid (3.5 g, 47.8% yield). $^1H$ NMR (400 MHZ, DMSO-$d_6$) δ 14.62 (s, 1H), 4.98 (s, 2H), 3.14 (s, 5H); LCMS $(M+1)^+$: 115.

Example 35

Synthesis of 1-benzyl-5-(1-methylhydrazinyl)-1H-tetrazole

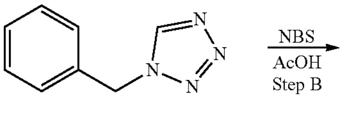

-continued

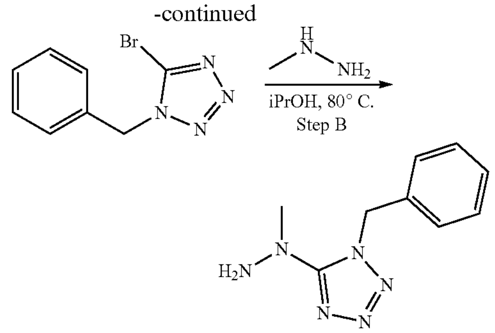

Step A. Synthesis of 1-benzyl-5-bromo-1H-tetrazole

To a stirred solution of 1-benzyl-1H-tetrazole (600 mg, 3.7 mmol) in AcOH (5 mL) was added NBS (796 mg, 4.5 mol) at room temperature. The reaction mixture was stirred at 85° C. for 6 h and concentrated under reduced pressure. The residue was purified by column chromatography (Silica gel 60-120, 1:3, ethyl acetate/hexane) to give the desired product 1-benzyl-5-bromo-1H-tetrazole as a white solid (560 mg, 63.0% yield). LC-MS $(M+1)^+$: 239.

Step B. Synthesis of 1-benzyl-5-(1-methylhydrazinyl)-1H-tetrazole

To a stirred solution of 1-benzyl-5-bromo-1H-tetrazole (560 mg, 2.4 mmol) in iPrOH (5 mL) was added Methylhydrazine (5 ml, wt: 30% in water) at room temperature. The reaction mixture was stirred at 80° C. overnight. After completion of the reaction, the reaction mixture was diluted with ice water and extracted with DCM (2×20 mL). The combined organic layers were washed with brine (1×20 mL), dried over $Na_2SO_4$ and concentrated under reduced pressure to give the desired compound, 1-benzyl-5-(1-methylhydrazinyl)-1H-tetrazole as a white solid (340 mg, 70.9% yield). $^1H$ NMR (400 MHZ, DMSO-$d_6$) δ: 7.35-7.23 (m, 5H), 5.80 (s, 2H), 4.91 (s, 2H), 3.15 (s, 3H); LCMS $(M+1)^+$: 205.

Example 36

Validation of ALAS2 as a Target for Inhibition for Treatment of Porphyrias

The objective of this series of experiments was to explore and validate ALAs2 inhibition as an effective intervention strategy to treat erythroporphyrias (XLP, EPP and CEP). This was achieved by experimental verification of ALAS2 being the rate-limiting enzyme in the heme biosynthetic pathway. Thus, inhibition of ALAS2 or reduction in ALAS2 protein level is expected to reduce pathway flux that should suppress the production of toxin metabolites such as PPIX, uroporphyrin I or coproporphyrin I, or heme and help ameliorate all three erythroporphyrias as well as Del5q MDS and DBA, two anemia diseases that are thought to be caused by accumulation of excess heme. Additionally, in vivo target validation was achieved by genetic knockdown of ALAS2 with delAT mutation in a novel XLP mouse model. Thus, ALAS2 could be inhibited by a small molecule in the XLP mouse model to decrease bone marrow ALA and PPIX.

36.1. Mass Isotopomer Distribution of PPIX Using $^{13}C$-glycine

TF-1 cells, maintained in 10% FBS RPMI medium with 2 ng/ml GM-CSF (R&D Systems), were transduced with a lentivirus to introduce a shRNA against human FECH with a puromycin marker (shRNA sequence: GACCATATTGAAACGCTGTAT). Erythroid differentiation of these TF-1 cells with FECH knocked down was induced by maintaining the cells in 10% FBS RPMI medium with 5 U/ml erythropoietin (R&D Systems). After 6 days of in vitro differentiation, cells were placed in specially formulated RPMI medium without glycine, supplemented with 10% dialized FBS, 0.2 mM $^{13}C_2$-glycine, and 5 U/ml erythropoietin. At different timepoints, $0.5\times10^6$ cells were spun down at 14,000 rpm at 4° C. and lyzed immediately with 80% methanol/20% water on dry ice. Insoluble matters were removed by centrifugation. The liquid layer was dried down under vacuum prior to LC-MS analysis. Porphyrins were separated using a Thermo Hypersil Gold Column (50×2.1 mm, 1.9 μm particle size). Mobile phase A consisted of H2O with 0.1% formic acid and mobile B consisted of acetonitrile with 0.1% formic acid. The gradient at a flow rate of 400 AL min-1 was applied as follows: 0-1 min 30% B, 1-6 min 98% B, 6-7 min 98% B, 7-7.1 min 30% B, 7.1-8.5 min 30% B. LC/MS was conducted using a Thermo Vanquish Flex pump coupled to a Thermo QExactive Mass Spectrometer operated in positive ESI, full scan mode. Amino-levulinic acid was separated using a Thermo Vanquish Flex pump delivered a gradient of 0.025% heptafluorobutyric acid, 0.1% formic acid in water and acetonitrile at 400 μl min−1 (PMID: 20349993). The stationary phase was an Atlantis T3, 3 μm, 2.1 mm×150 mm column. Data was acquired on a QExactive mass spectrometer operated at 70,000 resolving power in full-scan ESI positive mode (PMID: 20349993).

36.2. Generation of XLP Mouse Model with ALAS2-delAT Mutation

Materials for microinjection: For in vitro transcription of sgRNA, a DNA template was amplified from a plasmid containing the sgRNA sequence by PCR, using T7 promoter tagged primers (T7-sgRNA_F: ttaatacgactcactataggCTTTGAACTTATGAGCGAGT, sgRNA_R: AAAAGCACCGACTCGGTGCC (SEQ ID NO:4)). After purification, in vitro transcription was performed using the MEGAshortscript T7 kit and MEGAclear kit according to the protocol (Ambion). Cas9 mRNA was in vitro transcribed from pUC-cas9 vector using mMESSAGE mMACHINE T7 kit (Ambion). To introduce the mutation, a ssDNA oligo with the desired alteration flanked on each side by ~80 bases homologous to the sequence adjoining the double-stranded break was synthesized. To prevent DNA being cut after HDR and provide a SacI restriction site for genotyping, several additional silent mutations were also introduced: ssDNA sequence (SEQ ID NO: 5)

```
CTGGCCTGGACTGAGGTGGGGCTGCCCCTCCAAGATGTGTCTGTG

GCTGCATGCAACTTCTGTCATCGTCCTGTGCACTTTGAgCTcGAa

tGAGTGGGAGCGATCCTACTTTGGGAACATGGGACCCCAATATGT

TACCACCTATGCTTAAGGAGCCAGCTGCCTTGGATGCCAGCTCCA
```

Pronuclear injection: 10~15 C57BL/6 females (4-week-old) were injected with PMSG (5 IU-10 IU) on day 1. 48 hours later, the mice were injected with HCG (5 IU-10 IU) and then housed with C57BL/6 male overnight. In the morning of day 4, female mice with copulation plugs were collected for zygote preparation. Zygote-cumulus complexes from the oviduct were collected from euthanized mice and suspended in hyaluronidase solution for several minutes until the cumulus cells fell off, which were then washed several times in M2 medium. The embryos were then placed in equilibrated M16 medium (medium covered with mineral oil) at 37° C. in a 5% $CO_2$ incubator. Cas9 mRNA, sgRNA, and ssDNA (all 10 ng/ul) were injected into the pronucleus of the zygotes. Injected zygotes were then cultured in M16 or KSOM medium at 37° C. in a 5% $CO_2$ incubator until two-cell stage, at which point they were implanted into the oviduct of pseudo-pregnant foster mothers at 0.5 dpc. As ALAS2 is an X-linked gene, the following symbols are used to describe mice carrying the ALAS2-delAT mutation: $ALAS2^{delAT/Y}$ (male); $ALAS2^{delAT/WT}$ or $ALAS2^{delAT/delAT}$ (female).

Genotyping: Genomic DNAs were extracted from tails and toes of the 7-day-old pups and used in PCR amplification of the sequence around the targeting site. The resultant PCR products were TA cloned and sequenced to identify $F_0$ mice, which were back crossed with wildtype C57BL/6 mice to identify $F_1$ mice with germline transmitted mutation.

36.3. Generation of a Mouse Line in Which ALAS2 Protein Can be Knocked Down in an Inducible Manner Via Doxycycline Treatment.

This mouse line was custom ordered from Mirimus, Inc (NY; mirimus.com/). The following shRNA sequence was used to target both wildtype mouse ALAS2 and mutant ALAS2 with delAT mutation: UGAAAAAUUGGUCAUAACCGAA (SEQ ID NO:6). This mouse line carries the expression cassette of the reverse tetracycline-controlled transactivator (rtTA) under a Rosa26 promoter on chromosome 6. In addition, the expression cassette for the ALAS2-shRNA (shALAS2) under the TRE promoter was knocked into chromosome 11 at the ColA1 locus. Expression of ALAS2 shRNA could be induced by treatment of the mice with doxycycline in food to knock down ALAS2 or ALAS2-delAT protein expression. The following symbols are used to described mice carrying these two transgenes: $rtTA^{+/-}$ (heterozygous); $rtTA^{+/+}$ (homozygous); $shALAS2^{+/-}$ (heterozygous); $shALAS2^{+/+}$ (homozygous).

Mice were first bred to homozygosity ($rtTA^{+/-}$/$shALAS2^{+/+}$). To demonstrate shRNA-mediated ALAS2 protein knockdown, 8 mice were randomized into two groups based on weight (n=4 each). One group was fed with regular chow and the other with chow containing 500 mg/kg doxycycline for 4 days. Mice were then euthanized. To collect bone marrow tissues, both femurs and tibias were harvested. Muscles and all connective tissues were removed. With both ends of the bones snipped off, each femur/tibia set (2 sets per mouse) was placed in a 2 ml Eppendorf tube stacked end-to-end and spun at 4° C. for 10 mins at ×13,000 g. Bones were then carefully removed. The bone marrow tissue pellets was used for western blot to measure ALAS2-delAT protein level. Briefly, the pellets were dissolved in RIPA buffer. Equal volume of lysates were separated by electrophoresis on a NuPAGE 4-12% Bis-Tris gel (Invitrogen). Proteins were visualized by western blotting using the following antibodies. The ALAS2 antibody is a mouse monoclonal antibody against an internal region of ALAS2 protein (DPDHLKKLLEKSNPKI (SEQ ID NO:7)). This ALAS2 antibody was validated to only recognize ALAS2 but not ALAS1. The actin antibody is a rabbit antibody from Cell Signaling.

To demonstrate shRNA gene dosage effect on ALAS2 protein knockdown, the ALAS2 protein level in mice was compared with one or two copies of shALAS2 after doxycycline treatment. In one experiment, 3 WT $C_{57}B6$ mice and 4 $rtTA^{+/-}$/$shALAS2^{+/-}$ mice were fed with doxycycline-containing chow for 16 days. Another experiment was set with 3 WT $C_{57}B6$ mice and 4 $rtTA^{+/+}$/$shALAS2^{+/+}$ mice also being fed with doxycycline-containing chow for 16 days. Animals were euthanized at the end of the experiment. Bone marrow ALAS2 protein was analyzed as above.

36.4. In Vivo Experiments.

The mouse line generated from Examples 36.2 and 36.3 were crossed to generate a mouse line with the following genotype: $ALAS2^{delAT/Y}$; $rtTA^{+/-}$; $shALAS2^{+/-}$. This XLP line expressed the disease causing ALAS2-delAT mutation but also harbored one copy of the rtTA and shALAS2 transgene. Upon doxycycline treatment, enough of shALAS2 was expressed to knock down ~50% of ALAS2-delAT protein.

Briefly, 17 $ALAS2^{delAT/Y}$; $rtTA^{+/-}$; $shALAS2^{+/-}$ were randomized into two groups by weight and blood PPIX fluorescence. Eight were kept on normal chow and nine on chow with 500 mg/kg doxycycline. A control group of age-matched WT $C_{57}B6$ mice on dox diet was included to provide a baseline ALA and PPIX values in non-disease mice. The study was carried out for 39 day. Mice were then euthanized. Whole blood was collected and analyzed for PPIX as described in Example 36.6. To collect bone marrow tissues, both femurs and tibias were harvested. Muscles and all connective tissues were removed. With both ends of the bones snipped off, each femur/tibia set (2 sets per mouse) was placed in a 2 ml Eppendorf tube stacked end-to-end and spun at 4° C. for 10 mins at ×13,000 g. Bones were then carefully removed. One set of the bone marrow tissue pellets was used for measuring ALA. The other set of the bone marrow tissue pellets was used for western blot to measure ALAS2-delAT protein level as described in Example 36.3.

36.5 Hydrazine Compounds Inhibits PPIX Production in EPP and XLP In Vitro Cell Models.

In Vitro EPP Cell Model Using Engineered A549 Cells

Endogenous ALAS1 in A549 cells was knocked out by CRISPR/CAS9 using the Targeting System from SBI System Biosciences. The following two homologous arms were cloned into pHR510PA-1 vector to target exon 4 of human ALAS1:

```
homologous arm 1:
                                       (SEQ ID NO: 8)
GTGAGGCTGGGCACAGTAGCTCATACCTGTAATCCCAGCACTTTG

GGAGGCTGAAGCGGGAGAAGATCACTTGAGGCCAGGAGTTTGAGG

CCAGCCTTGGCAACATAGCAAGACACTATCTCTACCAAAACAGTT

TTTTTAATTAGCCAGGCATGATGGCTTGCATCTATAGTCCCAGCT

ACTCAGGAGGCTAAGGTAGGAAGATTGCTTAAGCCCAAGACTTCA

AGGTTCAGTGAGCTATGATCACGCTATTGCACTCCAGCCTGAATG

ACAGACAGAGACTCAGTTTCTAGGAAAAACAAAAAAATGTATGGT

GAGTTGAGGCTTGAAAGCCATATCCCTTGCTTGCGTGAGCAGGTG

CTTTTGGTTGTGGTGACTACAGGTGCTGTTGGTAGCCTGCCTTCT

GTCCTTTAATACTTACCGTCTACACATGGCACTGAGCCAAACACG

ACATACAGTCTTATTTACTTACAAGATGAGGACATCAAATAACCT

GCCCAGGATCTCCCTCAGTTGCCAAGCTGAGACTTGTTGTATTTC

ACCAAAATGCAGCTGTGTTTCACAACCACCATTCTGTACTGTCTT

TTGTTCAATTTTTAGCTGTTTCCACTTTTCAGTATGATCGTTTCT
```

-continued

```
TTGAGAAAAAAATTGATGAGAAAAAGAATGACCACACCTATCGAG

TTTTTAAAACTGTGAACCGGCGAGCACACATCTTCCCCATGGCAG

ATGACTATTCAGACTCCCTCATCACCAAAAAGCAAGTGTCAGTCT

GGTGCAGTAATGACTACCTAGGAATGAGTCGC
```

homologous arm 2:

(SEQ ID NO: 9)

```
TGTGGGGCAGTTATGTAAGTAGCCCTTGGCTTTCAAATATTACTG

TTGTTATTTGGCAAGCCAATGATGATGTATAGGGGTTGGATCTTT

TATGGAGGGAACATTCAGTAGCTGAAAGTGTGCCATAGCAAAATA

CTATTCTTAGCTTCTGAAAAATATCTACAGATTACTTTTAAAGGA

ACTCTAATATGCAGGTAGCTGCTGGAGCCCCTTAACTTGTGAGGG

TTCAAGCTTATAGGCTCAATGACCACACACGTCAGTCCACTTTCT

ATCACTCTGCAAGTGAGTGTGCCTTTAACACCAGGCAGTCTTTCA

CAGAGACATCCTTGGTTGTGGCTGTGAGTGGAGAAATACGAATCT

AGCAGCGCTAGAGAAAAAGCTACTCCAAAAGACATGTTAAAAAGG

ATGGTAGATCCCATCACTCGTCCTTCAGGAGGCTCACCATCCTAG

GGATGCTGGAGAGAGTTGCTGGCCAGATTCTCCAAAGGCTTGCTA

AAGAGGGTCCCGGTTTGAGGTTTAATGATAGTGATATATCCAAAC

ATTACATGACTGGCTTGCAGAGGGTAACCACCATCCAGGATGTCC

CTCTAGAGTTTGCTTTTTCTTAAGCTAACATGTTATTGGAAAGAA

TAATGTTTCTCAGAAAATAAACCTTAGTTTCTTAGAAAAGAAACT

CAGCTAATACCAAGCACTTACTGACTGTTAAATGAACACTTGTTC

TTGATGATTCCTGGAGGTATCATCACCCTAGCATTGACACCTTCT

CCCACCTAGTCTGAAGATGAAATCAGTTG
```

The following guide sequence was cloned into the SmartNuclease vector (pSN): GATGGCACACAGCT TCCGTC (SEQ ID NO:10). The resultant pHR and pSN plasmids were co-transfected into A549 cells by Lipofectamine. Cells were selected by hygromycin. Western blot for ALAS1 protein was performed to identify individual clones that had endogenous ALAS1 knocked out.

Next, full-length human ALAS2 was re-expressed in these cells via lentiviral transduction (pL VX-EF1a-human-ALAS2-IRES-geneticin). After geneticin selection, cells were transduced with a lentivirus to introduce a shRNA against human FECH with a puromycin marker (shRNA sequence: GACCATATTGAAACGCTGTAT (SEQ ID NO:11)). The resultant cells have endogenous ALAS1 knocked out, ALAS2 overexpressed, and FECH knocked down. These cells will be referred as A549-ALAS2 cells.

For PPIX cell assays, on day 1, 10,000 cells/100 ul RPMI (10% FBS) were seeded in each well of a 96-well plate. On day 3, medium was replaced with fresh RPMI (10% FBS) supplemented with 2.5 mM glycine and different concentrations of compounds. On day 4, PPIX fluorescence, used as a surrogate for PPIX level, was measured using a fluorescence plate reader (ex 410 nm and em 690 nm). Cell viability was then determined via CellTiter-Glo assay (Promega). Data were background subtracted and normalized to values from DMSO-treated cells, which was arbitrarily set as 100%.

In Vitro XLP Cell Model

On day 1, hindlegs from ALAS2$^{delAT/Y}$ mice were harvested. The tips of the bones were cut. Bone marrow cells were flushed out using FBS, strained through a 70-um cell strainer, and spun down at 300 g for 5 mins. Lineage positive cells were depleted using the Direct Lineage Cell Depletion kit (mouse) from Miltenylbiotec. Cell pellets were resuspended in 1 ml MACS buffer supplemented with 50 ul/ml rat serum. Samples were transferred to a 14 ml round-bottom tube and 50 uL/ml of isolation cocktail was added each samples and were then incubated on ice for 15 mins, followed by addition of 75 ul of vortexed RapidSpheres. After a 10-min incubation on ice, sample volume was brought up to 5 ml with MAC buffer. Cells were magnetically separated and re-suspended in differentiation medium (IMDM medium supplemented with 200 ug/ml holo-transferrin, 10 ug/ml insulin, 2 mM glutamine, 0.1 mM BME, 100 ng/ml IGF1, 10 uM dexamethasone, 80 ng/ml mouse EPO, 10 ng/ml mouse SCF, 15% v/v FBS, and 1% v/v detoxified albumin) at 0.5 million cells/ml. 100 ul of cells were plated into one well of a type-1 collagen-coated 96-well plate.

On day 2, differentiation medium was removed. Cells were then treated with 100 ul of EDM medium (IMDM medium with 20% FBS, 2 mM glutamine, and 0.1 mM BME) containing different concentrations of compounds for 48 hours, at which point PPIX fluorescence was measured and cell viability determined via Cell-TiterGlo.

36.6. Treating XLP Mice with Compound E1.

ALAS2$^{delAT/Y}$ mice were randomized based on weight and blood PPIX fluorescence into two groups. Group 1 (n=15) was dosed with Compound E1 suspended in saline at 10 mg/ml at 12 mg/kg BID via oral gavage 8 hours apart. 0.5, 6, and 24 hours after first dose, mice (n=5 per time point) were euthanized by cardiac puncture. Group 2 (ALAS2$^{delAT/Y}$, n=4) and Group 3 (WT $C_{57}$/B6, n=5) were mocked treated with vehicle as controls. Plasma was collected by centrifugation of whole blood and used for measuring of plasma exposure of Compound E1. Briefly, 40 μl of plasma was mixed with 200 μl of methanol containing 4-nitrobenzaldehyde (10 mg/mL). The derivatization was carried out at room temperature for 1 hour. The mixture was then centrifugated at 5800 rpm for 10 min. An aliquot of 100 μl was mixed with 10 μl of acetonitrile:water (1:1, v/v) containing Oslamid (2 ug/mL, IS). The sample was subsequently mixed and 1 μl of the supernatant was injected into the UPLC-MS/MS system. The LC separation was carried out using a Thermo Hypersil Gold (2.1×50 mm, 1.9 μm) set at 40° C., and a gradient starting at 80% water (with 0.1% formic acid) and 20% methanol (with 0.1% formic acid) that reached 95% methanol (with 0.1% formic acid) in 2.5 min with a flow rate of 0.4 ml/min. The MRM transition, 246 to 98, was monitored for Compound E1. Calibration standards and quality control samples were prepared in blank mouse plasma. The standard curve had a coefficient of determination ($R^2$) value >0.98 in a linear regression. The quality control samples had a precision and accuracy within +20% of theoretical values. The peak area ratios of analyte relative to the internal standard (IS) were used for Compound E1 quantitation. To collect bone marrow tissues, both femurs and tibias were harvested. Muscles and all connective tissues were removed. With both ends of the bones snipped off, each femur/tibia set (2 sets per mouse) was placed in a 2 ml Eppendorf tube stacked end-to-end and spun at 4° C. for 10 mins at ×13,000 g. Bones were then carefully removed. The bone marrow was used to measure three different endpoints: Compound E1, 5-aminolevulinic acid (5-ALA) and protoporphyrin IX (PPIX). The bone marrow tissues pellets were homogenized with 4 volume of PBS (pH7.4) to allow the parallel measurements of our different endpoints. A 40 µl aliquot of bone marrow homogenate was then derivatized using the same method described for plasma. Subsequently, 1 µl of the derivatized bone marrow extract was analyzed using the same UPLC-MS/MS method than previously described to quantify Compound E1. A second aliquot of bone marrow homogenate was further diluted in in 3 volume of PBS (v/v) to achieve and 20 fold dilution factor. 80 µl of the 20 fold diluted bone marrow extract was combine with 80 µl of a label internal standard $^{13}C_5$, $^{15}N$-5-aminlevulinic acid prepared in PBS. Subsequently the 160 µl solution was loaded on an Oasis MCX solid phase extraction. Using standard procedure recommended by the manufacture, the 5-ALA and the label IS was extracted. Then the extract was further derivatized using 200 µl of 3N HCl in N-butanol for 1 hour at room temperature. Following the derivatized step, the sample was dried using nitrogen gas. The final sample was reconstituted in 150 µl of 20% methanol in water and 5 µl was injected into the UPLC/MS-MS system. The LC separation was carried out using a Thermo Hypersil Gold AQ (3×100 mm, 3 µm) set at 40° C., and a gradient starting at 80% water (with 0.1% formic acid) and 20% methanol (with 0.1% formic acid) that reached 95% methanol (with 0.1% formic acid) in 2.5 min with a flow rate of 0.4 ml/min. The MRM transition, 188.1 to 114, was monitored for to quantified derivatized 5-ALA. The last aliquot of bone marrow homogenate used to measure PPIX was extracted using a liquid:liquid extraction. The extracting solution was composed of acetonitrile:methanol:formic acid:water (40:40:40:10:10, v/v/v/v) and 4 volumes were added to the bone marrow homogenate to obtain a diluted-homogenized bone marrow sample. Subsequently the sample was vortex and centrifuged at 14,000 rpm for 5 minutes. 10 µl of the diluted-homogenized bone marrow was further mixed with 10 µl the previous extract solution to which an additional 200 µl of acetonitrile:methanol:formic acid (50:50:5, v/v/v) containing 5 ng/ml candesartan ciloexetil (IS) was added. The sample was mixed well and centrifuged at 5800 rpm, 4 C for 10 min. A final step dilution was carried out by combining 50 µl of the supernatant with 50 µl of 0.1% formic acid in methanol:water (1:1. v/v), and 5 µl was injected into the UPLC/MS-MS system. The LC separation was carried out using a Thermo Hypersil Gold C8 (2.1×50 mm, 1.9 µm) set at 40° C., and a gradient starting at 50% mobile phase A (0.2% formic acid, methanol:water, 1:1, v/v) and 50% mobile phase B (0.2% formic acid, acetonitrile:methanol:water, 40:50:10, v/v/v) that reached 95% mobile phase B in 2 min with a flow rate of 0.6 ml/min. The MRM transition, 563.2 to 431.2, was monitored for to quantified derivatized PPIX.

Example 37

Expression and Purification

ALAS2 sequence (see FIG. 8) (residues 79-587) was expressed in *E. coli* as a TEV cleavable C-terminally MBP tagged construct. Purification steps included an amylose column, followed by MBP tag cleavage and passage through a Ni-NTA column to remove cleaved MBP. ALAS2 was further purified and exchanged into storage buffer (50 mM Tris, 500 mM NaCl, 1 mM DTT, 10 µM PLP, pH 8.0) by size exclusion through a Superdex 200 column and stored at −80° C.

Example 38

General $IC_{50}$ Assay Protocol

Preparation of stock solutions: All solutions were prepared by standard methods with the exception of glycine and succinyl CoA. A 1 M solution of glycine was prepared and the pH adjusted to 8.0 by addition of 1 N HCl. A 1 mM solution of succinyl CoA was prepared in 20 mM phosphoric acid, pH 2.0 to ensure its stability to hydrolysis.

Routine compound testing for $IC_{50}$ measurements: Assays were carried out in 96-well V-bottom polypropylene plates (Greiner-Bio cat. no. 651201) at room temperature. Test compound dilution series and DMSO blanks (1 µL) were dispensed into the 96-well plates. A solution of 1.1× assay mix was prepared to contain, in the final 1× assay conditions: 5 µg/mL ALAS2 (for the version 1 assay) or 2 ug/mL (for the version 2 assay), 20 mM sodium phosphate pH 8.0, 3.5 mM glycine, 1 mM $MgCl_2$, 30 mM NaCl, 0.03% BSA, 1 mM EDTA. Assay mix (45 µL) was added to each well, and compound and assay mix were pre-incubated for 1 h at room temperature. Assays were then initiated by addition of 5 µL 1 mM succinyl CoA to each well to give a final concentration of 100 µM. Reactions proceeded for 1 h (version 1 assay) or 2 h (version 2 assay) at room temperature, then were quenched by addition of 200 µL acetonitrile containing 1% formic acid and 0.2 µg/mL $^{13}C$, $^{15}N$ aminolevulinic acid (ALA) as an internal standard. The plates were centrifuged at 4° C. for 1 min at 3500 rpm, then 200 µL of supernatant was transferred to a fresh 96-well plate for detection of ALA by high throughput mass spectrometry.

Measurement of ALA concentration by high throughput mass spectrometry: ALA was monitored in positive mode on a Sciex QTRAP 6500 connected to a Shimadzu 20AD LC using the conditions outlined in the table below. Samples were transferred from the assay plate and loaded onto a ZIC HILIC Trap column (Optimize Technologies, 4 µL, 10 µM) at a flow rate of 1.2 mL/min in 99% acetonitrile, 1% $ddH_2O$ containing 0.5% formic acid to remove nonvolatile components with a 6 s desalt cycle. Analytes were eluted with 95% acetonitrile, 5% $ddH_2O$ containing 0.5% formic acid in 12 s elution cycles. Concentrations of ALA in each sample were measured by comparison to an authentic standard curve, and $IC_{50}$s were determined by fitting to the log(compound) vs. response equation Y=bottom+(top−bottom)/(1+10^((log IC50-X)*HillSlope)).

TABLE 3

Mass spectrometry settings for analysis of ALA.

| ID | Q1 Mass (m/z) | Q3 Mass (m/z) | Time (ms) | DP (V) | CE (V) |
|---|---|---|---|---|---|
| ALA_1 | 132.0 | 114.0 | 100 | 10 | 10 |
| ALA_2 | 132.0 | 86.0 | 100 | 10 | 20 |
| 13C, 15N ALA_1 | 138.0 | 120.0 | 100 | 10 | 11 |
| 13C, 15N ALA_2 | 138.0 | 91.0 | 100 | 10 | 20 |

While a number of embodiments have been described, the scope of this disclosure is to be defined by the appended claims, and not by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A mouse (*Mus musculus*) as an animal model for X-linked protoporphyria (XLP), wherein the mouse comprises a genomic ALAS2 (5-AminoLevulinic Acid Synthase 2)-delAT mutation at the mouse ALAS2 locus comprising the genomic DNA sequence of SEQ ID NO: 5, wherein the mouse has an elevated level of blood protoporphyrin IX (PPIX) and Zn-PPIX compared to a syngeneic wild-type mouse, and wherein the genomic ALAS2-delAT mutation encodes a mutant ALAS2 protein comprising an M567E substitution followed by a C-terminal deletion, and corresponds to or recapitulates the human ALAS2-delAT (c.1699_1670ΔAT) mutation in an XLP human patient.

2. The mouse of claim 1, which is a C57BL/6 mouse.

3. The mouse of claim 1, which is a male ($ALAS2^{delAT/Y}$).

4. The mouse of claim 1, which is a female.

5. The mouse of claim 4, which is homozygous for the genomic ALAS2-delAT mutation ($ALAS2^{delAT/delAT}$).

6. The mouse of claim 4, which is heterozygous for the genomic ALAS2-delAT mutation.

7. The mouse of claim 1, which is generated by CRISPR/Cas9-mediated homology-directed repair (HDR) that deletes the AT dinucleotide in the genomic ALAS2-delAT mutation.

8. The mouse of claim 7, wherein the CRISPR/Cas9-mediated HDR utilizes a single guide RNA (sgRNA) comprising the nucleotide sequence of SEQ ID NO: 4.

9. The mouse of claim 7, wherein the CRISPR/Cas9-mediated HDR utilizes a donor DNA having the polynucleotide sequence of SEQ ID NO: 5.

10. The mouse of claim 7, wherein the CRISPR/Cas9-mediated HDR is carried out by microinjecting into the pronucleus of a mouse zygote an mRNA encoding Cas9, an sgRNA, and a single-stranded DNA (ssDNA).

11. The mouse of claim 1, wherein the mouse further comprises (i) at least one expression cassette comprising a polynucleotide encoding a reverse tetracycline-controlled transactivator (rtTA) under transcriptional control of a Rosa26 promoter and (ii) at least one expression cassette comprising a polynucleotide encoding an ALAS2 shRNA sequence (shALAS2) under transcriptional control of a TRE promoter.

12. The mouse of claim 11, wherein the expression cassette comprising a polynucleotide encoding an rtTA is inserted into chromosome 6.

13. The mouse of claim 11, wherein the expression cassette comprising a polynucleotide encoding shALAS2 is inserted into chromosome 11 at the ColA1 locus.

14. The mouse of claim 11, wherein the mouse is heterozygous for the ALAS2-delAT mutation, heterozygous for rtTA (rtTA+/−) and heterozygous for shALAS2 (shALAS2+/−).

15. The mouse of claim 11, wherein the shALAS2 comprises the sequence UGAAAAAUUGGUCAUAACCGAA (SEQ ID NO: 6).

* * * * *

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1

```
gtgcactttg agctcgaatg ag                                              22
```

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

```
Val His Phe Glu Leu Glu
1               5
```

<210> SEQ ID NO 3
<211> LENGTH: 587
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Met Val Thr Ala Ala Met Leu Leu Gln Cys Cys Pro Val Leu Ala Arg
1               5                   10                  15

Gly Pro Thr Ser Leu Leu Gly Lys Val Val Lys Thr His Gln Phe Leu
            20                  25                  30

Phe Gly Ile Gly Arg Cys Pro Ile Leu Ala Thr Gln Gly Pro Asn Cys
        35                  40                  45

Ser Gln Ile His Leu Lys Ala Thr Lys Ala Gly Gly Asp Ser Pro Ser
    50                  55                  60

Trp Ala Lys Gly His Cys Pro Phe Met Leu Ser Glu Leu Gln Asp Gly
65                  70                  75                  80

Lys Ser Lys Ile Val Gln Lys Ala Ala Pro Glu Val Gln Glu Asp Val
                85                  90                  95

Lys Ala Phe Lys Thr Asp Leu Pro Ser Ser Leu Val Ser Val Ser Leu
            100                 105                 110

Arg Lys Pro Phe Ser Gly Pro Gln Glu Gln Glu Gln Ile Ser Gly Lys
        115                 120                 125

Val Thr His Leu Ile Gln Asn Asn Met Pro Gly Asn Tyr Val Phe Ser
    130                 135                 140

Tyr Asp Gln Phe Phe Arg Asp Lys Ile Met Glu Lys Lys Gln Asp His
145                 150                 155                 160

Thr Tyr Arg Val Phe Lys Thr Val Asn Arg Trp Ala Asp Ala Tyr Pro
                165                 170                 175

Phe Ala Gln His Phe Ser Glu Ala Ser Val Ala Ser Lys Asp Val Ser
            180                 185                 190
```

-continued

Val Trp Cys Ser Asn Asp Tyr Leu Gly Met Ser Arg His Pro Gln Val
195 200 205

Leu Gln Ala Thr Gln Glu Thr Leu Gln Arg His Gly Ala Gly Ala Gly
210 215 220

Gly Thr Arg Asn Ile Ser Gly Thr Ser Lys Phe His Val Glu Leu Glu
225 230 235 240

Gln Glu Leu Ala Glu Leu His Gln Lys Asp Ser Ala Leu Leu Phe Ser
245 250 255

Ser Cys Phe Val Ala Asn Asp Ser Thr Leu Phe Thr Leu Ala Lys Ile
260 265 270

Leu Pro Gly Cys Glu Ile Tyr Ser Asp Ala Gly Asn His Ala Ser Met
275 280 285

Ile Gln Gly Ile Arg Asn Ser Gly Ala Ala Lys Phe Val Phe Arg His
290 295 300

Asn Asp Pro Asp His Leu Lys Lys Leu Leu Glu Lys Ser Asn Pro Lys
305 310 315 320

Ile Pro Lys Ile Val Ala Phe Glu Thr Val His Ser Met Asp Gly Ala
325 330 335

Ile Cys Pro Leu Glu Glu Leu Cys Asp Val Ser His Gln Tyr Gly Ala
340 345 350

Leu Thr Phe Val Asp Glu Val His Ala Val Gly Leu Tyr Gly Ser Arg
355 360 365

Gly Ala Gly Ile Gly Glu Arg Asp Gly Ile Met His Lys Ile Asp Ile
370 375 380

Ile Ser Gly Thr Leu Gly Lys Ala Phe Gly Cys Val Gly Gly Tyr Ile
385 390 395 400

Ala Ser Thr Arg Asp Leu Val Asp Met Val Arg Ser Tyr Ala Ala Gly
405 410 415

Phe Ile Phe Thr Thr Ser Leu Pro Pro Met Val Leu Ser Gly Ala Leu
420 425 430

Glu Ser Val Arg Leu Leu Lys Gly Glu Glu Gly Gln Ala Leu Arg Arg
435 440 445

Ala His Gln Arg Asn Val Lys His Met Arg Gln Leu Leu Met Asp Arg
450 455 460

Gly Leu Pro Val Ile Pro Cys Pro Ser His Ile Ile Pro Ile Arg Val
465 470 475 480

Gly Asn Ala Ala Leu Asn Ser Lys Leu Cys Asp Leu Leu Leu Ser Lys
485 490 495

His Gly Ile Tyr Val Gln Ala Ile Asn Tyr Pro Thr Val Pro Arg Gly
500 505 510

Glu Glu Leu Leu Arg Leu Ala Pro Ser Pro His His Ser Pro Gln Met
515 520 525

Met Glu Asp Phe Val Glu Lys Leu Leu Leu Ala Trp Thr Ala Val Gly
530 535 540

Leu Pro Leu Gln Asp Val Ser Val Ala Ala Cys Asn Phe Cys Arg Arg
545 550 555 560

Pro Val His Phe Glu Leu Met Ser Glu Trp Glu Arg Ser Tyr Phe Gly
565 570 575

Asn Met Gly Pro Gln Tyr Val Thr Thr Tyr Ala
580 585

<210> SEQ ID NO 4
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
aaaagcaccg actcggtgcc 20

<210> SEQ ID NO 5
<211> LENGTH: 180
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5
ctggcctgga ctgaggtggg gctgcccctc caagatgtgt ctgtggctgc atgcaacttc 60
tgtcatcgtc ctgtgcactt tgagctcgaa tgagtgggag cgatcctact ttgggaacat 120
gggaccccaa tatgttacca cctatgctta aggagccagc tgccttggat gccagctcca 180

<210> SEQ ID NO 6
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
ugaaaaauug gucauaaccg aa 22

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Asp Pro Asp His Leu Lys Lys Leu Leu Glu Lys Ser Asn Pro Lys Ile
1 5 10 15

<210> SEQ ID NO 8
<211> LENGTH: 797
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8
gtgaggctgg gcacagtagc tcatacctgt aatcccagca ctttgggagg ctgaagcggg 60
agaagatcac ttgaggccag gagtttgagg ccagccttgg caacatagca agacactatc 120
tctaccaaaa cagttttttt aattagccag gcatgatggc ttgcatctat agtcccagct 180
actcaggagg ctaaggtagg aagattgctt aagcccaaga cttcaaggtt cagtgagcta 240
tgatcacgct attgcactcc agcctgaatg acagacagag actcagtttc taggaaaaac 300

-continued aaaaaaatgt atggtgagtt gaggcttgaa agccatatcc cttgcttgcg tgagcaggtg 360
cttttggttg tggtgactac aggtgctgtt ggtagcctgc cttctgtcct ttaatactta 420
ccgtctacac atggcactga gccaaacacg acatacagtc ttatttactt acaagatgag 480
gacatcaaat aacctgccca ggatctccct cagttgccaa gctgagactt gttgtatttc 540
accaaaatgc agctgtgttt cacaaccacc attctgtact gtcttttgtt caatttttag 600
ctgtttccac ttttcagtat gatcgtttct ttgagaaaaa aattgatgag aaaaagaatg 660
accacaccta tcgagttttt aaaactgtga accggcgagc acacatcttc cccatggcag 720
atgactattc agactccctc atcaccaaaa agcaagtgtc agtctggtgc agtaatgact 780
acctaggaat gagtcgc 797

<210> SEQ ID NO 9
<211> LENGTH: 794
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9
tgtggggcag ttatgtaagt agcccttggc tttcaaatat tactgttgtt atttggcaag 60
ccaatgatga tgtatagggg ttggatcttt tatggaggga acattcagta gctgaaagtg 120
tgccatagca aaatactatt cttagcttct gaaaaatatc tacagattac ttttaaagga 180
actctaatat gcaggtagct gctggagccc cttaacttgt gagggttcaa gcttataggc 240
tcaatgacca cacacgtcag tccactttct atcactctgc aagtgagtgt gcctttaaca 300
ccaggcagtc tttcacagag acatccttgg ttgtggctgt gagtggagaa atacgaatct 360
agcagcgcta gagaaaaagc tactccaaaa gacatgttaa aaaggatggt agatcccatc 420
actcgtcctt caggaggctc accatcctag ggatgctgga gagagttgct ggccagattc 480
tccaaaggct tgctaaagag ggtcccggtt tgaggtttaa tgatagtgat atatccaaac 540
attacatgac tggcttgcag agggtaacca ccatccagga tgtccctcta gagtttgctt 600
tttcttaagc taacatgtta ttggaaagaa taatgtttct cagaaaataa accttagttt 660
cttagaaaag aaactcagct aataccaagc acttactgac tgttaaatga acacttgttc 720
ttgatgattc ctggaggtat catcacccta gcattgacac cttctcccac ctagtctgaa 780
gatgaaatca gttg 794

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10
gatggcacac agcttccgtc 20

<210> SEQ ID NO 11
<211> LENGTH: 21
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 11

gaccatattg aaacgctgta t                                          21


<210> SEQ ID NO 12
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

ttaatacgac tcactatagg ctttgaactt atgagcgagt                      40


<210> SEQ ID NO 13
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13

gtgcactttg aacttatgag cgag                                       24


<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Val His Phe Glu Leu Met Ser Glu
1               5
```